United States Patent
Kates-Harbeck et al.

(10) Patent No.: US 11,872,042 B2
(45) Date of Patent: Jan. 16, 2024

(54) SELF-CALIBRATION OF FLUX GATE OFFSET AND GAIN DRIFT TO IMPROVE MEASUREMENT ACCURACY OF MAGNETIC FIELDS FROM THE BRAIN USING A WEARABLE NEURAL DETECTION SYSTEM

(71) Applicant: HI LLC, Los Angeles, CA (US)

(72) Inventors: Julian Kates-Harbeck, Marina Del Rey, CA (US); Vincent Maurice, Culver City, CA (US); Ricardo Jimenez-Martinez, Culver City, CA (US); Jamu Alford, Lake Arrowhead, CA (US); Benjamin Shapiro, Culver City, CA (US)

(73) Assignee: HI LLC, Los Angeles, CA (US)

( * ) Notice: Subject to any disclaimer, the term of this patent is extended or adjusted under 35 U.S.C. 154(b) by 438 days.

(21) Appl. No.: 17/160,078

(22) Filed: Jan. 27, 2021

(65) Prior Publication Data

US 2021/0244328 A1 Aug. 12, 2021

Related U.S. Application Data

(60) Provisional application No. 63/035,629, filed on Jun. 5, 2020, provisional application No. 62/975,709, filed on Feb. 12, 2020.

(51) Int. Cl.
*A61B 5/245* (2021.01)
*G01R 35/00* (2006.01)
*A61B 5/00* (2006.01)

(52) U.S. Cl.
CPC ............ *A61B 5/245* (2021.01); *A61B 5/6803* (2013.01); *G01R 35/007* (2013.01); *A61B 2560/0223* (2013.01); *A61B 2562/0223* (2013.01)

(58) Field of Classification Search
CPC .................. A61B 5/245; A61B 5/6803; A61B 2560/0223; A61B 2562/0223;
(Continued)

(56) References Cited

U.S. PATENT DOCUMENTS

| 3,173,082 A | 3/1965 | Bell et al. |
| 3,257,608 A | 6/1966 | Bell et al. |

(Continued)

FOREIGN PATENT DOCUMENTS

| CN | 104730484 | 6/2015 |
| CN | 107562188 | 1/2018 |

(Continued)

OTHER PUBLICATIONS

Li, Hua, et al. "An efficient calibration method for SQUID measurement system using three orthogonal Helmholtz coils." Chinese Physics B 25.6 (2016): 068501. (Year: 2016).*

(Continued)

*Primary Examiner* — Sean D Mattson
(74) *Attorney, Agent, or Firm* — Michael J. Bolan; Vista IP Law Group, LLP

(57) ABSTRACT

A calibration system for a magnetometer having an unknown gain is disclosed. A calibration magnetic field is generated at a calibration frequency of a known amplitude at the magnetometer. A measurement of the calibrating magnetic field is reported by the magnetometer. A ratio of an amplitude of the calibration magnetic field measurement reported by the magnetometer and the known amplitude of the calibrating magnetic field at the magnetometer is computed. The unknown gain of the magnetometer is determined at least partially based on computed ratio.

24 Claims, 17 Drawing Sheets

(58) Field of Classification Search
CPC .......................... G01R 35/007; G01R 35/005; G01R 33/0017; G01R 33/032; G01R 33/0035

See application file for complete search history.

(56) References Cited

U.S. PATENT DOCUMENTS

| | | |
|---|---|---|
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |
| 5,225,778 A | 7/1993 | Challlout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,694,037 A * | 12/1997 | Palstra .................. G01V 15/00 702/92 |
| 5,713,354 A | 2/1998 | Warden |
| 6,144,872 A | 11/2000 | Graetz |
| 6,339,328 B1 | 1/2002 | Keena et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okanden et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,256 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Komack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Komack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,371,764 B2 | 8/2019 | Morales et al. |
| 10,772,561 B2 | 9/2020 | Donaldson |
| 2004/0232912 A1 | 11/2004 | Tsukmamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2009/0318773 A1 | 12/2009 | Jung |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0265042 A1 | 10/2013 | Kawabata et al. |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0219732 A1* | 8/2015 | Diamond .............. G01R 33/16 324/201 |
| 2015/0378316 A1 | 12/2015 | Parsa et al. |
| 2016/0041233 A1* | 2/2016 | Li ..................... G01R 33/0017 324/202 |
| 2016/0041234 A1* | 2/2016 | Li .......................... G01V 3/081 324/202 |
| 2016/0061913 A1 | 3/2016 | Kobayashi et al. |
| 2016/0084925 A1* | 3/2016 | Le Prado ............... G01R 33/24 324/301 |
| 2016/0116553 A1 | 4/2016 | Kim et al. |
| 2016/0223627 A1 | 8/2016 | Shah et al. |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parasa et al. |
| 2017/0261564 A1 | 9/2017 | Gabrys et al. |
| 2017/0281086 A1* | 10/2017 | Donaldson .......... A61B 5/7278 |
| 2017/0299662 A1* | 10/2017 | Nagasaka ........... G01R 33/035 |
| 2017/0332933 A1 | 11/2017 | Krishnaswamy |
| 2017/0343617 A1 | 11/2017 | Manickman et al. |
| 2017/0343695 A1 | 11/2017 | Stetson et al. |
| 2017/1331485 | 11/2017 | Gob et al. |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2019/0391213 A1 | 12/2019 | Alford |
| 2020/0025844 A1 | 1/2020 | Alford et al. |
| 2020/0057115 A1 | 2/2020 | Jimenez-Martinez et al. |
| 2020/0057116 A1 | 2/2020 | Zorzos et al. |
| 2020/0072916 A1 | 3/2020 | Alford et al. |
| 2020/0088811 A1 | 3/2020 | Mohseni |

FOREIGN PATENT DOCUMENTS

| | | |
|---|---|---|
| EP | 2738627 A3 | 6/2014 |
| EP | 2380029 B1 | 10/2015 |
| EP | 3037836 B1 | 9/2017 |
| JP | 2016109665 | 6/2016 |

(56) References Cited

FOREIGN PATENT DOCUMENTS

| JP | 2018004462 | 1/2018 | | |
|---|---|---|---|---|
| WO | 2005081794 | 9/2005 | | |
| WO | WO-2012066527 A1 | * | 5/2012 | ............ G01R 33/032 |
| WO | 2014031985 | 2/2014 | | |
| WO | 2017095998 | 6/2017 | | |

OTHER PUBLICATIONS

Okada, Y.C., Lahteenmäki, A. and Xu, C., "Experimental analysis of distortion of magnetoencephalography signals by the skull." Clinical neurophysiology 110 (2), 230-238 (1999).

Robinson, J.T., Pohlmeyer, E., Gather, M.C., Kemere, C., Kitching, J.E., Malliaras, G.G., Marblestone, A., Shepard, K. L., Stieglitz, T. and Xie, C., "Developing Next-Generation Brain Sensing Technologies—A Review." IEEE sensors journal, 19(22), 10163-10175 (2019).

Shah, V., Knappe, S., Schwindt, P.D. and Kitching, J., "Subpicotesla atomic magnetometry with a microfabricated vapour cell." Nature Photon 1, 649-652 (2007).

Kitching, J., "Chip-scale atomic devices." Applied Physics Reviews, 5(3), 031302 (2018).

Hill, R.M., Boto, E., Rea, M., Holmes, N., Leggett, J., Coles, L.A., Papastavrou, M., Everton, S.K., Hunt, B.A.E., Sims, D. and Osborne J., "Multi-channel whole-head OPM-MEG: helmet design and a comparison with a conventional system." Neuroimage 219, 116995 (2020).

Griffith, W.C., Knappe, S. and Kitching, J., "Femtotesla atomic magnetometry in a microfabricated vapor cell." Optics express 18, (26), 27167-27172 (2010).

Boto, E., Holmes, N., Leggett, J., Roberts, G., Shah, V., Meyer, S.S., Muñoz, L.D., Mullinger, K.J., Tierney, T.M., Bestmann, S. and Barnes, G.R., "Moving magnetoencephalography towards real-world applications with a wearable system." Nature, 555(7698), 657-661 (2018).

Sander, T.H., Preusser, J., Mhaskar, R., Kitching, J., Trahms, L., and Knappe, S., "Magnetoencephalography with a chip-scale atomic magnetometer." Biomedical Optics Express 3, (5), 981-990 (2012).

Borna, A, Carter, T.R., Colombo, A.P., Jau, Y.Y., McKay, J., Weisend, M., Taulu, S., Stephen, J.M., and Schwindt, P.D., "Non-invasive functional-brain-imaging with an OPM-based magnetoencephalography system." Plos one 15 (1), (2020).

Kitching, J., Knappe, S., Gerginov, V., Shah, V., Schwindt, P.D., Lindseth, B., Donley E.A., "Chip-scale atomic devices: precision atomic instruments based on MEMS." In Frequency Standards And Metrology, 445-453 (2009).

Kitching, J., Knappe, S. and Donley, E.A., "Atomic sensors—a review." IEEE Sensors Journal, 11(9), 1749-1758 (2011).

Budker, D. and Romalis, M., "Optical magnetometry". Nature physics, 3(4), 227-234 (2007).

Dupont-Roc, J., Haroche, S. & Cohen-Tannoudji, C., "Detection of very weak magnetic fields (10-9 gauss) by Rb zero-field level crossing resonances", Phys. Lett. A 28, 638-639 (1969).

Happer, W., "Optical pumping", Rev. Mod. Phys., 44 (2), 169-249 (1972).

Purcell, E.M., Field, G.B., "Influence of collisions upon population of hyperfine states in hydrogen", Astrophys. J., 124, 542 (1956).

Kominis, I.K., Kornack, T.W., Allred, J.C. and Romalis, M.V., "A subfemtotesla multichannel atomic magnetometer." Nature, 422(6932), 596-599 (2003).

Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).

Bloom, A. L., "Principles of operation of the rubidium vapor magnetometer." Applied Optics 1(1), 61-68 (1962).

Bell, W.E., and Bloom, A.L., "Optically driven spin precession." Physical Review Letters 6, (6), 280 (1961).

Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).

Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).

De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).

Mellinger, J., Schalk, G., Braun, C., Preissl, H., Rosenstiel, W., Birbaumer, N. and Kübler, A., "An MEG-based brain—computer interface (BCI)." Neuroimage, 36(3), 581-593 (2007).

Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).

Lightfoot, G., "Summary of the N1-P2 cortical auditory evoked potential to estimate the auditory threshold in adults". Seminars in hearing, 37(1), 1 (2016).

Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).

Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).

Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).

Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multichannel magnetoencephalography." NeuroImage, 199, 598-608 (2019).

Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).

Iivanainen, J., Stenroos, M. and Parkkonen, L., "Measuring MEG closer to the brain: Performance of on-scalp sensor arrays." NeuroImage 147, 542-553 (2017).

Allred, J, C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett. 105, 070801—Published Aug. 12, 2010.

Barbieri, F., Trauchessec, V. Caruso, L. Trejo-Rosillo, J. Telenczuk, B. Paul E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Barna, Yuan-Yu Jau, Cort N. Johnson, Amber L. Dagel, and Peter D. D. Schwindt, "Four-channel optically pumped atomic magnetometer for magnetoencephalography," Opt Express 24, 15403-15416(2016).

Dang, H.B. & Maloof, AC. & Romalis, Michael. (2009). Ultra-high sensitivity magnetic field and magnetization measurements with an atomic magnetometer. Applied Physics Letters. 97.10.1063/1. 3491215.

Donley, E.A. & Hodby, E & Hollberg, L & Kitching, J. (2007). Demonstration of high-performance compact magnetic shields for chip-scale atomic devices. The Review of scientific instruments. 78.083102.

Hamalainen, Matti & Ritta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2.413-497.

(56) References Cited

OTHER PUBLICATIONS

Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (1 O).ISSN 2331-7019.

Jimenez-Martinez, R., Griffth, W.C., Wang, Y.J., Knappe, S., Kitching, J., Smith, K, & Prouty, M.D. (2010). Sensitivity comparison of Mix and frequency-modulated bell-bloom Cs magnetometers in a microfabricated cell. IEEE Transactions on Instrumentation and Measurement, 59(2), 372-378.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.10071978-3-642-33045-2_ 49.

Korth, H., K. Strohbehn, F. Tejada, A.G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi: 10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. I., Hodges, J. S., Hong, S., Taylor, J.M., Cappellaro, P., . . . & Yacoby, A. (2008). Nanoscale magnetic sensing with an individual electronic spin in diamond. Nature, 455(7213), 644.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, s. J., and Romalis, M.V., "Unshielded three-axis vector operation of a spin-exchange-relaxation-free atomic magnetometer." Applied physics letters 85.20 (2004): 4804-4806.

Matti S. Hämäläinen, "Magnetoencephalography: A Tool For Functional Brain Imaging", Brain Topography, vol. 5. No. 2. 1992; 8 pages.

Martin W. Hess and Peter Benner, "Fast Evaluation of Time-Harmonic Maxwell's Equations Using the Reduced Basis Method", IEEE Transactions on Microwave Theory and Techniques, vol. 61, No. 6, Jun. 2013; 10 pages.

Dipankar Sarkar and N. J. Halas, "General vector basis function solution of Maxwell's equations", Physical Review E, vol. 56, No. I, Jul. 1997; 11 pages.

M. Ortner, A. Nehorai, and H. Preissl, "A spatial point process model for solving the MEG inverse problem", Washington University in St. Louis, St. Louis, Missouri, USA, University of Arkansas for Medical Sciences, Little Rock, Arkansas, USA, University of Tuebingen, Tuebingen, Germany; ELSEVIER; International Congress Series I300 (2007) 253-256; 4 pages.

Non-Final Office Action for U.S. Appl. No. 17/160,179 dated Dec. 5, 2022 38 pages.

Amendment and Response for U.S. Appl. No. 17/160,179, filed Jan. 3, 2023 26 pages.

Restriction Requirement for U.S. Appl. No. 17/160,152 dated Dec. 5, 2022 8 pages.

Response to Election/Restriction Requirement filed for U.S. Appl. No. 17/160,152 dated Dec. 14, 2022 1 page.

Kiwoong Kim, Samo Begus, Hui Xia, Seung-Kyun lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014. pdf.

Sheng, Dong & R. Perry, Abigail & Krzyzewski, Sean & Geller, Shawn & Kitching, John & Knappe, Svenja. (2017). A microfabricated optically-pumped magnatic gradiometer. Applied Physics Letters. 110. 10.1063/1.4974349.

Sheng, Dehong & Li, S & Dural, Nezih & Romalis, Michael. (2013). Subfemtotesla Scalar Atomic Magoetometoy Using Multipass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J. 2012. In situ triaxial magnetic field compensation for the spin-exchange-relaxation-free atomic magnetometer. Review of Scientific Instruments, 83(10), p. 103104.

Joan Lee, Hyun & Shim, Jeong & Moon, Han Seb & Kim, Kiwoong. (2014). Flat-response spin-exchange relaxation free atomic magnetometer under negative feedback. Optics Express. 22. 10.1364/0E.22.019887.

Griffith, Clark & Jimenez-Martinez, Ricardo & Shah, Vishal & Knappe, SvenJa & Kitching, John. (2009). Miniature atomic magnetometer integrated with flux concentrators. Applied Physics Letters—Appl Phys Lett. 94. 10.105311.2885711.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.3056152.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-X.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martinez, Dong Sheng, John LeBlanc, Lutz Trahms, Tilmann Sander, John Kitching, and Svenja Knappe, "Magnetic field imaging with microfabricated optically-pumped magnetometers," Opt Express 25, 7849-7858 (2017).

Slocum et al., Self-Calibrating Vector Magnetometer for Space, https:l/esto.nasa.gov/conferences/estc-2002/Papers/B3P4(Slocum).pdf.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

R.E. Slocum & L.J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/A0.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

Larry J. Ryan, Robert E. Slocum, and Robert B. Steves, Miniature Vector Laser Magnetometer Measurements of Earth's Field, May 10, 2004, 4 pgs.

Lorenz, V.O., Dai, X., Green, H., Asnicar, T.R., & Cundiff, S.T. (2008). High-density, high temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zoloterev, Max. (2016). Magnetic shielding and exotic spin-dependent interactions. Physical Review D. 94. 10.1103/PhysRevD.94.082005.

Huang, Haichao, et al. "Single-beam three axis atomic magnetometer." Applied Physics Letters 109.6 (2016): 062404. (Year:2016).

(56) References Cited

OTHER PUBLICATIONS

Scott Jeffrey Seltzer: "Developments in Alkali-Metal Atomic Magnetometry", Nov. 2008 (Nov. 1, 2008 ), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

\* cited by examiner

SELF-CALIBRATION OF FLUX GATE OFFSET AND GAIN DRIFT TO IMPROVE MEASUREMENT ACCURACY OF MAGNETIC FIELDS FROM THE BRAIN USING A WEARABLE NEURAL DETECTION SYSTEM

RELATED APPLICATION DATA

Pursuant to 35 U.S.C. § 119(e), this application claims the benefit of U.S. Provisional Patent Application 62/975,709, filed Feb. 12, 2020, and U.S. Provisional Patent Application 63/035,629, filed Jun. 5, 2020, which are expressly incorporated herein by reference.

FIELD OF THE INVENTION

The present inventions relate to methods and systems for non-invasive measurements from the human body, and in particular, methods and systems related to detecting physiological activity from the human brain, animal brain, and/or peripheral nerves.

BACKGROUND OF THE INVENTION

Measuring neural activity in the brain is useful for medical diagnostics, neuromodulation therapies, neuroengineering, and brain-computer interfacing. Conventional methods for measuring neural activity in the brain include X-Ray Computed Tomography (CT) scans, positron emission tomography (PET), functional magnetic resonance imaging (fMRI), or other methods that are large, expensive, require dedicated rooms in hospitals and clinics, and are not wearable or convenient to use.

In contrast to these techniques, one promising technique for measuring neural activity in the brain is magnetoencephalography (MEG), which is capable of non-invasively detecting neural activity in the brain without potentially harmful ionizing radiation, and without use of heavy or large equipment. Thus, MEG-based neural activity measurement systems can be scaled to wearable or portable form factors, which is especially important in brain-computer interface (BCI) applications that require subjects to interact freely within their environment. MEG operates under the principle that time-varying electrical current within activated neurons inherently generate magnetic signals in the form of a magnetic field that can be detected by very sensitive magnetometers located around the head.

Measuring the small magnetic fields emanating from the brain, and doing so non-invasively (without surgically penetrating the skin and bone of the head) and doing so with high spatial and temporal resolution, is difficult. The magnetic fields produced by the brain are small, and they are smaller still by the time they propagate out past the skull and the skin surface of the head. In comparison, the magnetic field emitted from various outside magnetic sources in the environment, including from global sources, such as the Earth's magnetic field, and from localized sources, such as electrical outlets and sockets, electrical wires or connections in the wall, and everyday electrical equipment in a home, office, or laboratory setting, far exceed the strength of the magnetic signals generated in the brain by many orders of magnitude, and has a distribution in space and time that is not known a-priori. Hence, it is a difficult challenge to extract the small desired signal from the brain, and to discriminate it from much larger unwanted magnetic field signals from the rest of the user's natural environment.

One type of system that can be used for MEG is a Superconductive Quantum Interference Device (SQUID), which is sensitive enough to measure magnetic fields as small as $5 \times 10^{-18}$ Tesla, which can be compared to magnetic fields resulting from physiological processes in animals, which may be in the range of $10^{-9}$ to $10^{-6}$ Tesla. However, SQUIDs rely on superconducting loops, and thus require cryogenic cooling, which may make it prohibitively costly and too large to be incorporated into a wearable or portable form factor. Thus, neural activity measurement systems that utilize SQUIDs may not be appropriate for BCI applications.

Optically pumped magnetometers (OPMs) have emerged as a viable and wearable alternative to cryogenic, superconducting, SQUID-based MEG systems, and have an advantage of obviating the need for cryogenic cooling, and as a result, may be flexibly placed on any part of the body, including around the head, which is especially important for BCI applications. Because cryogenic cooling is not required, OPMs may be placed within millimeters of the scalp, thereby enabling measurement of a larger signal from the brain (brain signals dissipate with distance), especially for sources of magnetic signals at shallow depths beneath the skull, as well as providing consistency across different head shapes and sizes.

OPMs optically pump a sample (usually a vapor formed of one of the alkali metals (e.g., rubidium, cesium, or potassium) due to their simple atomic structure, low melting point, and ease of pumping with readily available lasers) with circularly polarized light at a precisely defined frequency, thereby transferring polarized light to the vapor, and producing a large macroscopic polarization in the vapor in the direction of the light (i.e., the alkali metal atoms in the vapor will all have spins that are oriented in the direction of the light) that induces a magnetically sensitive state in the vapor. Once this magnetically sensitive state is established, polarized light is no longer transferred to the vapor, but instead, passes transparently through the vapor. In the presence of an ambient magnetic field, the spin orientation (or precession) of the alkali metal atoms in the optically pumped vapor will uniformly change, thereby disrupting the magnetically sensitive state, which is then subsequently reestablished by the transfer of the polarized light to the vapor. Because the transmission of light through the vapor varies as the spin precession of the alkali metal atoms in the vapor (and thus the magnetically sensitive state) changes in response to changes in the ambient magnetic field, the transmission of light (either the pumping light or a separate probe light) through the vapor represents a magnetic field-dependent signal (i.e., a MEG signal) that may be detected, thereby providing a measure of magnitude changes in the magnetic field.

To maintain the magnetically sensitive state of the vapor, it is important that spin relaxation due to spin exchange collisions be suppressed. In low magnetic fields (<10 nT), spin relaxation due to spin exchange collisions can be suppressed greatly, and thus, some OPMs are operated as zero-field magnetometers or Spin Exchange Relaxation Free (SERF) OPMs (referred to as "SERF OPMs"), thereby allowing for very high magnetometer sensitivities. Furthermore, because OPM measurements can be quite sensitive to low-frequency noise, the polarization of the vapor may be modulated to move the MEG signal away from the low-frequency end of the spectrum. SERF OPMs typically amplitude modulate the vapor polarization using magnetic coils that generate oscillating magnetic fields that vary at a frequency (e.g., 2000 Hz) much greater than the relaxation rate of the vapor (approximately 100 Hz). The amplitude modulated MEG signal can then be demodulated using lock-in detection to recover the MEG signal.

Although SERF OPMs allow for very high magnetometer sensitivities, they have a small dynamic range and bandwidth compared to SQUIDs, and can thus only operate in small magnetic fields (tens of nT, and often lower, to stay in the linear range of the OPMs). This becomes problematic when attempting to detect a very weak neural activity-induced magnetic field from the brain against an outside magnetic field.

For example, referring to FIG. 1, the magnitude of the magnetic field generated by a human brain (i.e., the MEG signal) may range from below 5 fT to just below 1 pT, while the magnitude of the outside magnetic field, including the Earth's magnetic field, may range from just above 5 μT to 100 μT. It should be appreciated that Earth's magnetic field covers a large range as it depends on the position of the Earth, as well as the materials of the surrounding environment where the magnetic field is measured. There are also magnetic fields from electrical power lines, everyday electric objects (microwaves, fridges, cell phones), and their interaction with magnetizable objects (metal chair legs, tables, metal posts, wall rebar, etc.). In the United States these magnetic fields appear at 60 Hz and its harmonics (120 Hz, 180 Hz, etc.) and can range in amplitude from about 500 nT to below 10 nT. In Europe electrical power is at 50 Hz, with harmonics at 100 Hz, 150 Hz, etc., and similar magnitudes.

The approximate operating range of a SERF OPM (i.e., the range in which the metallic alkali vapor resonates) extends from below 1 fT up to 200 nT. Outside of this range, the metallic alkali vapor in the OPM loses sensitivity to magnetic fields. In contrast, the approximate operating range of a less sensitive sensor, such as a flux gate magnetometer, extends from around 100 fT to close to 100 μT. Thus, in contrast to flux gate magnetometers, the limited dynamic range of a SERF OPM presents a challenge in measuring signals having a high dynamic range, e.g., approximately $2 \times 10^{10}$, which corresponds to the ratio of the lower range magnitude of the MEG signal (approximately 5 fT) to the higher range magnitude of the outside magnetic field (approximately 100 μT).

Thus, to take advantage of SERF OPMs for MEG, the outside magnetic field must be suppressed to near-zero. Otherwise, the SERF OPM cannot operate. One conventional technique for suppressing the outside magnetic field involves using large, immobile, and expensive magnetically shielded rooms to passively isolate the SERF OPMs from the sources of the outside magnetic field, effectively reducing the dynamic range requirements of the SERF OPMs used to measure the weak MEG signals. These shielded rooms, however, are generally not viable for the consumer market, especially with regard to BCI applications, where it desirable that the MEG-based neural activity measurement system be incorporated into a wearable or portable form factor. Thus, for BCI applications, SERF OPMs must be capable of operating in the ambient background magnetic field of the native environment, including the Earth's magnetic field and other local sources of magnetic fields.

Another technique for suppressing the outside magnetic field without using magnetically shielded rooms involves incorporating a direct broadband feedback control system to actively null the outside magnetic field at the SERF OPM. In this case, the system actuators attempt to cancel the entire bandwidth of the outside magnetic field by applying a noise-cancelling, broadband, magnetic field to the sensors. However, such feedback control for OPM systems has not been implemented in a wearable system.

There, thus, remains a need to provide means for more effectively suppressing an outside magnetic field in a wearable neural detection system.

SUMMARY OF THE INVENTION

In accordance with a first aspect of the present inventions, a calibration system for a magnetometer having an unknown gain is provided. The calibration system comprises at least one calibration coil affixed relative to the magnetometer, and at least one driver configured for actuating the calibration coil(s) at a known actuation strength and at a calibration frequency, such that the calibration coil(s) generates a calibrating magnetic field of a known amplitude at the magnetometer. In one embodiment, the driver(s) is configured for actuating the calibration coil(s) at a known actuation strength by supplying electrical current at a known amplitude to the calibration coil(s).

The calibration system further comprises at least one processor configured for acquiring a measurement of the calibrating magnetic field reported by the magnetometer, computing a ratio of an amplitude of the acquired calibrating magnetic field measurement reported by the magnetometer and the known amplitude of the calibrating magnetic field at the magnetometer, and determining the unknown gain of the magnetometer at least partially based on computed ratio. The processor(s) may be configured for outputting at least one control signal respectively to the driver(s) defining the known actuation strength.

In one embodiment, the magnetometer is a vector magnetometer comprising a plurality of scalar magnetometers having a plurality of unknown gains, and the calibration coil(s) is oriented relative to the plurality of scalar magnetometers of the vector magnetometer, such that the calibrating magnetic field generated by the calibration coil(s) has a plurality of directional components of known amplitudes at the plurality of scalar magnetometers of the vector magnetometer, and the acquired calibrating magnetic field measurement reported by the magnetometer comprises an acquired plurality of directional components of the calibrating magnetic field measurement reported by the plurality of scalar magnetometers of the vector magnetometer. The plurality of scalar magnetometers of the vector magnetometer may be oriented mutually orthogonal to each other, such that the plurality of directional components of the calibrating magnetic field at the plurality of scalar magnetometers of the vector magnetometer are mutually orthogonal to each other, and the acquired plurality of directional component measurements of the calibrating magnetic field reported by the plurality of scalar magnetometers of the vector magnetometer are mutually orthogonal to each other.

In this embodiment, the processor(s) is configured for computing the ratio of the amplitude of the acquired calibrating magnetic field measurement reported by the magnetometer and the known amplitude of the calibrating magnetic field at the magnetometer by computing a plurality of ratios between the acquired plurality of directional component measurements of the calibrating magnetic field reported by the plurality of scalar magnetometers of the vector magnetometer and the known amplitudes of the plurality of directional components of the calibrating magnetic field generated by the calibration coil(s) at the plurality of scalar magnetometers of the vector magnetometer. The processor(s) is further configured for determining the unknown gain of the magnetometer by determining the plurality of unknown gains of the plurality of scalar magnetometers of the vector magnetometer at least partially based on computed plurality of ratios.

In another embodiment, the calibration frequency is outside of the linear operating range of the magnetometer, and the determined gain of the magnetometer is at a reference frequency within the linear operating range of the magnetometer. In this case, the calibration system may further comprise memory storing a roll-off gain error of the magnetometer characterizing roll-off effects of the gain of the magnetometer at the reference frequency and the gain of the magnetometer at the calibration frequency, and the processor(s) may be configured for recalling the roll-off gain error of the magnetometer from the memory, computing a product of the known amplitude of the calibrating magnetic field at the magnetometer and the recalled roll-off gain error of the magnetometer. In this case, the computed ratio is between the amplitude of the acquired calibrating magnetic field measurement reported by the magnetometer and the computed product. The memory may further store a gain of the calibration coil(s) at the calibration frequency, and the processor may be configured for recalling the gain of the calibration coil(s) from the memory, computing a product of the known actuation strength at which the calibration coil(s) is actuated and the recalled gain of the calibration coil(s), and determining the known amplitude of the calibrating magnetic field at the magnetometer at least partially based on the computed product.

In accordance with a second aspect of the present inventions, a signal acquisition unit comprises the magnetometer and calibration circuit described above. The magnetometer is configured for reporting a measurement of an arbitrary magnetic field, and the processor(s) is configured for computing a ratio between arbitrary magnetic field measurement reported by the magnetometer and gain of the magnetometer, and determining an amplitude of the arbitrary magnetic field at the magnetometer at least partially based on the computed ratio.

In one embodiment, the signal acquisition unit may further comprise memory storing a gain offset of the magnetometer, in which case, the processor(s) may be configured for computing the difference between the computed ratio and the inherent gain offset of the magnetometer, and determining the amplitude of the arbitrary magnetic field at the magnetometer at least partially based on the computed difference.

In another embodiment, the signal acquisition unit further comprises at least one magnetic field actuator configured for generating an actuated magnetic field that at least partially cancels an outside magnetic field, thereby yielding a total residual magnetic field at the magnetometer as the arbitrary magnetic field, such that the arbitrary magnetic field measurement reported by the magnetometer is a total residual magnetic field measurement reported by the magnetometer, and the determined amplitude of the arbitrary magnetic field at the magnetometer is a determined amplitude of the total residual magnetic field at the magnetometer. In this case, the processor(s) may be configured for controlling the actuated magnetic field at least partially based on the total residual magnetic field determined at the magnetometer in a manner that suppresses the total residual magnetic field. The magnetometer may be a coarse magnetometer (e.g., a flux gate magnetometer), such that the total residual magnetic field measurement reported by the coarse magnetometer is a coarse total residual magnetic field measurement, and the signal acquisition unit may further comprise a fine magnetometer (e.g., an optically pumped magnetometer (OPM)) configured for reporting a fine measurement of the suppressed total residual magnetic field. The signal acquisition unit may be configured for being worn on a head of a user. In this case, the signal acquisition unit may comprise a support structure to which the coarse magnetometer, fine magnetometer, and calibration coil(s) is affixed. The total residual magnetic field may comprise a magnetoencephalography (MEG) magnetic field, and the processor(s) may be further configured for deriving a MEG signal from the fine total residual magnetic field measurement reported by the fine magnetometer.

In accordance with a third aspect of the present inventions, a neural activity measurement system comprises the signal acquisition unit described above, and a signal processing unit configured for determining an existence of neural activity in the brain of the user based on the derived MEG signal.

In accordance with a fourth aspect of the present inventions, a calibration method for a magnetometer having an unknown gain is provided. The method comprises generating a calibrating magnetic field at a calibration frequency of a known amplitude at the magnetometer and reporting a measurement of the calibrating magnetic field by the magnetometer.

The method further comprises computing a ratio of an amplitude of the calibrating magnetic field measurement reported by the magnetometer and the known amplitude of the calibrating magnetic field at the magnetometer, and determining the unknown gain of the magnetometer at least partially based on computed ratio.

In one calibration method, the magnetometer is a vector magnetometer comprising a plurality of scalar magnetometers having a plurality of unknown gains, such that the calibrating magnetic field has a plurality of directional components of known amplitudes at the plurality of scalar magnetometers of the vector magnetometer, and the calibrating magnetic field measurement reported by the magnetometer comprises a plurality of directional components of the calibrating magnetic field measurement reported by the plurality of scalar magnetometers of the vector magnetometer. The plurality of scalar magnetometers of the vector magnetometer may be oriented mutually orthogonal to each other, such that the plurality of directional components of the calibrating magnetic field at the plurality of scalar magnetometers of the vector magnetometer are mutually orthogonal to each other, and the plurality of directional component measurements of the calibrating magnetic field reported by the plurality of scalar magnetometers of the vector magnetometer may be mutually orthogonal to each other.

In this calibration method, computing the ratio of the amplitude of the calibrating magnetic field measurement reported by the magnetometer and the known amplitude of the calibrating magnetic field at the magnetometer comprises computing a plurality of ratios between the plurality of directional component measurements of the calibrating magnetic field reported by the plurality of scalar magnetometers of the vector magnetometer and the known amplitudes of the plurality of directional components of the calibrating magnetic field at the plurality of scalar magnetometers of the vector magnetometer. Determining the unknown gain of the magnetometer comprises determining the plurality of unknown gains of the plurality of scalar magnetometers of the vector magnetometer at least partially based on computed plurality of ratios.

In another calibration method, the calibrating magnetic field has a calibration frequency outside of the linear operating range of the magnetometer, and the determined gain of the magnetometer is at a reference frequency within the linear operating range of the magnetometer. In this case, the calibration method may further comprise computing a product of the known amplitude of the calibrating magnetic field at the magnetometer and a roll-off gain error of the magnetometer characterizing roll-off effects of the gain of the magnetometer at the reference frequency and the gain of the magnetometer at the calibration frequency. The computed ratio may be between the amplitude of the acquired calibrating magnetic field measurement reported by the magnetometer and the computed product. The calibrating magnetic field of a known amplitude at the magnetometer may be generated by actuating the at least one calibration coil at a known actuation strength, and the calibration method may further comprise computing a product of the known actuation strength at which the at least one calibration coil is actuated and a gain of the at least one calibration coil at the calibration frequency, and determining the known amplitude of the calibrating magnetic field at the magnetometer at least partially based on the computed product.

In accordance with a fifth aspect of the present inventions, a signal acquisition method comprises performing the calibration method described above, reporting a measurement of an arbitrary magnetic field by the magnetometer, computing a ratio between arbitrary magnetic field measurement reported by the magnetometer and gain of the magnetometer, and determining an amplitude of the arbitrary magnetic field at the magnetometer at least partially based on the computed ratio. The signal acquisition method may further comprise computing the difference between the computed ratio and a gain offset of the magnetometer, and determining the amplitude of the arbitrary magnetic field at the magnetometer at least partially based on the computed difference.

The signal acquisition method may further comprise generating an actuated magnetic field that at least partially cancels an outside magnetic field, thereby yielding a total residual magnetic field at the magnetometer as the arbitrary magnetic field, such that the arbitrary magnetic field measurement reported by the magnetometer is a total residual magnetic field measurement reported by the magnetometer, and the determined amplitude of the arbitrary magnetic field at the magnetometer is a determined amplitude of the total residual magnetic field at the magnetometer. This signal acquisition method may further comprise controlling the actuated magnetic field at least partially based on the total residual magnetic field determined at the magnetometer in a manner that suppresses the total residual magnetic field. The magnetometer may be a coarse magnetometer (e.g., a flux gate magnetometer), such that the total residual magnetic field measurement reported by the coarse magnetometer is a coarse total residual magnetic field measurement. In this case, the method may further comprise reporting a fine measurement of the suppressed total residual magnetic field. The total residual magnetic field may comprise a magnetoencephalography (MEG) magnetic field emanating from a person, in which case, the method may further comprise deriving a MEG signal from the reported fine total residual magnetic field measurement reported.

In accordance with a sixth aspect of the present inventions, a neural activity measurement method comprises performing the signal acquisition method described above, and determining an existence of neural activity in the brain of the user based on the derived MEG signal.

In accordance with a seventh aspect of the present inventions, a pre-calibration system for a calibration-enabled magnetometer assembly comprising a magnetometer (e.g., a flux gate magnetometer) having a linear operating range and at least one calibration coil is provided. In one embodiment, the pre-calibration system further a test fixture to which the calibration-enabled magnetometer assembly is affixed. The pre-calibration system further comprises at least one pre-calibration coil (e.g., a Helmholtz coil) and at least one driver.

The pre-calibration system further comprises a computing device configured for directing the driver(s) to actuate the pre-calibration coil(s) at a first actuation strength and at a reference frequency within the linear operating range of the magnetometer, such that the pre-calibration coil(s) generates a first magnetic field at the magnetometer, and acquiring a measurement of the first magnetic field reported by the magnetometer, and directing the driver(s) to actuate the pre-calibration coil(s) at a second actuation strength (which may be the same as the first actuation strength) and at a calibration frequency outside the linear operating range of the magnetometer, such that the pre-calibration coil(s) generates a second magnetic field at the magnetometer. The computing device is further configured for acquiring a measurement of the second magnetic field reported by the magnetometer, computing a first ratio between an amplitude of the acquired first magnetic field measurement reported by the magnetometer and an amplitude of the acquired second magnetic field measurement reported by the magnetometer, and determining a roll-off gain error of the magnetometer at least partially based on the first computed ratio. The roll-off gain error characterizes roll-off effects of the gain of the magnetometer at the reference frequency and the gain of the magnetometer at the calibration frequency.

In one embodiment, the calibration coil(s) of the calibration-enabled magnetometer assembly has an unknown gain, in which case, the computing device may direct the driver(s) to actuate the calibration coil(s) of the calibration-enabled magnetometer assembly at a third actuation strength (which may be the same as the second actuation strength) and at the calibration frequency, such that the calibration coil(s) generates a third magnetic field at the magnetometer. In this embodiment, the computing device is further configured for acquiring a measurement of the third magnetic field reported by the magnetometer, computing a second ratio between an amplitude of the acquired second magnetic field measurement reported by the magnetometer and an amplitude of the acquired third magnetic field measurement reported by the magnetometer, and determining the unknown gain of the at least one calibration coil of the calibration-enabled magnetometer assembly based on the second computed ratio. The pre-calibration coil(s) may have a known gain, in which case, the processor(s) may be configured for computing a product of the amplitude of the acquired second magnetic field measurement reported by the magnetometer and the known gain of the pre-calibration coil(s). The second computed ratio may be between the computed product and the amplitude of the acquired third magnetic field measurement reported by the magnetometer.

In another embodiment, the magnetometer is a vector magnetometer comprising a plurality of scalar magnetometers, and the pre-calibration coil(s) is oriented relative to the plurality of scalar magnetometers of the vector magnetometer, such that the first magnetic field generated by the pre-calibration coil(s) has a plurality of directional components of known amplitudes at the plurality of scalar magnetometers of the vector magnetometer. The second magnetic field generated by the pre-calibration coil(s) has a plurality of directional components of known amplitudes at the plurality of scalar magnetometers of the vector magnetometer. The acquired first magnetic field measurement reported by the magnetometer comprises an acquired plurality of directional components of the first magnetic field measurement reported by the plurality of scalar magnetometers of the vector magnetometer, and the acquired second magnetic field measurement reported by the magnetometer comprises an acquired plurality of directional components of the second magnetic field measurement reported by the plurality of scalar magnetometers of the vector magnetometer. The computing device is configured for computing the first ratio of the amplitude of the acquired calibrating magnetic field measurement reported by the magnetometer and the known amplitude of the calibrating magnetic field at the magnetometer by computing a first plurality of ratios between amplitudes of the acquired plurality of directional component measurements of the first magnetic field reported by the plurality of scalar magnetometers of the vector magnetometer and amplitudes of the acquired plurality of directional component measurements of the second magnetic field reported by the plurality of scalar components of the vector magnetometer. The computing device is further configured for determining the roll-off gain error of the magnetometer by determining a plurality of roll-off gain errors of the plurality of scalar magnetometers of the vector magnetometer at least partially based on the computed first plurality of ratios. The plurality of roll-off gain errors characterize roll-off effects of the plurality of gains of the plurality of scalar magnetometers of the vector magnetometer at the reference frequency and the plurality of gains of the plurality of scalar magnetometers of the vector magnetometer at the calibration frequency.

In this embodiment, the plurality of scalar magnetometers of the vector magnetometer may be oriented mutually orthogonal to each other, such that the plurality of directional components of the first magnetic field at the plurality of scalar magnetometers of the vector magnetometer are mutually orthogonal to each other, the plurality of directional components of the second magnetic field at the plurality of scalar magnetometers of the vector magnetometer are mutually orthogonal to each other, the acquired plurality of directional component measurements of the first magnetic field reported by the plurality of scalar magnetometers of the vector magnetometer are mutually orthogonal to each other, and the acquired plurality of directional component measurements of the second magnetic field reported by the plurality of scalar magnetometers of the vector magnetometer are mutually orthogonal to each other.

In accordance with an eighth aspect of the present inventions, a pre-calibration method for a calibration-enabled magnetometer assembly comprising a magnetometer (e.g., a flux gate magnetometer) having a linear operating range and at least one calibration coil is provided.

The pre-calibration method comprises actuating at least one pre-calibration coil (e.g., a Helmholtz coil) at a reference frequency within the linear operating range of the magnetometer, such that the pre-calibration coil(s) generates a first magnetic field reporting a measurement of the first magnetic field by the magnetometer, and actuating at least one pre-calibration coil at a second actuation strength (which may be the same as the first actuation strength) and at a calibration frequency outside the linear operating range of the magnetometer, such that the pre-calibration coil(s) generates a first magnetic field. The pre-calibration method further comprises reporting a measurement of the second magnetic field by the magnetometer, computing a first ratio between an amplitude of the first magnetic field measurement reported by the magnetometer and an amplitude of the second magnetic field measurement reported by the magnetometer, and determining a roll-off gain error of the magnetometer at least partially based on the first computed ratio. The roll-off gain error characterizes roll-off effects of the gain of the magnetometer at the reference frequency and the gain of the magnetometer at the calibration frequency.

In one pre-calibration method, the calibration coil(s) has an unknown gain, in which case, the method may further comprise actuating the calibration coil(s) of the calibration-enabled magnetometer assembly at a third actuation strength (which may be the same as the second actuation strength) at the calibration frequency, such that the calibration coil(s) generates a third magnetic field, reporting a measurement of the third magnetic field by the magnetometer, computing a second ratio between an amplitude of the second magnetic field measurement reported by the magnetometer and an amplitude of the third magnetic field measurement reported by the magnetometer, and determining the unknown gain of the calibration coil(s) of the calibration-enabled magnetometer assembly based on the second computed ratio. The pre-calibration coil may have a known gain, in which case, the pre-calibration method may further comprise computing a product of the amplitude of the second magnetic field measurement reported by the magnetometer and the known gain of the at least one pre-calibration coil. The second computed ratio is between the computed product and the amplitude of the third magnetic field measurement reported by the magnetometer.

In another pre-calibration method, the magnetometer is a vector magnetometer comprising a plurality of scalar magnetometers, such that the first magnetic field generated by the pre-calibration coil comprises a plurality of directional components of known amplitudes at the plurality of scalar magnetometers of the vector magnetometer, the second magnetic field generated by the pre-calibration coil comprises a plurality of directional components of known amplitudes at the plurality of scalar magnetometers of the vector magnetometer, a plurality of measured directional components of the first magnetic field are reported by the plurality of scalar magnetometers of the vector magnetometer, and a plurality of measured directional components of the second magnetic field are reported by the plurality of scalar magnetometers of the vector magnetometer. In this case, computing the first ratio of the amplitude of the calibration magnetic field measurement reported by the magnetometer and the known amplitude of the calibrating magnetic field at the magnetometer may comprise computing a first plurality of ratios between amplitudes of the acquired plurality of directional component measurements of the first magnetic field reported by the plurality of scalar magnetometers of the vector magnetometer and amplitudes of the acquired plurality of directional component measurements of the second magnetic field reported by the plurality of scalar components of the vector magnetometer. Determining the roll-off gain error of the magnetometer may comprise determining a plurality of roll-off gain errors of the plurality of scalar magnetometers of the vector magnetometer at least partially based on the computed first plurality of ratios. The plurality of roll-off gain errors characterize roll-off effects of the plurality of gains of the plurality of scalar magnetometers of the vector magnetometer at the reference frequency and the plurality of gains of the plurality of scalar magnetometers of the vector magnetometer at the calibration frequency.

In this pre-calibration method, the plurality of scalar magnetometers of the vector magnetometer may be oriented mutually orthogonal to each other, such that the plurality of directional components of the first magnetic field at the plurality of scalar magnetometers of the vector magnetometer are mutually orthogonal to each other, the plurality of directional components of the second magnetic field at the plurality of scalar magnetometers of the vector magnetometer are mutually orthogonal to each other, the plurality of directional component measurements of the first magnetic field reported by the plurality of scalar magnetometers of the vector magnetometer are mutually orthogonal to each other, and the plurality of directional component measurements of the second magnetic field reported by the plurality of scalar magnetometers of the vector magnetometer are mutually orthogonal to each other.

In accordance with a ninth aspect of the present inventions, a pre-calibration system for a calibration-enabled magnetometer assembly comprising a magnetometer (e.g., a flux gate magnetometer) having a linear operating range and at least one calibration coil having an unknown gain is provided. In one embodiment, the pre-calibration system further comprises a test fixture to which the calibration-enabled magnetometer assembly is affixed. The pre-calibration system comprises at least one pre-calibration coil (e.g., a Helmholtz coil) and at least one driver.

The pre-calibration system further comprises a computing device configured for directing the driver(s) to actuate the pre-calibration coil(s) at a first actuation strength and at a calibration frequency outside the linear operating range of the magnetometer, such that the pre-calibration coil(s) generates a first magnetic field at the magnetometer. The computing device is further configured for acquiring a measurement of the first magnetic field reported by the magnetometer, directing the driver(s) to actuate the calibration coil(s) of the calibration-enabled magnetometer assembly at a second actuation strength (which may be the same as the first actuation strength) and at the calibration frequency, such that the calibration coil(s) generates a second magnetic field at the magnetometer. The computing device is further configured for acquiring a measurement of the second magnetic field reported by the magnetometer, computing a ratio between an amplitude of the acquired first magnetic field measurement reported by the magnetometer and an amplitude of the acquired second magnetic field measurement reported by the magnetometer, and determining the unknown gain of the calibration coil(s) of the calibration-enabled magnetometer assembly based on the computed ratio.

In one embodiment, the pre-calibration coil(s) has a known gain, and the processor(s) is configured for computing a product of the amplitude of the acquired first magnetic field measurement reported by the magnetometer and the known gain of the pre-calibration coil(s). The second computed ratio is between the computed product and the amplitude of the acquired second magnetic field measurement reported by the magnetometer.

In another embodiment, the calibration coil(s) of the calibration-enabled magnetometer assembly has a plurality of unknown gains, the magnetometer is a vector magnetometer comprising a plurality of scalar magnetometers, and the pre-calibration coil(s) and the calibration coil(s) of the calibration-enabled magnetometer assembly are oriented relative to the plurality of scalar magnetometers of the vector magnetometer, such that the first magnetic field generated by the pre-calibration coil(s) has a plurality of directional components of known amplitudes at the plurality of scalar magnetometers of the vector magnetometer, the second magnetic field generated by the calibration coil(s) of the calibration-enabled magnetometer assembly has a plurality of directional components of known amplitudes at the plurality of scalar magnetometers of the vector magnetometer, the acquired first magnetic field measurement reported by the magnetometer comprises an acquired plurality of directional components of the first magnetic field measurement reported by the plurality of scalar magnetometers of the vector magnetometer, and the acquired second magnetic field measurement reported by the magnetometer comprises an acquired plurality of directional components of the second magnetic field measurement reported by the plurality of scalar magnetometers of the vector magnetometer.

In this embodiment, the computing device is configured for computing the first ratio of the amplitude of the acquired calibration magnetic field measurement reported by the magnetometer and the known amplitude of the calibrating magnetic field at the magnetometer by computing a plurality of ratios between amplitudes of the acquired plurality of directional component measurements of the first magnetic field reported by the plurality of scalar magnetometers of the vector magnetometer and amplitudes of the acquired plurality of directional component measurements of the second magnetic field reported by the plurality of scalar components of the vector magnetometer. The computing device is further configured for determining the plurality of unknown gains of the coil(s) of the calibration-enabled magnetometer assembly at least partially based on the computed plurality of ratios.

In this case, the plurality of scalar magnetometers of the vector magnetometer may be oriented mutually orthogonal to each other, such that the plurality of directional components of the first magnetic field at the plurality of scalar magnetometers of the vector magnetometer are mutually orthogonal to each other, the plurality of directional components of the second magnetic field at the plurality of scalar magnetometers of the vector magnetometer are mutually orthogonal to each other, the acquired plurality of directional component measurements of the first magnetic field reported by the plurality of scalar magnetometers of the vector magnetometer are mutually orthogonal to each other, and the acquired plurality of directional component measurements of the second magnetic field reported by the plurality of scalar magnetometers of the vector magnetometer are mutually orthogonal to each other.

In accordance with a tenth aspect of the present inventions, a pre-calibration method for a calibration-enabled magnetometer assembly comprising a magnetometer (e.g., a flux gate magnetometer) having a linear operating range and at least one calibration coil (e.g., a Helmholtz coil) is provided. The pre-calibration method comprises actuating at least one pre-calibration coil at a calibration frequency outside the linear operating range of the magnetometer, such that the pre-calibration coil(s) generates a first magnetic field, actuating a first magnetic field at a first actuation strength and at a calibration frequency outside the linear operation range of the magnetometer, reporting a measurement of the first magnetic field by the magnetometer, actuating the calibration coil(s) of the calibration-enabled magnetometer assembly at a second actuation strength (which may be the same as the first actuation strength) at the calibration frequency, such that the calibration coil(s) generates a second magnetic field, and reporting a measurement of the second magnetic field by the magnetometer. The pre-calibration method further comprises computing at least one gain of the calibration coil(s) of the calibration-enabled magnetometer assembly based on a ratio between an amplitude of the first magnetic field measurement reported by the magnetometer and an amplitude of the second magnetic field measurement reported by the magnetometer.

In one pre-calibration method, the pre-calibration coil(s) has a known gain, in which case, the method comprises computing a product of the amplitude of the first magnetic field measurement reported by the magnetometer and the known gain of the pre-calibration coil(s), and computing the gain(s) of the calibration coil(s) of the calibration-enabled magnetometer assembly based on a ratio between the computed product and the amplitude of the second magnetic field measurement reported by the magnetometer.

In another pre-calibration method, the first magnetic field has a plurality of directional components, the second magnetic field has a plurality of directional components, the magnetometer is a vector magnetometer comprising a plurality of scalar magnetometers, reporting the first magnetic field measurement by the magnetometer comprises reporting measurements of the plurality of directional components of the first magnetic field by the plurality of scalar magnetometers of the vector magnetometer, reporting the second magnetic field measurement by the magnetometer comprises reporting measurements of the plurality of directional components of the second magnetic field by the plurality of scalar magnetometers of the vector magnetometer, and the gain(s) of the calibration coil(s) is computed based on a ratio between amplitudes of the plurality of directional components of the first magnetic field measurement reported by the plurality of scalar magnetometers of the vector magnetometer and amplitudes of the plurality of directional components of the second magnetic field measurement reported by the plurality of scalar components of the vector magnetometer.

In this method, the plurality of directional components of the first magnetic field may be mutually orthogonal to each other, the plurality of directional components of the second magnetic field may be mutually orthogonal to each other, the plurality of directional component measurements of the first magnetic field reported by the plurality of scalar magnetometers of the vector magnetometer may be mutually orthogonal to each other, and the plurality of directional component measurements of the second magnetic field reported by the plurality of scalar magnetometers of the vector magnetometer may be mutually orthogonal to each other.

In accordance with an eleventh aspect of the present inventions, a pre-calibration system for at least three magnetometers (e.g., flux gate magnetometers), each having an inherent gain offset, is provided. In one embodiment, the magnetometers comprise three scalar magnetometers arranged as a vector magnetometer. The pre-calibration system comprises a test fixture configured for affixing the magnetometer relative to each other, such that the magnetometers are oriented in at least three different directions in three-dimensional space, and rotating the magnetometers through at least four three-dimensional vector angles. In one embodiment, test fixture is configured for affixing the magnetometers relative to each other in a substantially co-located arrangement.

The pre-calibration system further comprises at least one pre-calibration coil, and at least one driver configured for actuating the calibration coil(s), such that the calibration coil(s) generates a calibrating uniform magnetic field in the vicinity of the magnetometer while at the three-dimensional vector angles.

The pre-calibration system further comprises a computing device configured for acquiring measurements of the calibrating uniform magnetic field reported by the magnetometers at the three-dimensional vector angles. In one embodiment, the plurality of different directions in which the magnetometers are oriented are mutually orthogonal to each other, such that the calibrating uniform magnetic field measurements reported by the magnetometers are mutually orthogonal to each other. The computing device is further configured for determining the inherent gain offsets of the magnetometers based on the acquired calibrating uniform magnetic field measurements reported by the magnetometer at the three-dimensional vector angles.

In one embodiment, the computing device is configured for determining the inherent gain offsets of the magnetometers by fitting the inherent gain offsets to the acquired calibrating uniform magnetic field measurements reported by the magnetometers at the three-dimensional vector angles. For example, the computing device may be configured for fitting the inherent gain offsets to the acquired calibrating uniform magnetic field measurements reported by the magnetometers at the three-dimensional vector angles in accordance with the equation: $\|\vec{B}_J - \vec{B}_0\|^2 = B_{TRUE}^2$, where $\|\cdot\|^2$ denotes the squared norm of a vector; $\vec{B}_J$ is a vector representing the acquired calibrating uniform magnetic field measurements reported by each of the magnetometers at the three-dimensional vector angles; $\vec{B}_0$ is a vector representing the inherent gain offsets of the magnetometers; and $B_{TRUE}^2$ is the square of the calibrating uniform magnetic field.

In accordance with a twelfth aspect of the present inventions, a pre-calibration method for at least three magnetometers (e.g., flux gate magnetometers), each having an inherent gain offset. The pre-calibration method comprises affixing the magnetometers relative to each other, such that the magnetometers are oriented in at least three different directions. In one pre-calibration method, the magnetometers comprise three scalar magnetometers arranged as a vector magnetometer. In another pre-calibration method, the magnetometers are affixed relative to each other in a substantially co-located arrangement.

The method further comprises rotating the magnetometers through at least four three-dimensional vector angles, generating a calibrating uniform magnetic field in the vicinity of the magnetometers while at the three-dimensional vector angles, and reporting measurements of the calibrating uniform magnetic field by the magnetometers at the three-dimensional vector angles. In one pre-calibration method, the plurality of different directions in which the magnetometers are oriented are mutually orthogonal to each other, such that the calibrating uniform magnetic field measurements reported by the magnetometers are mutually orthogonal to each other. The pre-calibration method further comprises determining the inherent gain offsets of the magnetometers based on the calibrating uniform magnetic field measurements reported by the magnetometers at the three-dimensional vector angles.

In one pre-calibration method of claim, the inherent gain offsets of the magnetometers are fitted to the calibrating uniform magnetic field measurements reported by the magnetometers at the three-dimensional vector angles. For example, the inherent gain offsets of the magnetometers are fitted to the calibrating uniform magnetic field measurements reported by the magnetometers at the at least four three-dimensional vector angles in accordance with the equation: $\|\vec{B}_J - \vec{B}_0\|^2 = B_{TRUE}^2$ where $\|\cdot\|^2$ denotes the squared norm of a vector; $\vec{B}_J$ is a vector representing the acquired measurements of the calibrating uniform magnetic field reported by the magnetometers at each of the three-dimensional vector angles; $\vec{B}_0$ is a vector representing the inherent gain offsets of the magnetometers; and $B_{TRUE}^2$ is the square of the calibrating uniform magnetic field.

In accordance with thirteenth aspect of the present inventions, a calibration-enabled magnetometer assembly comprises a magnetometer, at least one calibration coil, and a fixture that carries the magnetometer and the coil(s) in proximity to each other. In one embodiment, the fixture has a rectangular geometry with six faces, and the calibration coil(s) is affixed to at least one of the six faces. In this case, the magnetometer may be, e.g., a vector magnetometer comprising a plurality of scalar magnetometers respectively affixed to a plurality of the six faces of the fixture. The calibration coil(s) may be oriented in a plurality of different directions, and affixed to a plurality of the six faces of the fixture. As one example, the calibration coil(s) may comprise a plurality of calibration coils respectively affixed to the plurality of faces of the fixture. As another example, the calibration coil(s) may comprise a single coil, such that a plurality of portions of the single coil are respectively affixed to the plurality of faces of the fixture. In this example, the plurality of portions of the single coil may be affixed to a single corner of the fixture. The plurality of different directions in which the calibration coil(s) is oriented may be mutually orthogonal to each other, and the plurality of faces to which the calibration coil(s) are affixed may be mutually orthogonal to each other. In another embodiment, the fixture is composed of a magnetically transparent material.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the present inventions and are not therefore to be considered limiting of its scope, the present inventions will be described and explained with additional specificity and detail through the use of the accompanying drawings in which.

DETAILED DESCRIPTION OF THE EMBODIMENTS

Significantly, the neural activity measurement systems (and variations thereof) described herein are configured for non-invasively acquiring magnetoencephalography (MEG) signals from a brain of a user while effectively suppressing an outside magnetic field without the use of magnetically shielded rooms, and identifying and localizing the neural activity within the cortical structures of the brain of the user based on the acquired magnetoencephalography (MEG) signals.

The neural activity measurement system described herein may take the form of a brain computer interface (BCI) (also known as a neural-controlled interface (NCI), mind-machine interface (MMI), direct neural interface (DNI), or brain-machine interface (BMI)), which converts the neural activity information into commands that are output to an external device or devices for carrying out desired actions that replace, restore, enhance, supplement, or improve natural central nervous system (CNS) output, and thereby changes the ongoing interactions between the CNS of a user and an external or internal environment.

Figure 3:
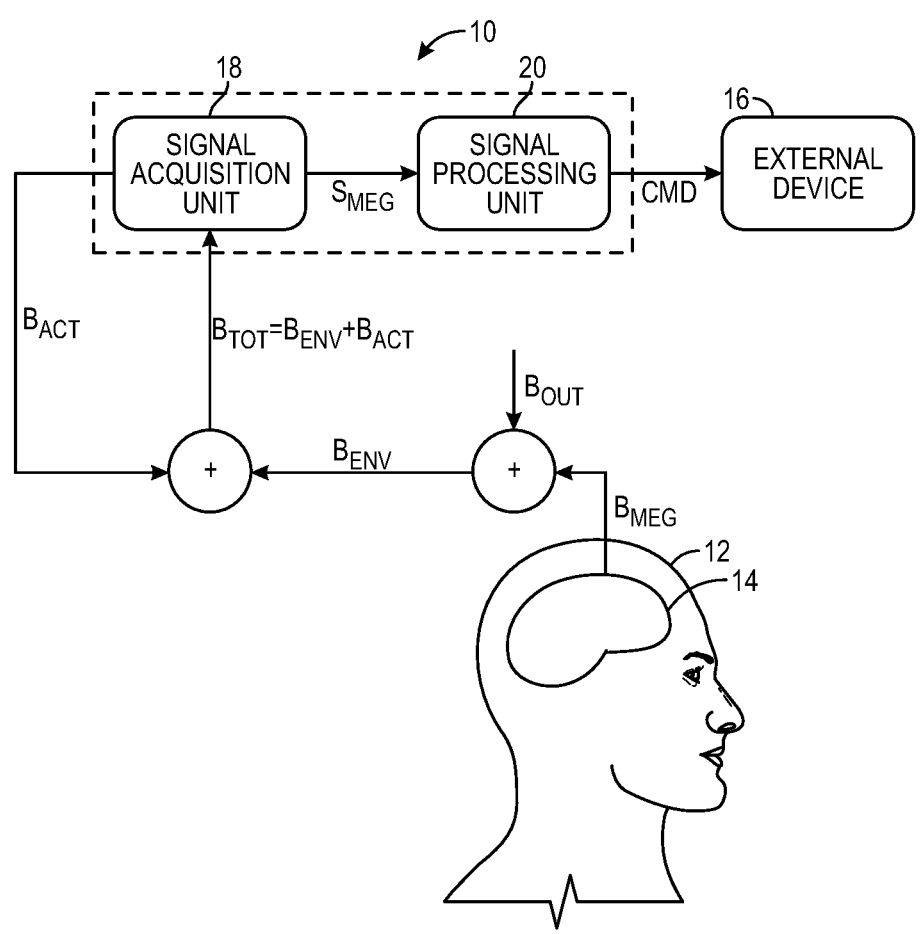
FIG. 3 is a block diagram of a neural activity measurement system constructed in accordance with one embodiment of the present inventions, particularly shown in the context of a brain computer interface (BCI)

For example, as illustrated in FIG. 3, one embodiment of a neural activity measurement system 10 constructed in accordance with the present inventions will be described. The neural activity measurement system 10 is configured for measuring neural activity in the brain 14 of a user 12, generating commands CMD in response to the measured neural activity information, and sending the commands CMD to an external device 16 in the context of a BCI.

To this end, the neural activity measurement system 10 generally comprises a signal acquisition unit 18 configured for at least partially cancelling a relatively strong outside magnetic field $B_{OUT}$ within an environmental magnetic field $B_{ENV}$ that also includes a relatively weak MEG magnetic field $B_{MEG}$ induced by electrical current (indicative of neural activity) in a brain 14 of a user 12. That is, $B_{TOT}=B_{ENV}+B_{ACT}=B_{OUT}+B_{MEG}+B_{ACT}$. The outside magnetic field $B_{OUT}$ may emanate from global sources (e.g., the Earth's magnetic field), and from localized sources, including, but not limited to, from electromagnetic radiation emanating from electrical outlets and sockets, electrical wires or connections in the wall, and everyday electrical equipment (microwave ovens, televisions, refrigerators, environmental systems (air conditioning, etc.) in a home, office, or laboratory setting, as well as from cell phones, biomagnetics unrelated to neural signals (such as facial muscles, magnetic fields produced by the heart or nerves firing), everyday objects encountered inside (metal and magnetic objects, including steel supports, rebar, studs, utility boxes, etc.) and outside spaces, such as cell phone towers, power lines, transformers, and moving vehicles (e.g., cars, trains, bikes, electric bikes and scooters, electric cars, etc.), user motion/rotation/translation in a background field (earth field), user clothing and eyeglasses, personal electronics (e.g., laptop computers, watches, phones, smart rings, etc.), active implantable medical devices (pacemakers), augmented reality/virtual reality, sound systems (that use magnets), etc.

The signal acquisition unit 18 is configured for generating an actuated magnetic field $B_{ACT}$ that at least partially cancels the relative strong outside magnetic field $B_{OUT}$ within the environmental magnetic field $B_{ENV}$, yielding a total residual magnetic field $B_{TOT}$ (which is preferably zero or near-zero due to the summation of the environmental magnetic field $B_{ENV}$ and the actuated magnetic field $B_{ACT}$). The signal acquisition unit 18 is further configured for detecting the total residual magnetic field $B_{TOT}$ as feedback to cancel the outside magnetic field $B_{OUT}$. The signal acquisition unit 18 is also configured for extracting and outputting a clean (i.e., reduced-noise) electrical MEG signals $S_{MEG}$ of the MEG magnetic field $B_{MEG}$ from the total residual magnetic field $B_{TOT}$.

The signal acquisition unit 18 may utilize any suitable technique for acquiring the MEG magnetic field $B_{MEG}$, including, but not limited to the techniques described in U.S. patent application Ser. No. 16/428,871, entitled "Magnetic Field Measurement Systems and Methods of Making and Using," U.S. patent application Ser. No. 16/418,478, entitled "Magnetic Field Measurement System and Method of Using Variable Dynamic Range Optical Magnetometers", U.S. patent application Ser. No. 16/418,500, entitled, "Integrated Gas Cell and Optical Components for Atomic Magnetometry and Methods for Making and Using," U.S. patent application Ser. No. 16/457,655, entitled "Magnetic Field Shaping Components for Magnetic Field Measurement Systems and Methods for Making and Using," U.S. patent application Ser. No. 16/213,980, entitled "Systems and Methods Including Multi-Mode Operation of Optically Pumped Magnetometer(s)," (now U.S. Pat. No. 10,627,460), U.S. patent application Ser. No. 16/456,975, entitled "Dynamic Magnetic Shielding and Beamforming Using Ferrofluid for Compact Magnetoencephalography (MEG)," U.S. patent application Ser. No. 16/752,393, entitled "Neural Feedback Loop Filters for Enhanced Dynamic Range Magnetoencephalography (MEG) Systems and Methods," U.S. patent application Ser. No. 16/741,593, entitled "Magnetic Field Measurement System with Amplitude-Selective Magnetic Shield," U.S. Provisional Application Ser. No. 62/858,636, entitled "Integrated Magnetometer Arrays for Magnetoencephalography (MEG) Detection Systems and Methods," U.S. Provisional Application Ser. No. 62/836,421, entitled "Systems and Methods for Suppression of Non-Neural Interferences in Magnetoencephalography (MEG) Measurements," U.S. Provisional Application Ser. No. 62/842,818 entitled "Active Shield Arrays for Magnetoencephalography (MEG)," U.S. Provisional Application Ser. No. 62/926,032 entitled "Systems and Methods for Multiplexed or Interleaved Operation of Magnetometers," U.S. Provisional Application Ser. No. 62/896,929 entitled "Systems and Methods having an Optical Magnetometer Array with Beam Splitters," and U.S. Provisional Application Ser. No. 62/960,548 entitled "Methods and Systems for Fast Field Zeroing for Magnetoencephalography (MEG)," which are all expressly incorporated herein by reference.

The neural activity measurement system 10 further comprises a signal processing unit 20 configured for processing the electrical MEG signal $S_{MEG}$ to identify and localize neural activity within the cortex of the brain 14 of the user 12, and issuing the commands CMD to the external device 16 in response to the identified and localized neural activity in the brain 14 of the user 12.

It should be appreciated that, although the neural activity measurement system 10 is described herein in the context of a BCI, the present inventions should not be so limited, and may be applied to any system used for any application (including, but not limited to, medical, entertainment, neuromodulation stimulation, lie detection devices, alarm, educational, etc.), where it is desirable to perform measurements on a magnetic field induced by any physiological process in a person that would benefit from cancelling the outside magnetic field $B_{OUT}$. For example, instead of deriving neural activity information from MEG signals, magnetic fields induced by electrical heart activity can be measured to determine heart activity information of a person.

Furthermore, it should also be appreciated that, although the use of the signal acquisition unit lends itself well to neural activity measurement systems, the signal acquisition unit 18 may find use in other applications, such as, e.g., other types of biomedical sensing, vehicle navigation, mineral exploration, non-destructive testing, detection of underground devices, asteroid mining, space exploration, etc. Thus, signal acquisition unit 18 can be adapted to measure neural signals generated from non-brain anatomical structures, as well as other types of biological signals and non-biological signals.

Figure 4:
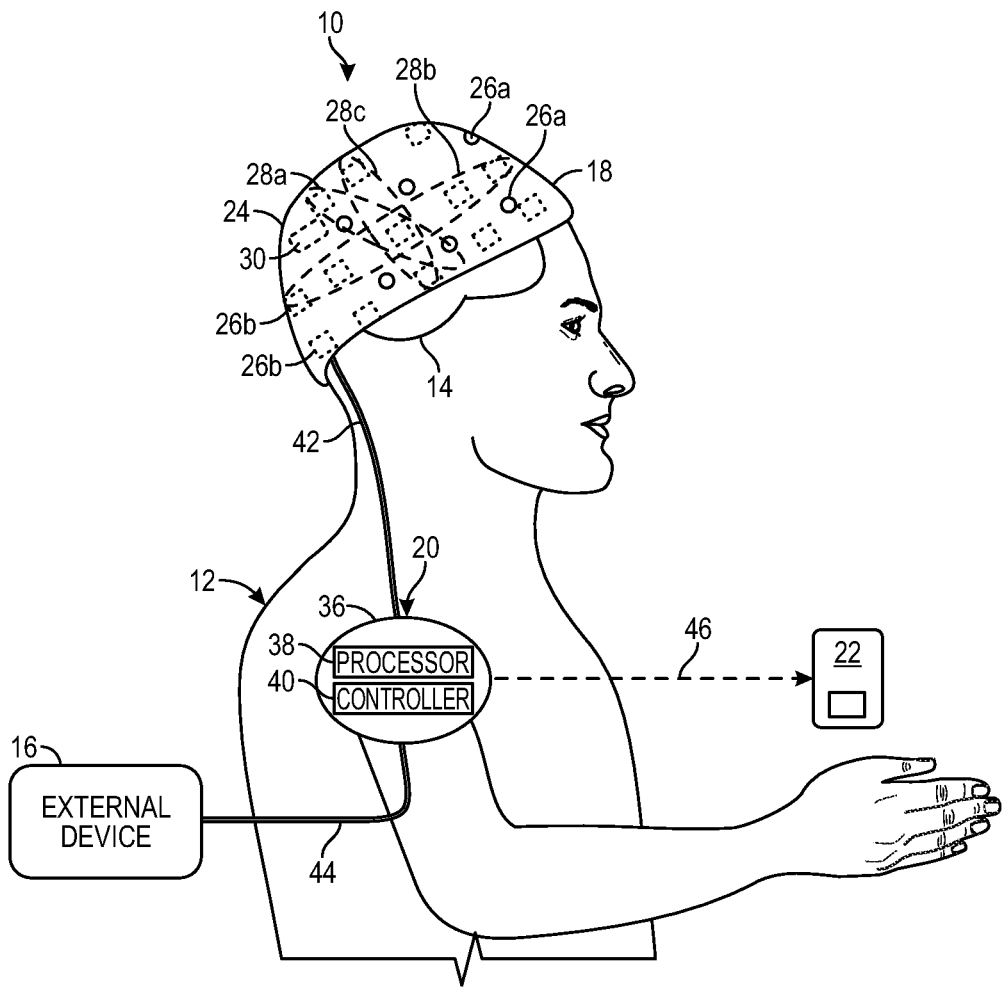
FIG. 4 is a side view of a physical implementation of the BCI of FIG. 3.

Referring now to FIG. 4, an exemplary physical implementation of the neural activity measurement system 10 will be described.

As shown, the signal acquisition unit 18 is configured for being applied to the user 12, and in this case, worn on the head of the user 12. The signal acquisition unit 18 comprises a support structure 24, a plurality of magnetometers 26 (divided between a plurality of coarse magnetometers 26a and a plurality of fine magnetometers 26b) distributed about the support structure 24, a set of magnetic field actuators 28 in proximity to the fine magnetometers 26b, and a processor 30 electrically coupled between the magnetometers 26 and the set of actuators 28.

The support structure 24 may be shaped, e.g., have a banana, headband, cap, helmet, beanie, other hat shape, or other shape adjustable and conformable to the user's head, such that at least some of the magnetometers 26 are in close proximity, preferably in contact, with the outer skin of the head, and in this case, the scalp of the user 12. The support structure 24 may be made out of any suitable cloth, soft polymer, plastic, hard shell, and/or any other suitable material as may serve a particular implementation. An adhesive, strap, or belt (not shown) can be used to secure the support structure 24 to the head of the user 12.

Each of the magnetometers 26 is configured for detecting a spatial component of the total residual magnetic field $B_{TOT}$, and outputting a corresponding electrical signal representative of the spatial component of the total residual magnetic field $B_{TOT}$. In the illustrated embodiment, the plurality of coarse magnetometers 26a is distributed on the outside of the support structure 24 for detecting the respective spatial components of the total residual magnetic field $B_{TOT}$ mainly from outside of the support structure 24, whereas the plurality of fine magnetometers 26b is distributed on the inside of the support structure 24 for detecting the respective spatial components of the total residual magnetic field $B_{TOT}$ mainly from inside the support structure 24 (i.e. they are closer to the brain 14 of the user 12).

Each of the coarse magnetometers 26a has a relatively low sensitivity, but high dynamic sensitivity range, to magnetic fields, whereas each of the fine magnetometers 26b has a relatively high sensitivity, but low dynamic sensitivity range. The signal acquisition unit 18 may have any suitable number of magnetometers 26. For example, the signal acquisition unit 18 may have twelve coarse magnetometers 26a and twenty-five fine magnetometers 26b, although one of ordinary skill in the art would understand that signal acquisition unit 18 may have any suitable number of coarse magnetometers 26a and magnetometers 26b, including more coarse magnetometers 26a then fine magnetometers 26b. In alternative embodiments of the signal acquisition unit 18, the plurality of magnetometers 26 may only comprise a plurality of fine magnetometers 26b distributed on the inside of the support structure 24.

In the illustrated embodiment, each coarse magnetometer 26a takes the form of a flux gate magnetometer, which has a relatively low sensitivity (e.g., on the order of 100 fT), and thus, may not be capable of measuring weak magnetic fields generated by neural activity in the brain 14 of the user 12. However, a flux gate magnetometer has a relatively high dynamic sensitivity range (in the range of 100 fT to close to 100 μT), and thus, may operate in a large outside magnetic field $B_{OUT}$. Although each of the coarse magnetometers 26a are described as taking the form of a flux gate magnetometer, other types of coarse magnetometers can be used, including, but not limited to, anisotropic magnetoresistance (AMR) sensors, tunnel magnetoresistance (TMR) sensors, Hall-effect sensors, nitrogen vacancy sensors, or any other magnetometer that can operate in a linear range over the amplitude range of a typical outside magnetic field $B_{OUT}$.

Figure 1:
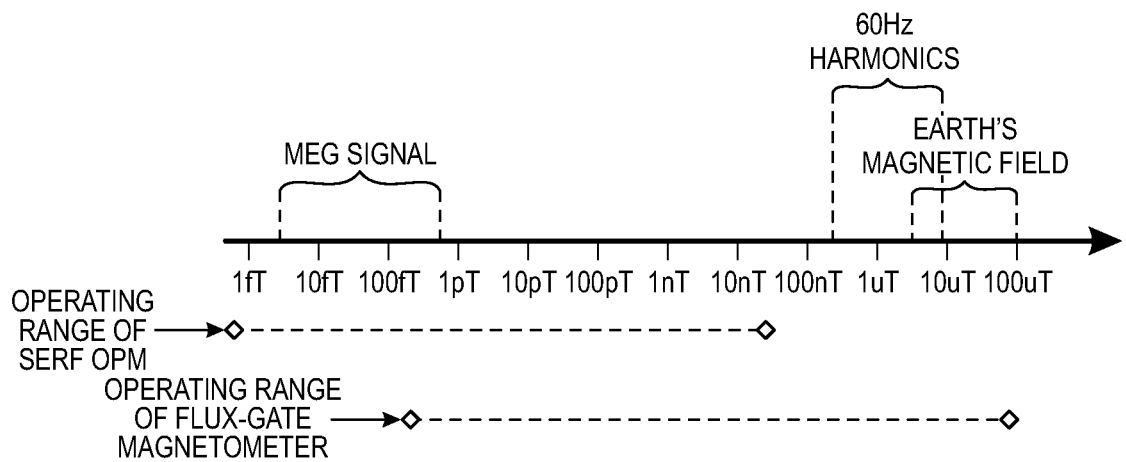
FIG. 1 is a diagram of illustrating dynamic ranges of a magnetoencephalography (MEG) signal and a typical outside magnetic field, and the operating ranges of a Spin Exchange Relaxation Free (SERF) optically-pumped magnetometer (OPM) and flux gate magnetometer, plotted on a magnetic spectrum.
Figure 2:
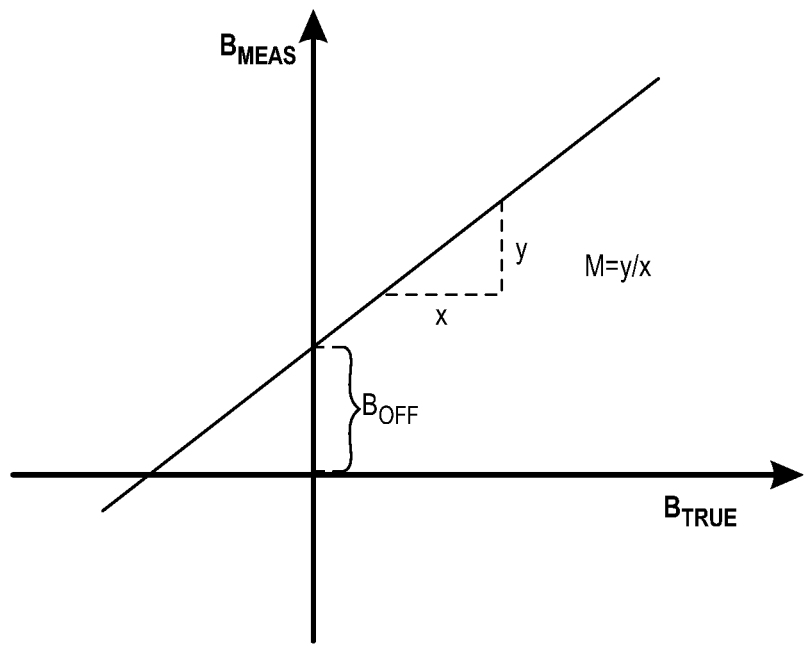
FIG. 2 is a diagram illustrating an offset and gain of a flux gate magnetometer.

It should be appreciated that one issue that arises with the use of flux gate magnetometers, as well as other types of magnetometers based on magnetoresistance effect, including anisotropic magnetoresistance (AMR) and tunnel magnetoresistance (TMR) sensors, is that they may have unknown persistent errors in their measurements that prevents sufficiently accurate coarse estimation of the outside magnetic field. The flux gate magnetometers (equivalently also AMR and TMR) can have offset and gain errors. In particular, FIG. 2 illustrates an exemplary magnetic field $B_{MEAS}$ measured by a flux gate magnetometer versus a true magnetic field $B_{TRUE}$ at the flux gate magnetometer. The measured magnetic field $B_{MEAS}$ has a constant offset $B_{OFF}$ and a gain slope M relative to the true magnetic field $B_{TRUE}$, such that $B_{MEAS}=B_{OFF}+M \times B_{TRUE}$.

Optimally, the constant offset $B_{OFF}$ is zero, and the gain slope M is 1, such that the measured magnetic field $B_{MEAS}$ detected by the flux gate magnetometer equals the true magnetic field $B_{TRUE}$ at the flux gate magnetometer. However, all flux gate magnetometers have offsets $B_{OFF}$, and typically, have errors in the gain slopes M. Thus, any given flux gate magnetometer will consistently report a measured magnetic field $B_{MEAS}$ that is offset from the true magnetic field $B_{TRUE}$ by some amount. In this case, when the true magnetic field $B_{TRUE}$ at the flux gate magnetometer is, in fact, zero, the flux gate magnetometer will report a non-zero measured magnetic field $B_{MEAS}$; or if the flux gate magnetometer reports a zero measured magnetic field $B_{MEAS}$ the true magnetic field $B_{TRUE}$ at the flux gate magnetometer will, in fact, not be zero. If there is an error in the gain slope M (i.e., M does not equal 1), the flux gate magnetometer will incorrectly report changes in the measured magnetic field $B_{MEAS}$. For example, for a 1 nT increase in strength in the true magnetic field $B_{TRUE}$, the flux gate magnetometer may report a 0.95 nT increase in the measured magnetic field $B_{MEAS}$ (a −5% error, gain M=0.95). For the same 1 nT increase in the true magnetic field $B_{TRUE}$, another flux gate magnetometer with a different gain slope M may report a 1.1 nT increase in the measured magnetic field $B_{MEAS}$ (a +10% error, gain M=1.1).

Such persistent offset and gain errors will lead to errors in estimating the true magnetic field $B_{TRUE}$, and thus, errors in applying the cancelling magnetic field by the actuators. The end result is that the fine SERF OPMs may not be brought into its linear operating range, and the system may fail to function as intended.

As will be described in further detail below, each of the coarse magnetometers 26a is specifically designed to facilitate the calibration of its offset and gain using novel pre-calibration and dynamic calibration techniques, so that the magnetic fields reported by the coarse magnetometers 26a can be corrected or compensated.

In the illustrated embodiment, each fine magnetometer 26b takes the form of a Spin Exchange Relaxation Free (SERF) Optically Pumped Magnetometer (OPM). Although a SERF OPM has a relatively small dynamic range (e.g., in the range of 1 ft to 200 nT), it has a relatively high sensitivity (on the order of 1 fT) to magnetic fields compared to flux gate magnetometers. Further details of SERF OPMs are described in U.S. Provisional Application Ser. No. 62/975,693, entitled "Nested and Parallel Feedback Control Loops For Ultra-Fine Measurements of Magnetic Fields From the Brain Using a Wearable MEG System", which is expressly incorporated herein by reference.

The clean (i.e., reduced-noise) electrical MEG signals $S_{MEG}$ that are representative of the spatial components of the MEG magnetic field $B_{MEG}$, and that will be processed by the signal processing unit 20 for determining and localizing neural activity in the brain 14 of the user 12, will be respectively derived from the electrical signals output by the respective fine magnetometers 26b, and in some cases, from the electrical signals output by the coarse magnetometers 26a; whereas the characteristics (namely amplitude and phase) of the actuated magnetic field $B_{ACT}$ will be derived from the electrical signals output by the respective coarse magnetometers 26a and/or the electrical signals output by at least some of the respective fine magnetometers 26b.

The set of magnetic field actuators 28 is configured for generating the actuated magnetic field $B_{ACT}$ to at least partially cancel the outside magnetic field $B_{OUT}$ in the vicinity of the plurality of fine magnetometers 26b. The set of magnetic field actuators 28 may, e.g., comprise at least one coil and at least one driver that drives the coil(s) with electrical current at a defined amperage, voltage, or some other variable, and at a defined frequency, thereby setting the actuation strengths of the magnetic field actuators 28. In the illustrated embodiment, the set of magnetic field actuators 28 comprises a triad of uniform magnetic field actuators 28a-28c for respectively generating x-, y-, and z-components of the actuated magnetic field $B_{ACT}$ to cancel the outside magnetic field $B_{OUT}$ in all three dimensions. In an optional embodiment, the set of magnetic field actuators 28 may also comprise six gradient magnetic field actuators (not shown) for generating first-order x-, y-, and z-gradient components of the actuated magnetic field $B_{ACT}$. One of ordinary skill in the art would appreciate that the set of field actuators 28 may include any suitable and type of magnetic field actuators capable of cancelling the outside magnetic field $B_{OUT}$ at the magnetometers 26.

The processor 30 is electrically coupled between the magnetometers 26 and magnetic field actuators 28 via electrical wires (not shown), and is configured for processing the measurements of the total residual magnetic field $B_{TOT}$ reported by the coarse magnetometers 26a (and in some cases the measurements of the total residual magnetic field $B_{TOT}$ reported by the fine magnetometers 26b) in response to the detection of the spatial components of the total residual magnetic field $B_{TOT}$.

The processor 30 is further configured for estimating the total residual magnetic field $B_{TOT}$ at the fine magnetometers 26b based on the measurements of the total residual magnetic field $B_{TOT}$ reported by the total residual magnetic field $B_{TOT}$ reported by the coarse magnetometers 26a (e.g., using one or more of the estimation techniques described in U.S. Provisional Application Ser. No. 62/975,719, entitled "Estimating the Magnetic Field at Distances From Direct Measurements to Enable Fine Sensors to Measure the Magnetic Field from the Brain by Using a Wearable MEG System", and U.S. Provisional Application Ser. No. 62/975,723, entitled "Algorithms that Exploit Maxwell's Equations and Geometry to Reduce Noise for Ultra-Fine Measurements of Magnetic Fields from the Brain Using a Wearable MEG System", which are expressly incorporated herein by reference).

Based on the estimates of the total residual magnetic field $B_{TOT}$ at the fine magnetometers 26b, the processor 30 is further configured for determining the characteristics of the actuated magnetic field $B_{ACT}$ required to cancel the outside magnetic field $B_{OUT}$ in a manner that suppresses the total residual magnetic field $B_{TOT}$ at the fine magnetometers 26b, and generating noise-cancelling control signals based on this determination that are output to the set of magnetic field actuators 28. As a result, the fine magnetometers 26 come in-range, such that the total residual magnetic field $B_{TOT}$ measured by the fine magnetometers 26 is more accurate, and as thus, the electrical MEG signals $S_{MEG}$ of the MEG magnetic field $B_{MEG}$ extracted from the total residual magnetic field $B_{TOT}$ by the signal acquisition unit 18 are more accurate.

Further details discussing novel techniques for cancelling the outside magnetic field $B_{OUT}$ in the total residual magnetic field $B_{TOT}$ are described in U.S. Provisional Application Ser. No. 62/975,693, entitled "Nested and Parallel Feedback Control Loops For Ultra-Fine Measurements of Magnetic Fields From the Brain Using a Wearable MEG System". Significantly, as will be described in further detail below, the processor 30 is also configured for dynamically calibrating the coarse magnetometers 26a, and in particular, the calibrating the gains of the coarse magnetometers 26a as the signal acquisition unit 18 is worn by the user 12.

To minimize the size, weight, and cost of the signal acquisition unit 18, the functions of the processor 30 are preferably performed digitally (e.g., in firmware, such as a programmable logic device (e.g., a field programmable gate array (FPGA), or an ASIC (application specific integrated circuit) device, or in a micro-processor)), in which case, one or more analog-to-digital converters (not shown) can be employed between the magnetometers 26 and the processor 30, and one or more digital-to-analog converters (not shown) can be employed between the magnetic field actuators 28 and the processor 30. However, it should be appreciated that, in alternative embodiments, the functions of the processor 30 may be at least partially performed in an analog fashion.

The signal acquisition unit 18 may then derive the electrical signals MEG signals $S_{MEG}$ of the MEG magnetic field $B_{MEG}$ from the measurements of the total residual magnetic field $B_{TOT}$ reported by the fine magnetometers 26b (e.g., either directly from the measurements or indirectly from estimates of the total residual magnetic field $B_{TOT}$ at the fine magnetometers 26b derived from the measurements of the total residual magnetic field $B_{TOT}$ reported by the fine magnetometers 26b).

It should be noted that, although the signal acquisition unit 18 is illustrated in FIG. 3 as having a single set of magnetic field actuators 28 and a single processor 30, the signal acquisition unit 18 may comprise more than one set of magnetic field actuators 28 and more than one processor 30. In this case, each set of magnetic field actuators 28 and each corresponding processor 30 may be associated with a subset of magnetometers 26. In one embodiment, the fine magnetometers 26b, set(s) of magnetic field actuators 28, and processor(s) 30 may be fabricated as integrated module(s). For example, each integrated module may comprise a rectangular substrate containing a subset or all of the fine magnetometers 26b, a set of the magnetic field actuators 28 incorporated into the rectangular substrate, such that coils of the magnetic field actuators 28 respectively wrap around the orthogonal dimensions of the rectangular substrate, and the processor 30 affixed to the surface of the rectangular substrate between the coils.

The signal processing unit 20 is configured for being applied to the user 12, and in this case, worn remotely from the head of the user 12, e.g., worn on the neck, shoulders, chest, or arm) of the user 12. The signal processing unit 20 comprises a housing 36 containing its own processor 38 and a controller 40. The processor 38 is configured for identifying and localizing neural activity within the cortex of the brain 14 of the user 12, and the controller 40 is configured for issuing commands CMD to an external device 16 in response to the identified and localized neural activity in the brain 14 of the user 12, as well as controlling the high-level operational functions of the signal acquisition unit 18. The signal processing unit 20 may additionally include a power supply (which if head-worn, may take the form of a rechargeable or non-chargeable battery), a control panel with input/output functions, a display, and memory. Alternatively, power may be provided to the signal processing unit 20 wirelessly (e.g., by induction).

In the illustrated embodiment, the neural activity measurement system 10 further comprises a wired connection 42 (e.g., electrical wires) for providing power from the signal processing unit 20 to the signal acquisition unit 18 and communicating between the signal processing unit 20 and the signal acquisition unit 18. Alternatively, the neural activity measurement system 10 may use a non-wired connection (e.g., wireless radio frequency (RF) signals (e.g., Bluetooth, Wifi, cellular, etc.) or optical links (e.g., fiber optic or infrared (IR)) for providing power from the signal processing unit 20 to the signal acquisition unit 18 and/or communicating between the signal processing unit 20 and the signal acquisition unit 18.

In the illustrated embodiment, the neural activity measurement system 10 further comprises a wired connection 44 (e.g., electrical wires) for providing power from the signal processing unit 20 to the external device 16 and communicating between the signal processing unit 20 and the external device 16. Alternatively, the neural activity measurement system 10 may use a non-wired connection (e.g., wireless radio frequency (RF) signals (e.g., Bluetooth, Wifi, cellular, etc.) or optical links (e.g., fiber optic or infrared (IR)) for providing power from the signal processing unit 20 to the external device 16 and/or communicating between the signal processing unit 20 and the external device 16.

The neural activity measurement system 10 may optionally comprise a remote processor 22 (e.g., a Smartphone, tablet computer, or the like) in communication with the signal processing unit 20 coupled via a wired connection (e.g., electrical wires) or a non-wired connection (e.g., wireless radio frequency (RF) signals (e.g., Bluetooth, Wifi, cellular, etc.) or optical links (e.g., fiber optic or infrared (IR)) 46. The remote processor 22 may store data from previous sessions, and include a display screen.

It should be appreciated that at least a portion of the signal acquisition and magnetic field cancellation functionality of the processor 30 in the signal acquisition unit 18 may be implemented in the signal processing unit 20, and/or at least a portion of the neural activity determination and localization functionality of the signal processing unit 20 may be implemented in the signal acquisition unit 18. In the preferred embodiment, the functionalities of the processor 30 in the signal acquisition unit 18, as well as the processor 38 and a controller 40 in the signal processing unit 20, may be implemented using one or more suitable computing devices or digital processors, including, but not limited to, a microcontroller, microprocessor, digital signal processor, graphical processing unit, central processing unit, application specific integrated circuit (ASIC), field programmable gate array (FPGA), and/or programmable logic unit (PLU). Such computing device(s) or digital processors may be associated with non-transitory computer- or processor-readable medium that stores executable logic or instructions and/or data or information, which when executed, perform the functions of these components. The non-transitory computer- or processor-readable medium may be formed as one or more registers, for example of a microprocessor, FPGA, or ASIC, or can be a type of computer-readable media, namely computer-readable storage media, which may include, but is not limited to, RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Figure 5:
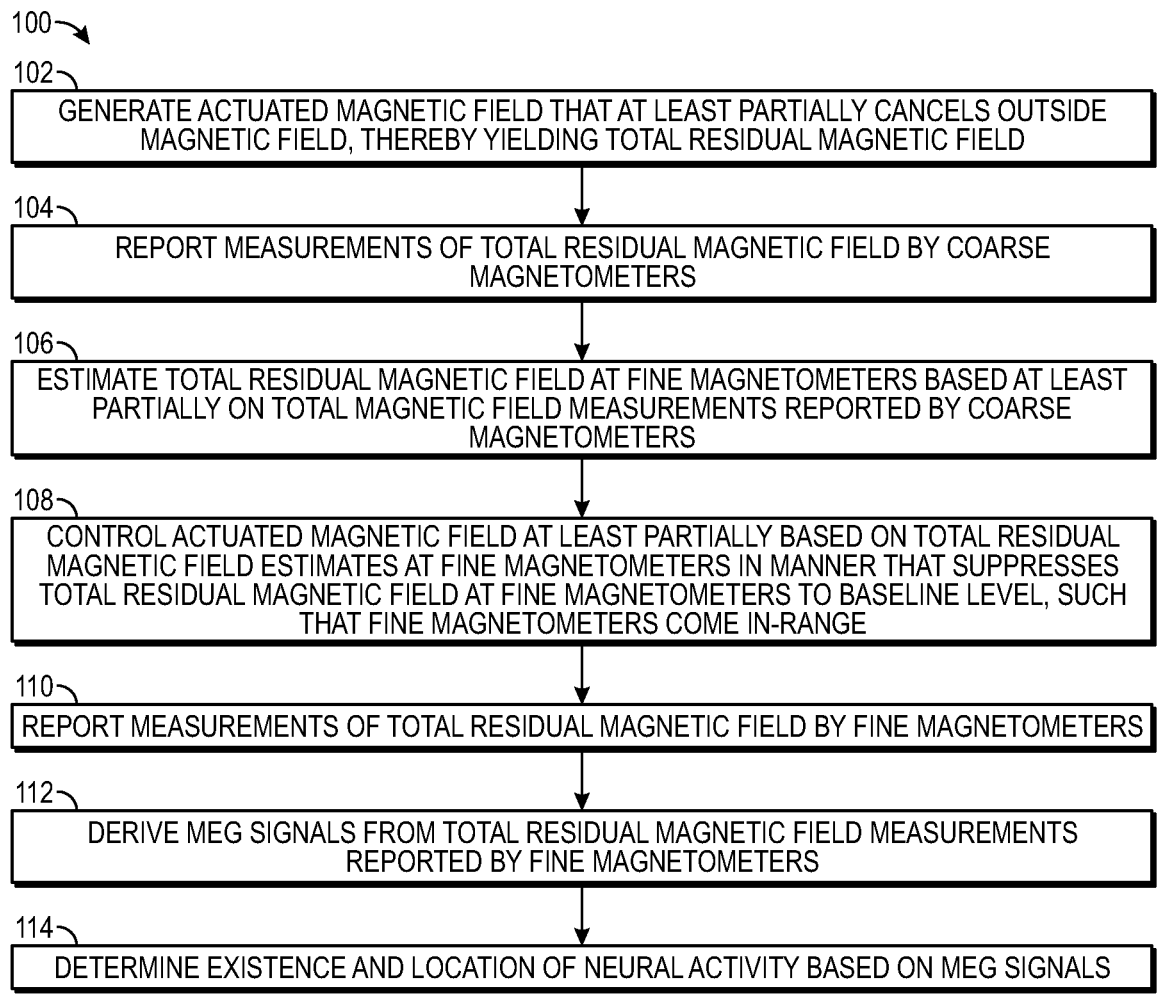
FIG. 5 is a flow diagram illustrating one exemplary method of operating the neural activity measurement system to detect neural activity in the brain of a user.

Referring to FIG. 5, one exemplary method 100 acquiring MEG signals $S_{MEG}$ from the brain 14 of the user 12 will now be described.

The method 100 comprises generating the actuated magnetic field $B_{ACT}$ (via the set of magnetic actuators 28) that at least partially cancels an outside magnetic field $B_{OUT}$, thereby yielding a total residual magnetic field $B_{TOT}$ (step 102). In the preferred embodiment, the actuated magnetic field $B_{ACT}$ is generated in all three dimensions and is uniform, although in alternative embodiments, the actuated magnetic field $B_{ACT}$ may be generated in less three dimensions and may be non-uniform (e.g., a gradient).

The method 100 further comprises reporting measurements of the total residual magnetic field $B_{TOT}$ by the coarse magnetometers 26a (step 104), and estimating the total residual magnetic field $B_{TOT}$ at the fine magnetometers 26b based at least partially on the measurements of the total residual magnetic field $B_{TOT}$ reported by the coarse magnetometers 26a (step 106).

The method 100 further comprises controlling the actuated magnetic field $B_{ACT}$ at least partially based on the estimates of the total residual magnetic field $B_{TOT}$ at the fine magnetometers 26b in a manner that suppresses the total residual magnetic field $B_{TOT}$ at the fine magnetometers to a baseline level (e.g., by sending noise-cancelling control signals to the set of magnetic field actuators 28), such that fine magnetometers 26b come in-range) (step 108).

The method further comprises reporting measurements of the total residual magnetic field $B_{TOT}$ by the fine magnetometers 26b (step 110), and deriving a plurality of MEG signals $S_{MEG}$ respectively from the measurements of the total residual magnetic field $B_{TOT}$ reported by the fine magnetometers 26b (directly from the measurements of the total residual magnetic field $B_{TOT}$ reported by the fine magnetometers 26 or indirectly from estimates of the total residual magnetic field $B_{TOT}$ reported by the fine magnetometers 26 that have been at least partially determined from the measurements of the total residual magnetic field $B_{TOT}$ reported by the fine magnetometers 26) (step 112). That is, because the total residual magnetic field $B_{TOT}$ reported by the fine magnetometers 26b contains the MEG magnetic field $B_{MEG}$ from the brain 14 of the user 12, and thus by inference, the measurements of the total residual magnetic field estimates $B_{TOT}$ reported by the fine magnetometers 26b contains the MEG magnetic field $B_{MEG}$ from the brain 14 of the user 12, the MEG signals $S_{MEG}$ can be derived from the measurements of the total residual magnetic field estimates $B_{TOT}$ reported by the fine magnetometers 26b. The method 100 lastly comprises determining the existence and detection location of neural activity in the brain 14 of the user 12 based on the MEG signals $S_{MEG}$ via the signal processing unit 20 (step 114).

Figure 6:
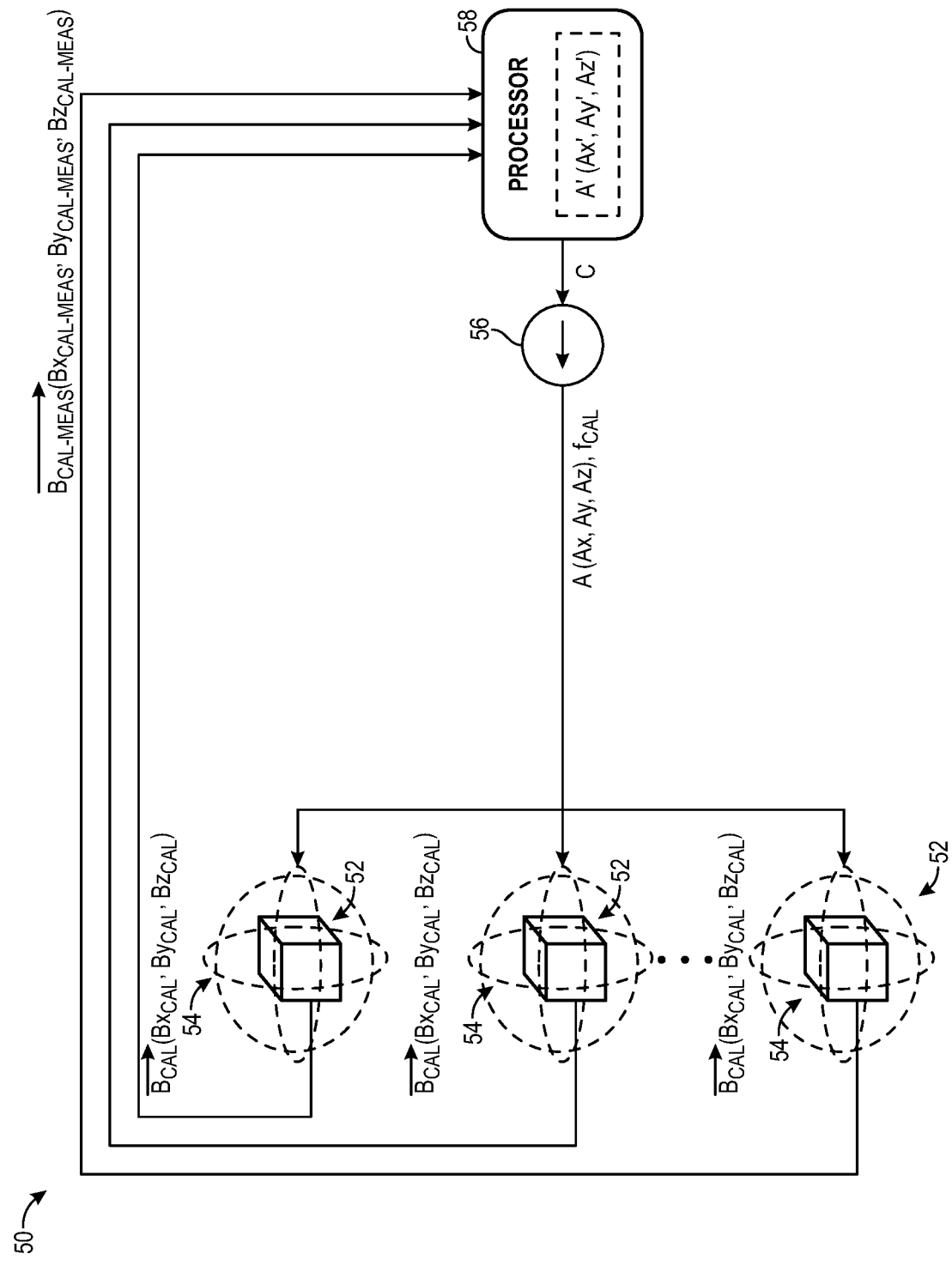
FIG. 6 is a block diagram illustrating a magnetometer calibration system constructed in accordance with one embodiment of the present inventions, for dynamically calibrating a gain of a coarse magnetometer used in the neural activity measurement system of FIG. 3.

Referring now to FIG. 6, the signal acquisition unit 18 further comprises a magnetometer calibration system 50 that generally comprises a plurality of coarse magnetometers 52, a set of calibration coils 54 for each coarse magnetometer 52, at least one driver 56, and a processor 58. Significantly, the gain G of each of the coarse magnetometers 52 can be dynamically calibrated during real-time operation of the signal acquisition unit 18.

Figure 7A:
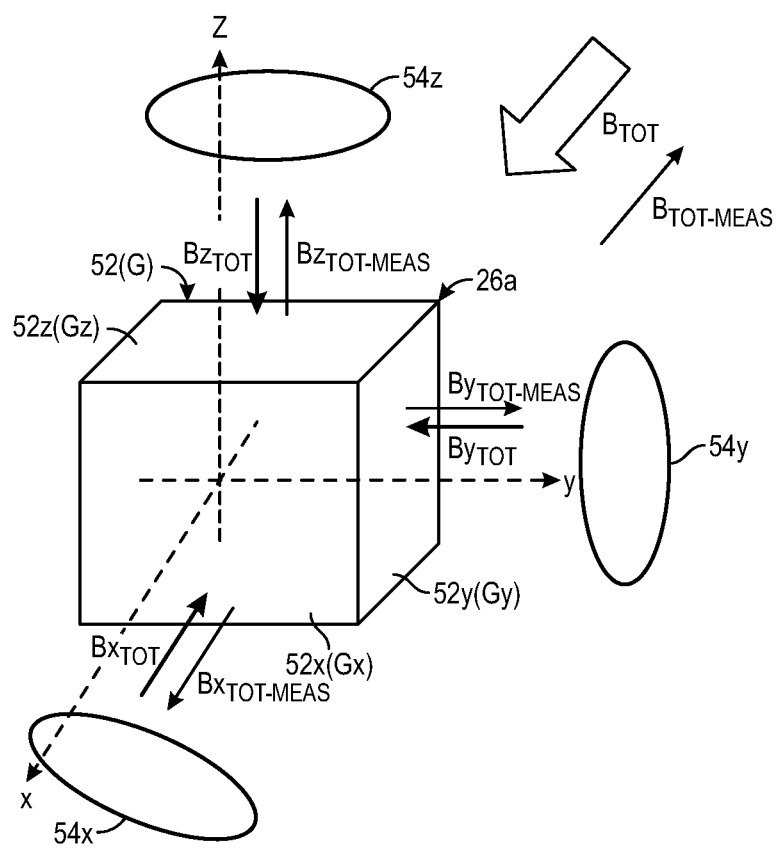
FIG. 7A is a block diagram illustrating one embodiment of a coarse magnetometer being operated by the neural activity measurement system of FIG. 3 in a cancellation mode to coarsely cancel an outside magnetic field.
Figure 7B:
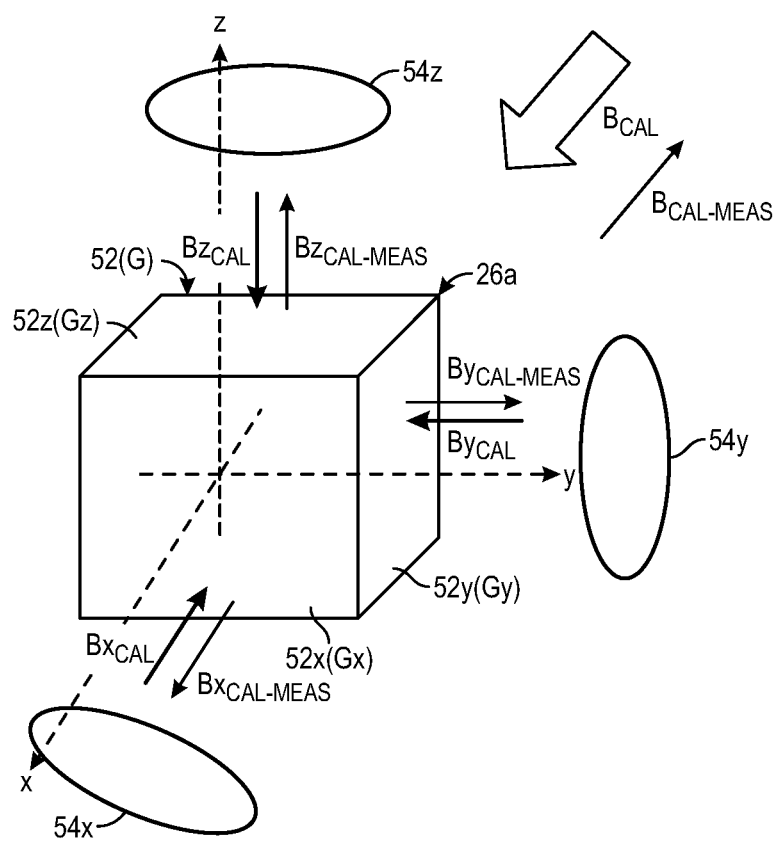
FIG. 7B is a block diagram illustrating the coarse magnetometer of FIG. 7A being calibrated by the magnetometer calibration system of FIG. 6 during a calibration mode.

Each of the coarse magnetometers 52 may correspond to one of the coarse magnetometers 26a illustrated in FIG. 4. As illustrated in FIGS. 7A and 7B, each of the coarse magnetometers 52 is designed as a vector coarse magnetometer that comprises a triad of mutually orthogonal scalar magnetometers (e.g., scalar flux gates) 52x, 52y, and 52z that are mutually orthogonally arranged relative to each other, such that the scalar magnetometers 52x, 52y, and 52z respectively lie in planes that perpendicular to the x-axis, y-axis, and z-axis of a Cartesian coordinate system, thereby enabling the coarse magnetometer 52 to detect magnetic fields in three spatial dimensions (x, y, and z). Thus, the gain G of each coarse magnetometer 52 is a vector $\vec{G}$; that is, the scalar magnetometers 52x, 52y, and 52z respectively have gains Gx, Gy, and Gz. Each coarse magnetometer 52 may either be operated in a cancellation mode (FIG. 7A) or a calibration mode (FIG. 7B).

As illustrated in FIG. 7A, during the cancellation mode, where it is desired to coarsely cancel the outside magnetic field $B_{OUT}$, as discussed above, each coarse magnetometer 52 detects the true total residual magnetic field $B_{TOT}$ having a vector $\vec{B}_{TOT}$ and measures (reports) a total residual magnetic field $B_{TOT\text{-}MEAS}$ having a vector $\vec{B}_{TOT\text{-}MEAS}$. That is, the scalar magnetometers 52x, 52y, and 52z of each coarse magnetometer 52 respectively detect the directional components $Bx_{TOT}$, $By_{TOT}$, and $Bz_{TOT}$ of the true total residual magnetic field $\vec{B}_{TOT}$, and measures (reports) the directional components $Bx_{TOT\text{-}MEAS}$, $By_{TOT\text{-}MEAS}$, and $Bz_{TOT\text{-}MEAS}$ of a measured total residual magnetic field $\vec{B}_{TOT\text{-}MEAS}$.

Optimally, the gains Gx, Gy, and Gz of the scalar magnetometers 52x, 52y, and 52z of each coarse magnetometer 52 are each unity (i.e., one), such that directional components $Bx_{TOT\text{-}MEAS}$, $By_{TOT\text{-}MEAS}$, and $Bz_{TOT\text{-}MEAS}$ of the measured total residual magnetic field $\vec{Bx}_{TOT\text{-}MEAS}$ reported by the scalar magnetometers 52x, 52y, and 52z are equal to the directional components $Bx_{TOT}$, $By_{TOT}$, and $Bz_{TOT}$ of the true total residual magnetic field $\vec{B}_{TOT}$ at the scalar magnetometers 52x, 52y, and 52z.

However, in practice, the gains Gx, Gy, and Gz of the scalar magnetometers 52x, 52y, and 52z of any given coarse magnetometer 52 are not unity, and will drift in time due to, e.g., temperature changes, deformation of the support structure 24 to which the coarse magnetic sensors 26 are mounted, and other dynamic variations. Thus, the directional components $Bx_{TOT\text{-}MEAS}$, $By_{TOT\text{-}MEAS}$, and $Bz_{TOT\text{-}MEAS}$ of the total residual magnetic field $\vec{B}_{TOT\text{-}MEAS}$ reported by the scalar magnetometers 52x, 52y, and 52z will typically not be equal to the directional components $Bx_{TOT}$, $By_{TOT}$, and $Bz_{TOT}$ of the true total residual magnetic field $\vec{B}_{TOT}$ at the scalar magnetometers 52x, 52y, and 52z, and thus, must be calibrated in order to apply the correct current amplitudes to the actuators 28 (shown in FIG. 4) for proper cancellation of the outside magnetic field $B_{OUT}$.

The calibration system 50 is configured for dynamically calibrating the gains G of the coarse magnetometers 52, and in particular, the gains Gx, Gy, and Gz of the scalar magnetometers 52x, 52y, and 52z of each of the coarse magnetometers 52. Referring back to FIG. 6, each set of calibration coils 54 is placed in close proximity to one of the coarse magnetometers 52. Each set of calibration coils 54 is configured for generating a calibrating magnetic field $B_{CAL}$ localized at the coarse magnetometer 52 spatially associated with the set of calibration coils 54, preferably in three spatial dimensions (x, y, and z), such that the calibrating magnetic field has a vector $\vec{B}_{CAL}$, and thus comprises directional components $Bx_{CAL}$, $By_{CAL}$, and $Bz_{CAL}$. Each set of calibration coils 54 may include more than one coil or only one coil as long as the calibration coil(s) 52 span three spatial dimensions (i.e., linearly dependent), such that the calibrating magnetic field $\vec{B}_{CAL}$ is in three spatial dimensions.

The set of drivers 56 may take any suitable form that can accurately actuate the calibration coils 54 in a known and predictable manner. In the illustrated embodiment, the driver(s) 56 actuate the calibration coils 54 with an electrical current at a defined amplitude (e.g., amperage, voltage, or some other variable) and defined frequency, thereby setting the actuation strengths of the calibration coils 54. In one preferred embodiment, the driver(s) 56 take the form of current source(s), thereby setting the actuation strengths of the calibration coils 54.

The driver(s) 56 may include only one driver 56 for all sets of calibration coils 54, or only one driver 56 for each set of calibration coils 54, but preferably comprises sets of drivers 56a, each set corresponding to a different set of calibration coils 54. If each set of calibration coils 54 comprises more than one coil, each set of drivers 56 may comprise dedicated drivers 56 for individually actuating the respective coils 54x, 54y, and 54z) to maximize control of each set of calibration coils 54, i.e., to ensure that the calibrating magnetic field $B_{CAL}$ is generated by each set of calibration coils 54 in a known and predictable manner. If each set of calibration coils 54 comprises only one coil, each set of drivers 56 may comprise only one driver 56 for globally actuating the calibration coil 54.

As illustrated in FIG. 7B, during the calibration mode, where it is desired to dynamically calibrate the gains Gx, Gy, and Gz of the scalar magnetometers 52x, 52y, and 52z the coarse magnetometers 52, each coarse magnetometer 52 detects the calibrating magnetic field having a vector $\vec{B}_{CAL}$ and measures (reports) a calibrating magnetic field $B_{CAL\text{-}MEAS}$ having a vector $\vec{B}_{CAL\text{-}MEAS}$. That is, the scalar magnetometers 52x, 52y, and 52z of each coarse magnetometer 52 respectively detect the directional components $Bx_{CAL}$, $B_{CAL}$, and $Bz_{CAL}$ of the calibrating magnetic field $\vec{B}_{CAL}$, and measures (reports) the directional components $Bx_{CAL\text{-}MEAS}$, $By_{CAL\text{-}MEAS}$, and $Bz_{CAL\text{-}MEAS}$ of a calibrating magnetic field $\vec{B}_{CAL\text{-}MEAS}$.

Because the gains Gx, Gy, and Gz of the scalar magnetometers 52x, 52y, and 52z of any given coarse magnetometer 52 are not unity, the directional components $Bz_{CAL}$, $By_{CAL\text{-}MEAS}$, and $Bz_{CAL\text{-}MEAS}$ of the measured calibrating magnetic field $\overrightarrow{B_{CAL\text{-}MEAS}}$ reported by the scalar magnetometers 52x, 52y, and 52z (and reflected in the directional components $Sx_{CAL}$, $Sy_{CAL}$, and $Sz_{CAL}$ of the measured calibration signal $\overrightarrow{S_{CAL}}$) will typically not be equal to the directional components $Bx_{CAL}$, $By_{CAL}$, and $Bz_{CAL}$ of the true calibrating magnetic field $\overrightarrow{B_{CAL}}$ at the scalar magnetometers 52x, 52y, and 52z.

In one embodiment, the magnetometer calibration system 50 utilizes calibration-enabled magnetometer assemblies 60 (shown as a calibration-enabled magnetometer assembly 60a in FIG. 8A and a calibration-enabled magnetometer assembly 60b in FIG. 8B), which can affixed to the support structure 24 of the signal acquisition unit 18 to enable both cancellation of the outside magnetic field $B_{OUT}$ and calibration of the coarse magnetometers 52. Each calibration-enabled magnetometer assembly 60 comprises a coarse magnetometer 52, at least one coil 54, and a fixture 62 that carries the coarse magnetometer 52 and coil(s) 52 in close proximity to each other.

The triad of scalar magnetometers 52x, 52y, and 52z are mutually orthogonally affixed to the fixture 62. In the embodiment illustrated in FIG. 8A, the set of calibration coils 54 comprises a triad of calibration coils 54x, 52y, 52z are respectively affixed to the fixture 62, such that they are mutually orthogonal to each other (i.e., in disposed in orthogonal planes), resulting in the generation of the directional components $Bx_{CAL}$, $By_{CAL}$, and $Bz_{CAL}$ of the calibrating magnetic field $\overrightarrow{B_{CAL}}$ in respective directions perpendicular to the three orthogonal planes. In an alternative embodiment illustrated in FIG. 8B, the set of calibration coils 54 comprises a single calibration coil 54 is affixed to the fixture 62, such that it lies in three orthogonal planes, likewise resulting in the generation of the directional components $Bx_{CAL}$, $By_{CAL}$, and $Bz_{CAL}$ of the calibrating magnetic field $\overrightarrow{B_{CAL}}$ in respective directions perpendicular to the three orthogonal planes.

In the illustrated embodiment, the fixture 62 has a rectangular geometry (and in this case, a cube) having six faces 62a-62f—a first set of three orthogonal faces 62a-62c, and a second set of three orthogonal faces 62d-62f that are respectively opposite to, but parallel, to the first set of orthogonal faces 62a-62c. The scalar magnetometers 52x, 52y, and 52z are respectively affixed to the first set of orthogonal faces 62a-62c, so that they are arranged orthogonally relative to each other. The fixture 62 can be composed of any magnetically-transparent material, including polycarbonate or glass.

Figure 8A:
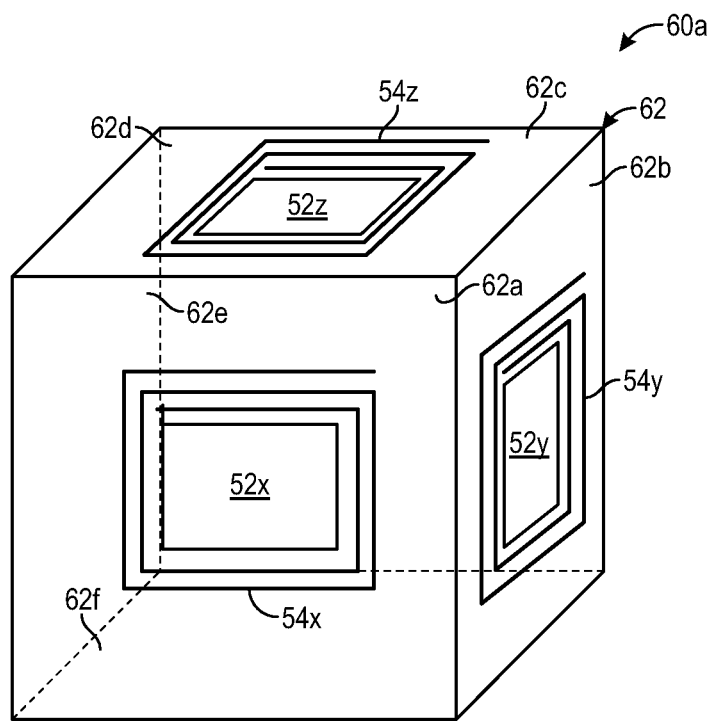
FIG. 8A is a perspective view of one embodiment of a calibration-enabled magnetometer assembly constructed in accordance with the present inventions, and for use in the magnetometer calibration system of FIG. 6.

In the embodiment illustrated in FIG. 8A, the calibration coils 54x, 52y, 52z are respectively affixed to the first set of orthogonal faces 62a-62c of the rectangular fixture 62 (i.e., the same faces to which the corresponding scalar magnetometers 52x, 52y, and 52z are affixed), such that the proximity between the calibration coils 54x, 52y, 52z and the respective scalar magnetometers 52x, 52y, and 52z is as small as possible. However, in alternative embodiments, the calibration coils 54x, 52y, 52z may be respectively affixed to the second set of orthogonal faces 62a-62c of the rectangular fixture 62 (i.e., the faces opposite to the faces to which the corresponding scalar magnetometers 52x, 52y, and 52z are affixed).

Figure 8B:
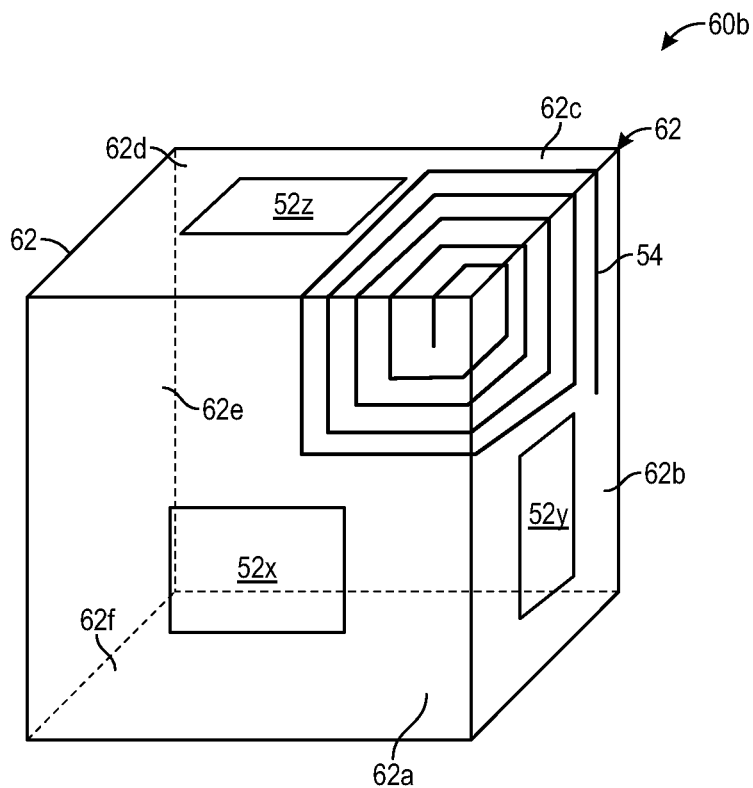
FIG. 8B is a perspective view of another embodiment of a calibration-enabled magnetometer assembly constructed in accordance with the present inventions, and for use in the magnetometer calibration system of FIG. 6.

In the embodiment illustrated in FIG. 8B, the single calibration coil 54 is affixed to one corner of the rectangular fixture 62, such that portions of the single calibration coil 54 are disposed on the first set of orthogonal faces 62a-62c of the rectangular fixture 62 (i.e., the same faces to which the corresponding scalar magnetometers 52x, 52y, and 52z are affixed), although in alternative embodiments, the single calibration coil 54 may be affixed to a different corner of the rectangular fixture 62, such that portions of the single calibration coil 54 are disposed on the first set of orthogonal faces 62a-62c of the rectangular fixture 62 (i.e., the faces opposite to the faces to which the corresponding scalar magnetometers 52x, 52y, and 52z are affixed).

Although the fixture 62 is described as having a rectangular geometry, it should be appreciated that the fixture 62 may have any polygonal shape, or even a non-polygonal shape, that allows the scalar magnetometers 52x, 52y, and 52z and the calibration coils 54x, 52y, 52z (FIG. 8A) or the single calibration coil 54 (FIG. 8B) to be disposed in mutually orthogonal directions.

Referring back to FIG. 6, the processor 58 may be the same processor 30 that performs the coarse cancellation of the outside magnetic field $B_{OUT}$ in the signal acquisition unit 18 described above, or may be a different processor 30. For each coarse magnetometer 52, the processor 58 is configured for generating a control signal C that defines an amplitude A (which can be amplitudes Ax, Ay, and Az (which may be the same) if the set of calibration coils 54 includes a triad of coils 54x, 54y, and 54z (e.g., in FIG. 8A) or a single value if the set of calibration coils 54 includes a single coil (e.g., in FIG. 8B) and a calibration frequency $f_{CAL}$ of the current(s) output by the driver(s) 56, which actuate the corresponding set of calibration coils 54 to generate the directional components $Bx_{CAL}$, $By_{CAL}$, and $Bz_{CAL}$ of the calibrating magnetic fields $\overrightarrow{B_{CAL}}$ at the corresponding coarse magnetometer 52, as shown in FIG. 7B.

As shown in FIG. 7B, for each coarse magnetometer 52, the processor 58 is further configured for determining the gains Gx, Gy, and Gz of the scalar magnetometers 52x, 52y, and 52z by comparing the directional components $Bx_{CAL}$, $By_{CAL}$, and $Bz_{CAL}$ of the true calibrating magnetic field $\overrightarrow{B_{CAL}}$ at the scalar magnetometers 52x, 52y, and 52z to the directional components $Bx_{CAL\text{-}MEAS}$, $By_{CAL\text{-}MEAS}$, and $Bz_{CAL\text{-}MEAS}$ of the magnetic field $\overrightarrow{B_{CAL\text{-}MEAS}}$ reported by the scalar magnetometers 52x, 52y, and 52z. Ignoring frequency roll-off gain errors (which characterizes roll-off effects of the gains Gx, Gy, and Gz of the scalar magnetometers 52x, 52y, and 52z at third operating frequencies and the calibration frequency $f_{CAL}$, as described in further detail below) of the scalar magnetometers 52x, 52y, and 52z for the moment, the gains Gx, Gy, and Gz of the scalar magnetometers 52x, 52y, and 52z can be computed in accordance with the following ratios:

$$Gx = \frac{Bx_{CAL\text{-}MEAS}}{Bx_{CAL}}; \qquad [1a]$$

$$Gy = \frac{By_{CAL\text{-}MEAS}}{By_{CAL}}; \text{ and} \qquad [1b]$$

$$Gz = \frac{Bz_{CAL\text{-}MEAS}}{Bz_{CAL}}. \qquad [1c]$$

The processor 58 may determine the amplitudes of the directional components $Bx_{CAL}$, $By_{CAL}$, and $Bz_{CAL}$ of the true calibrating magnetic field $\vec{B}_{CAL}$ at the scalar magnetometers 52*x*, 52*y*, and 52*z* from the known amplitude A of the current(s) output by the driver(s) 56 using linear mapping (i.e., the amplitudes of the directional components $Bx_{CAL}$, $By_{CAL}$, and $Bz_{CAL}$ may be scaled versions of the known amplitude A of the current(s) output by the driver(s) 56 in accordance with a constant C1). In this regard, the amplitude of the directional components $Bx_{CAL}$, $B_{CAL}$, and $Bz_{CAL}$ of the true calibrating magnetic field $\vec{B}_{CAL}$ are known at the scalar magnetometers 52*x*, 52*y*, and 52*z*.

Likewise, the processor 58 may determine the amplitudes of the directional components $Bx_{CAL-MEAS}$, $By_{CAL-MEAS}$, and $Bz_{CAL-MEAS}$ of the magnetic field $\vec{B}_{CAL-MEAS}$ reported by scalar magnetometers 52*x*, 52*y*, and 52*z* from the known amplitudes $Ax_{CAL-MEAS}$, $Ay_{CAL-MEAS}$, and $Az_{CAL-MEAS}$ of the directional components $Sx_{CAL-MEAS}$, $Sy_{CAL-MEAS}$, and $Sz_{CAL-MEAS}$ of the signal $\vec{S}_{CAL-MEAS}$ output by the respective scalar magnetometers 52*x*, 52*y*, and 52*z* using linear mapping (i.e., the amplitudes of the directional components $Bx_{CAL-MEAS}$, $By_{CAL-MEAS}$, and $Bz_{CAL-MEAS}$ may be scaled versions of the known amplitudes $Ax_{CAL-MEAS}$, $Ay_{CAL-MEAS}$, and $Az_{CAL-MEAS}$ of the directional components $Sx_{CAL-MEAS}$, $Sy_{CAL-MEAS}$, and $Sz_{CAL-MEAS}$ in accordance with a constant C2). The processor 58 may be configured for extracting the amplitudes $Ax_{CAL-MEAS}$, $Ay_{CAL-MEAS}$, and $Az_{CAL-MEAS}$ from the directional components $Sx_{CAL-MEAS}$, $Sy_{CAL-MEAS}$, and $Sz_{CAL-MEAS}$ of the signal $\vec{S}_{CAL-MEAS}$ at the calibration frequency $f_{CAL}$ using appropriate techniques, such as quadrature detection, Fourier transforms, or any equivalent signal processing method. Thus, the processor 58 need only compare the known amplitudes $Ax_{CAL-MEAS}$, $Ay_{CAL-MEAS}$, and $Az_{CAL-MEAS}$ of the signal $\vec{S}_{CAL-MEAS}$ output by the respective scalar magnetometers 52*x*, 52*y*, and 52*z* and the amplitude A of the current(s) output by the driver(s) 56 to determine the gains Gx, Gy, and Gz of the scalar magnetometers 52*x*, 52*y*, and 52*z*, in accordance with the following ratios:

$$Gx = \frac{Ax_{CAL-MEAS} \times C2}{A \times C1}; \quad [2a]$$

$$Gy = \frac{Ay_{CAL-MEAS} \times C2}{A \times C1}; \text{ and} \quad [2b]$$

$$Gz = \frac{Az_{CAL-MEAS} \times C2}{A \times C1}. \quad [2c]$$

Once the gains Gx, Gy, and Gz (as well as the offsets $Bx_0$, $By_0$, and $Bz_0$ acquired by pre-calibration techniques described in further detail below) of the scalar magnetometers 52*x*, 52*y*, and 52*z* for each of the coarse magnetometers 52 are known, they can be stored, and then subsequently recalled by the processor 58, during cancellation of the outside magnetic field $B_{OUT}$ (shown in FIG. 3), so that the processor 58 may properly determine the true total residual magnetic fields $B_{TOT}$ at the coarse magnetometers 52 respectively based on the total residual magnetic field measurements $B_{TOT-MEAS}$ reported by the coarse magnetometers 52 in accordance with the following ratios:

$$Bx_{TOT} = \frac{Bx_{TOT-MEAS}}{Gx} - Bx_0, \quad [3a]$$

$$By_{TOT} = \frac{By_{TOT-MEAS}}{Gy} - By_0; \text{ and} \quad [3b]$$

$$Bz_{TOT} = \frac{Bz_{TOT-MEAS}}{Gz} - Bz_0. \quad [3c]$$

As a result, the total residual magnetic field $B_{TOT}$ may be brought to zero or near-zero within the linear operating ranges of the fine magnetometers 26*b*, as discussed above. The processor 58 may periodically (e.g., every 5 minutes) in accordance with the calibration frequency $f_{CAL}$ to compensate for any gain drifts in the coarse magnetic sensors 26, that may occur due to, e.g., temperature changes, deformation of the support structure 24 to which the coarse magnetic sensors 26 are mounted, and other dynamic variations.

Thus, processor 58 may be configured for computing a ratio between the total residual magnetic field measurement $B_{TOT-MEAS}$ reported by a coarse magnetometer 52 and the gain G of the coarse magnetometer 52, computing the difference between the inherent gain offset $B_0$ of the coarse magnetometer and the computed ratio, and determining the amplitude of the total residual magnetic field $B_{TOT}$ at the coarse magnetometer 52 at least partially based on the computed difference.

In particular, in accordance with equations [3a]-[3c], the processor 58 is configured for computing ratios between the directional components $Bx_{TOT-MEAS}$, $By_{TOT-MEAS}$, and $Bz_{TOT-MEAS}$ of the total residual magnetic field measurement $\vec{B}_{TOT-MEAS}$ reported by the scalar magnetometers 52*x*, 52*y*, and 52*z* and the gains Gx, Gy, and Gz of the scalar magnetometers 52*x*, 52*y*, and 52*z*; computing the differences between the inherent gain offsets $Bx_0$, $By_0$, and $Bz_0$ of the scalar magnetometers 52*x*, 52*y*, and 52*z* and the computed ratios, and determining the amplitudes of the directional components $Bx_{TOT}$, $By_{TOT}$, and $Bz_{TOT}$ of the total residual magnetic field $\vec{B}_{TOT}$ based on computed differences.

Figure 9:
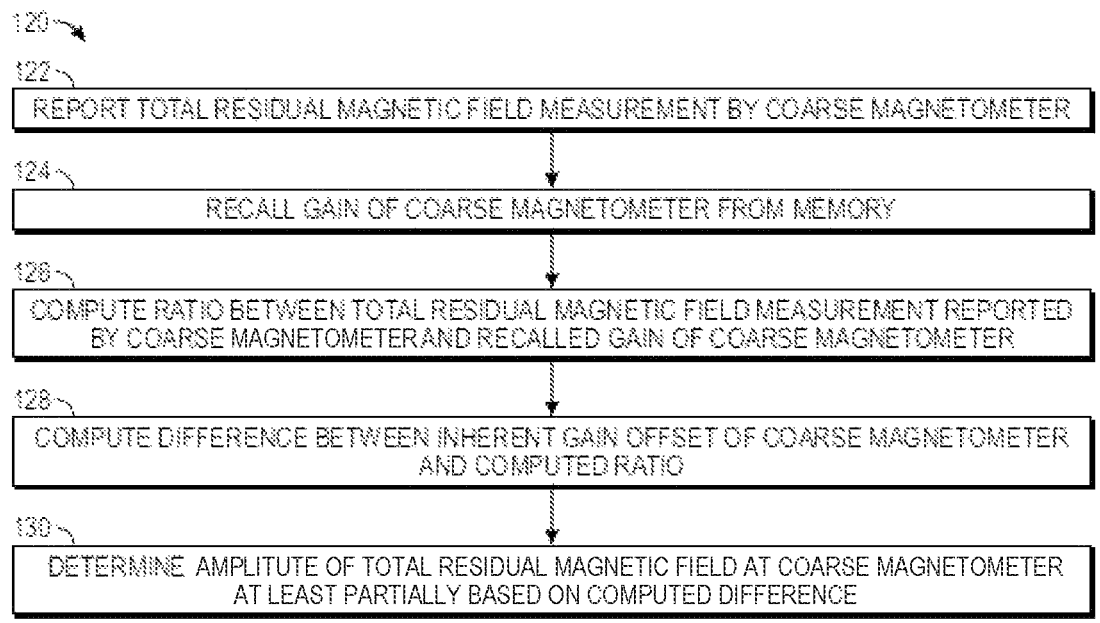
FIG. 9 is a flow diagram illustrating an exemplary method of operating a magnetometer calibration system for calibrating a gain of a coarse magnetometer in the calibration-enabled magnetometer assembly of FIG. 8A or FIG. 8B.

Referring now to FIG. 9, one exemplary method 120 for determining the total residual magnetic field $B_{TOT}$ at a coarse magnetometer 52 will be described.

The method 120 comprises reporting a total residual magnetic field measurement $B_{TOT-MEAS}$ by the coarse magnetometer 52, and in particular, reporting the directional components $Bx_{TOT-MEAS}$, $By_{TOT-MEAS}$, and $Bz_{TOT-MEAS}$ of the total residual magnetic field measurement $\vec{B}_{TOT-MEAS}$ by the scalar magnetometers 52*x*, 52*y*, and 52*z* (step 122).

The method 120 further comprises recalling the gain G of the coarse magnetometer 52 from memory, and in particular, recalling the gains Gx, Gy, and Gz of the scalar magnetometers 52*x*, 52*y*, and 52*z* from memory (step 124), and computing a ratio between the total residual magnetic field measurement $B_{TOT-MEAS}$ reported by the coarse magnetometer 52 and the recalled gain G of the coarse magnetometer 52, and in particular, computing ratios between the directional components $Bx_{TOT-MEAS}$, $By_{TOT-MEAS}$, and $Bz_{TOT-MEAS}$ of the total residual magnetic field measurement $\vec{B}_{TOT-MEAS}$ reported by the scalar magnetometers 52*x*, 52*y*, and 52*z* and the recalled gains Gx, Gy, and Gz of the scalar magnetometers 52*x*, 52*y*, and 52*z* (step 126).

The method 120 further comprises computing the difference between the inherent gain offset $B_0$ of the coarse magnetometer 52 and the computed ratio, and in particular, computing the differences between the inherent gain offsets $Bx_0$, $By_0$, and $Bz_0$ of the scalar magnetometers 52*x*, 52*y*, and 52*z* and the computed ratios (step 128).

The method 120 lastly comprises determining the amplitude of the total residual magnetic field $B_{TOT}$ at the coarse magnetometer 52 at least partially based on the computed difference, and in particular, determining the amplitudes of the directional components $Bx_{TOT}$, $By_{TOT}$, and $Bz_{TOT}$ of the total residual magnetic field $\vec{B}_{TOT}$ based on computed differences (step 130).

Significantly, accurate determination of the total residual magnetic field $B_{TOT}$ at the scalar magnetometers 52x, 52y, and 52z of each coarse magnetometer 52, and thus accurate cancellation of the outside magnetic field $B_{OUT}$ at the fine magnetometers, relies on the accurate quantification of the gains Gx, Gy, and Gz of the scalar magnetometers 52x, 52y, and 52z for each of the coarse magnetometers 52 at the frequencies at which the outside magnetic field $B_{OUT}$ will be cancelled, which in turn, relies on the accurate linear mapping of the defined amplitudes A of the current output by the set of calibration coils 54 and the directional components $Bx_{CAL}$, $By_{CAL}$, and $Bz_{CAL}$ of the true calibrating magnetic field $B_{CAL}$ at the scalar magnetometers 52x, 52y, and 52z of each coarse magnetometer 52, at the calibration frequency $f_{CAL}$, as well as the roll-off gain errors $Gx_{ROLL-OFF}$, $Gy_{ROLL-OFF}$, and $Gz_{ROLL-OFF}$ in the scalar magnetometers 52x, 52y, and 52z of each coarse magnetometer 52 due to roll-off effects in the gains of the scalar magnetometers 52x, 52y, and 52z between the lower cancellation frequencies and the higher calibration frequency $f_{CAL}$. Linear mapping between the set of calibration coils 54 and the scalar magnetometers 52x, 52y, and 52z of each coarse magnetometer 52 can be quantified as the gain $G_{COIL}$ of each set of calibration coils 54, which is affected by the frequency roll-off effects in the driver(s) 56 (the current source(s)) and manufacturing defects in the set of calibration coils 54, which may cause errors in the constant C1 in equations [2a]-[2c], whereas the roll-off gain errors $Gx_{ROLL-OFF}$, $Gy_{ROLL-OFF}$, and $Gz_{ROLL-OFF}$ in the scalar magnetometers 52x, 52y, and 52z cause frequency dynamic errors between the gains Gx, Gy, and Gz of the scalar magnetometers 52x, 52y, and 52z at the calibration frequency $f_{CAL}$ and the gains Gx, Gy, and Gz of the scalar magnetometers 52x, 52y, and 52z during cancellation of the outside magnetic field $B_{OUT}$.

If the calibration frequency $f_{CAL}$ is similar to the frequencies at which the outside magnetic field $B_{OUT}$ will be cancelled, frequency roll-off effects in the magnetometer calibration system 50 will be minimal, and thus, can be ignored. However, accurate quantification of the gains Gx, Gy, and Gz of the scalar magnetometers 52x, 52y, and 52z for each of the coarse magnetometers 52 also relies on the amplitude of the calibrating magnetic fields $\vec{B}_{CAL}$. In particular, it is preferred that the amplitude of the calibrating magnetic fields $\vec{B}_{CAL}$ be as high as possible, thereby increasing the signal-to-noise ratio (SNR) of the measured calibration signals $\vec{S}_{CAL-MEAS}$ output by the coarse magnetometers 52, and increasing the accuracy of the calibration procedure.

Figure 10:
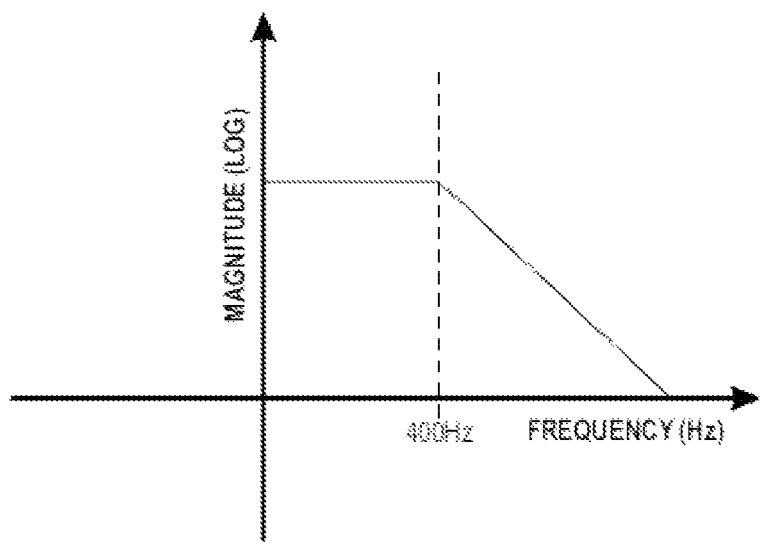
FIG. 10 is a diagram illustrating the bandwidth of an exemplary fine magnetometer used by the neural activity measurement system of FIG. 3 to finely cancel an outside magnetic field.

However, to avoid interference with the total residual magnetic field $B_{TOT}$ detected by the fine magnetometers 26b during dynamic calibration of the coarse magnetometers 52, it is also preferred that the calibration frequency $f_{CAL}$ lie far outside of the linear operating range of the fine magnetometers 26b. For example, FIG. 10 illustrates a typical first order frequency response of a fine magnetometer 26b, with the response being uniform across an operational frequency range (in this case, from 0 Hz to 400 Hz), and the response precipitously dropping off after this operational frequency range. Thus, in this case, the calibration frequency $f_{CAL}$ is preferably much greater than 400 Hz (e.g., 2K Hz), which may increase the frequency roll-off effects in the magnetometer calibration system 50.

The gain G of each set of calibration coils 54 and the roll-off effects of the magnetometer calibration system 50 may be quantified using a magnetometer pre-calibration system 70 that employs a novel pre-calibration technique (e.g., prior to affixing the coarse magnetometers 52 to the support structure 24 of the signal acquisition unit 18) to pre-calibrate the magnetometer calibration system 50 of FIG. 6.

Figure 11A:
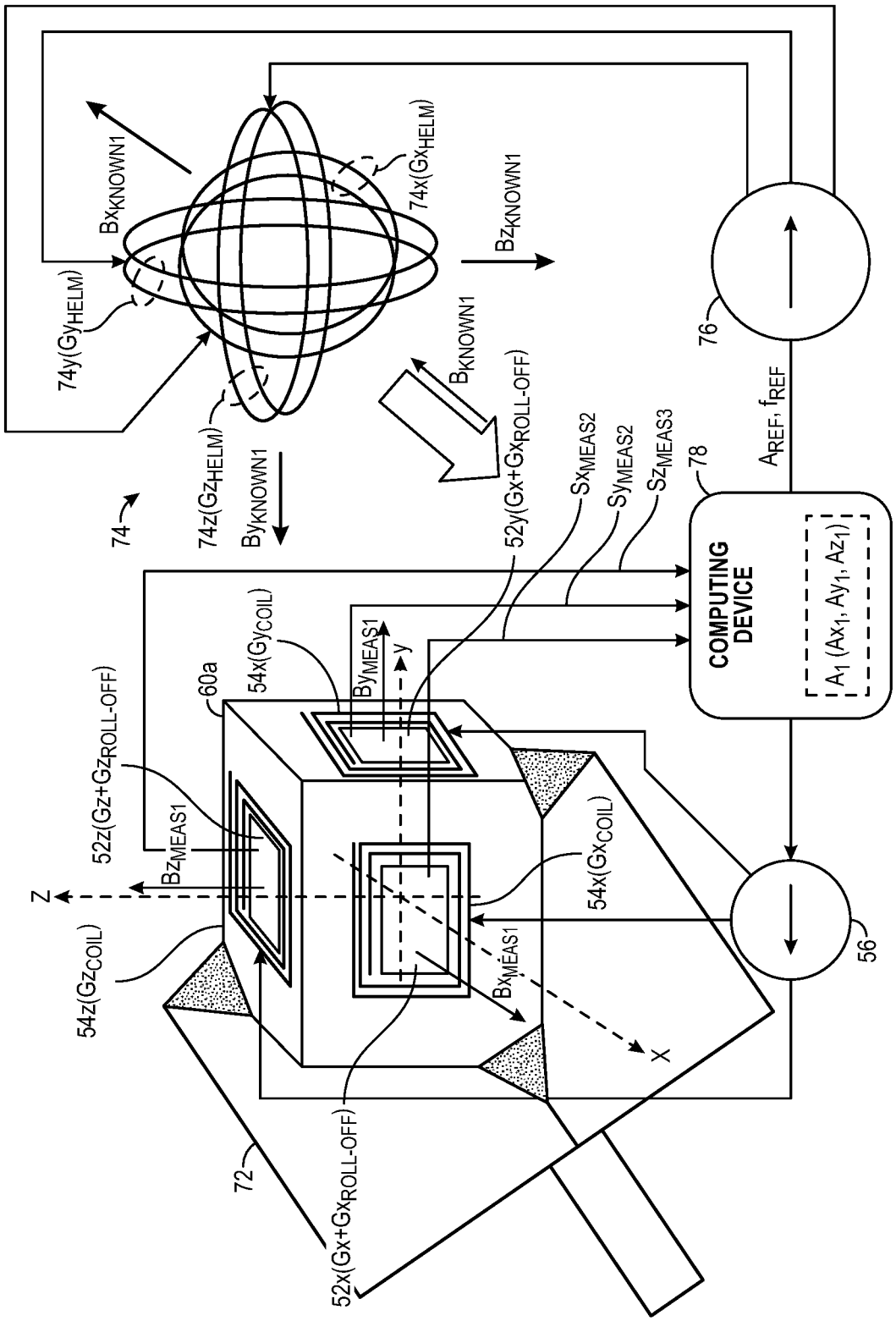
FIG. 11A is a block diagram illustrating a pre-calibration system constructed in accordance with one embodiment of the present inventions, particularly showing a first step performed to pre-calibrate the magnetometer calibration system of FIG. 6.
Figure 11B:
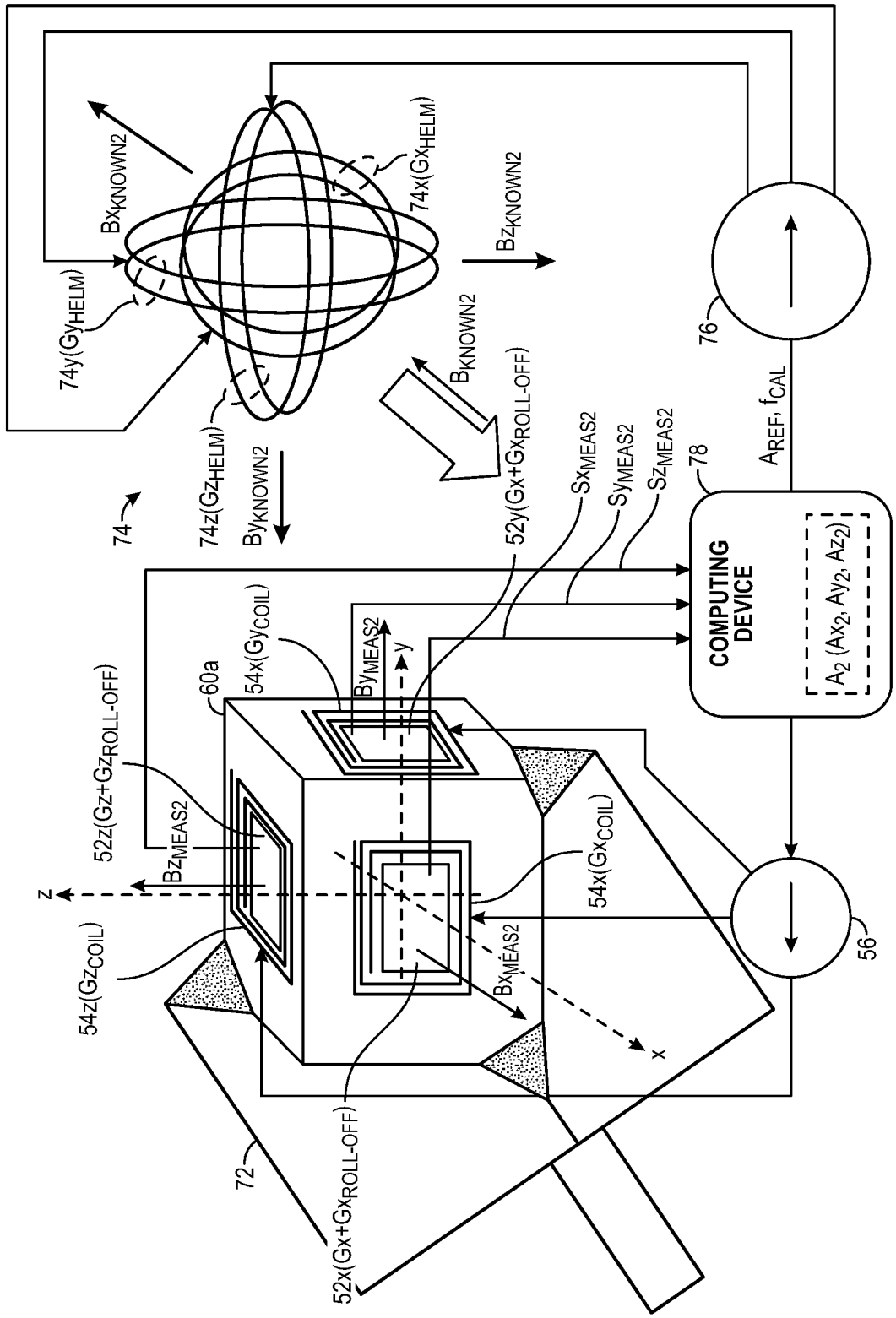
FIG. 11B is a block diagram illustrating the pre-calibration system of FIG. 11A, particularly showing a second step performed to pre-calibrate the magnetometer calibration system of FIG. 6.
Figure 11C:
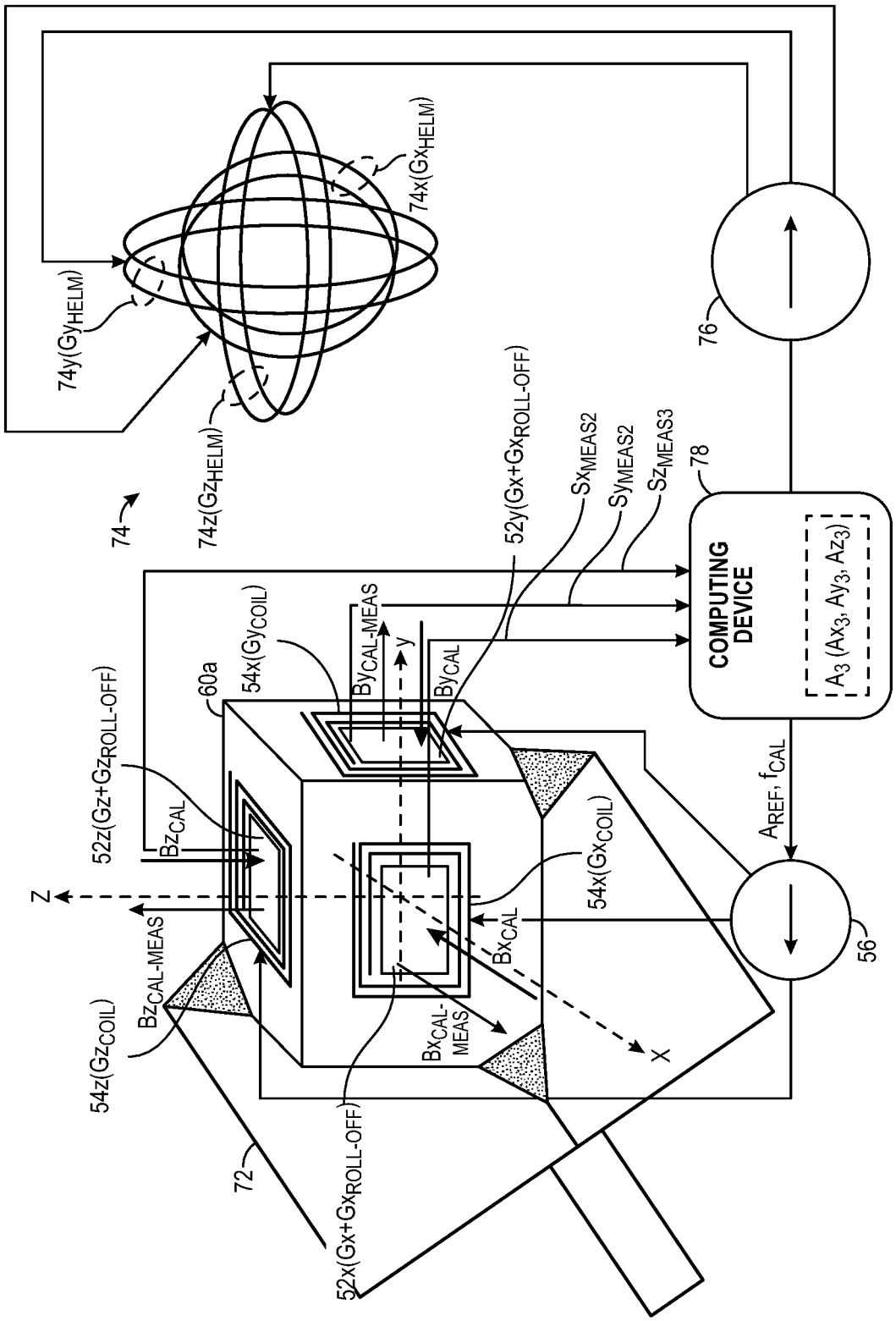
FIG. 11C is a block diagram illustrating the pre-calibration system of FIG. 11A, particularly showing a third step performed to pre-calibrate the magnetometer calibration system of FIG. 6.

In particular, and with reference to FIGS. 11A-11C, the pre-calibration system 70 comprises a pre-calibration test fixture 72, a set of pre-calibration coils 74, one or more drivers 76, and a computing device 78.

The pre-calibration test fixture 72 is configured for mechanically affixing one of the calibration-enabled magnetometer assemblies 60 in a stable position. In this case, the calibration-enabled magnetometer assembly 60a illustrated in FIG. 11A is affixed in the pre-calibration test fixture 72, although the calibration-enabled magnetometer assembly 60b illustrated in FIG. 11B can be alternatively affixed in the pre-calibration test fixture 72. In the illustrated embodiment, the set of pre-calibration coils 74 comprises a triad of pre-calibration coils 74x, 74y, and 74z is configured for generating a known uniform magnetic field having a vector $\vec{B}_{KNOWN}$ at the coarse magnetometer 52 of the mechanically stabilized calibration-enabled magnetometer assembly 60, preferably in three spatial dimensions (x, y, and z), such that the calibrating magnetic field $\vec{B}_{KNOWN}$ comprises directional components $Bx_{KNOWN}$, $By_{KNOWN}$, and $Bz_{KNOWN}$. Each of the pre-calibration coils 74x, 74y, and 74z may be any coil with known gains $Gx_{HELM}$, $Gy_{HELM}$, and $Gz_{HELM}$) capable of generating a spatially uniform magnetic field with a precisely known amplitude at the location of the coarse magnetometer 52 across a wide range of frequencies, e.g., a large Helmholtz coil. Although it is preferable that the set of pre-calibration coils 74 comprises a triad of pre-calibration coils 74x, 74y, and 74z to simplify the pre-calibration computations described below, in alternative embodiments, the set of pre-calibration coils 74 may comprise only one pre-calibration coil that may be oriented in a plurality of different direction, or may even be oriented in a single direction.

The computing device 78 can, e.g., be a computer, tablet, mobile device, or any other suitable device for processing information. The computing device 78 can be local to an operator or can include components that are non-local to an operator. For example, in at least some embodiments, the operator may operate a terminal that is connected to a non-local computing device. In other embodiments, the memory can be non-local to the user. The computing device 78 can utilize any suitable processor, including one or more hardware processors that may be local to the user or non-local to the operator or other components of the computing device 78, for executing instructions provided to the processor.

Any suitable memory can be used for the computing device 78. The memory can be a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal. The term "modulated data signal" can include a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display can be any suitable display device, such as a monitor, screen, or the like, and can include a printer. In some embodiments, the display is optional. In some embodiments, the display may be integrated into a single unit with the computing device 78, such as a tablet, smart phone, or smart watch. The input device can be, for example, a keyboard, mouse, touch screen, track ball, joystick, voice recognition system, or any combination thereof, or the like.

Although the functionality of the computing device 78 is described as being performed by a single component, such functionality may be distributed amongst several components.

Referring to FIG. 11A, the computing device 78 is configured for operating the driver(s) 76 to apply electrical current with a first known actuation strength $A_{REF1}$ (e.g., amperage, voltage, or some other variable) at a reference frequency $f_{REF}$ to the pre-calibration coils 74x, 74y, and 74z to generate a first magnetic field $B_1$ at the coarse magnetometer 52 of the calibration-enabled magnetometer assembly 60, and in particular, directional components $Bx_1$, $By_1$, and $Bz_1$ of a first magnetic field $B_1$ at the scalar magnetometers 52x, 52y, and 52z of the calibration-enabled magnetometer assembly 60. The reference frequency $f_{REF}$ is far below the frequency at which roll-off effects are expected in the magnetometer calibration system 50 (e.g., within the linear operating range of the coarse magnetometer 52 (e.g., 200 Hz).

In response, the coarse magnetometer 52 imperfectly measures the first magnetic field $B_1$ and reports the first magnetic field measurement $B_{MEAS1}$ as a first electrical signal $S_{MEAS1}$. In particular, the scalar magnetometers 52x, 52y, and 52z imperfectly measure the directional components $Bx_1$, $By_1$, and $Bz_1$ of the first known magnetic field $\vec{B_1}$, and reports the directional components $Bx_{MEAS1}$, $By_{MEAS1}$, and $Bz_{MEAS1}$ of the first magnetic field measurement $\vec{B_{MEAS1}}$ as directional components $Sx_{MEAS1}$, $Sy_{MEAS1}$, and $Sz_{MEAS1}$ of a first electrical signal $\vec{S_{MEAS1}}$.

Referring to FIG. 11B, at a separate time, the computing device 78 is configured for operating the driver(s) 76 to apply electrical current with a second known actuation strength $A_{REF2}$ (e.g., amperage, voltage, or some other variable) at a calibration frequency $f_{CAL}$ to the pre-calibration coils 74x, 74y, and 74z to generate a second magnetic field $B_2$ at the coarse magnetometer 52 of the calibration-enabled magnetometer assembly 60, and in particular, directional components $Bx_2$, $By_2$, and $Bz_2$ of a second magnetic field $B_2$ at the scalar magnetometers 52x, 52y, and 52z of the calibration-enabled magnetometer assembly 60.

In response, the coarse magnetometer 52 imperfectly measures the second magnetic field $B_2$ and reports the second magnetic field measurement $B_{MEAS2}$ as a second electrical signal $S_{MEAS2}$. In particular, the scalar magnetometers 52x, 52y, and 52z imperfectly measure the directional components $Bx_2$, $By_e$, and $Bz_2$ of the second known magnetic field $\vec{B_1}$, and reports the directional components $Bx_{MEAS2}$, $By_{MEAS2}$, and $Bz_{MEAS2}$ of the second magnetic field measurement $\vec{B_{MEAS2}}$ as directional components $Sx_{MEAS2}$, $Sy_{MEAS2}$, and $Sz_{MEAS2}$ of a second electrical signal $\vec{S_{MEAS2}}$. It can be assumed that, at the calibration $f_{CAL}$, there will be no roll-off effects reflected in the directional components $Bx_{MEAS2}$, $By_{MEAS2}$, and $Bz_{MEAS2}$ of the second magnetic field measurement $\vec{B_{MEAS2}}$ and thus, the directional components $Sx_{MEAS2}$, $Sy_{MEAS2}$, and $Sz_{MEAS2}$ of a second electrical signal $\vec{S_{MEAS2}}$.

Using appropriate techniques, such as quadrature detection, Fourier transforms, or any equivalent signal processing method, the calibration unit 58 is further configured for determining the amplitude $A_{MEAS1}$ of the first magnetic field measurement $B_{MEAS1}$ at the reference frequency $f_{REF}$ by extracting the amplitude from the first electrical signal $S_{MEAS1}$, and determining the amplitude $A_{MEAS2}$ of the second magnetic field measurement $B_{MEAS2}$ at the calibration frequency $f_{CAL}$ by extracting the amplitude from the second electrical signal $S_{MEAS2}$. In particular, the amplitudes $Ax_{MEAS1}$, $Ay_{MEAS1}$, and $Az_{MEAS1}$ of the directional components $Bx_{MEAS1}$, $By_{MEAS1}$, and $Bz_{MEAS1}$ of the first magnetic field measurement $\vec{B_{MEAS1}}$ are determined at the reference frequency $f_{REF}$ (see FIG. 11A) by extracting the amplitudes from the directional components $Sx_{MEAS1}$, $Sy_{MEAS1}$, and $Sz_{MEAS1}$ of the first electrical signal $\vec{S_{MEAS1}}$, and amplitudes $Ax_{MEAS2}$, $Ay_{MEAS2}$, and $Az_{MEAS2}$ of the directional components $Bx_{MEAS2}$, $By_{MEAS2}$, and $Bz_{MEAS2}$ of the second magnetic field measurement $\vec{B_{MEAS2}}$ are determined at the calibration frequency $f_{REF}$ (see FIG. 11B) by extracting the amplitudes from the directional components $Sx_{MEAS2}$, $Sy_{MEAS2}$, and $Sz_{MEAS2}$ of the second electrical signal $\vec{S_{MEAS1}}$.

The amplitudes $Ax_{MEAS1}$, $Ay_{MEAS1}$, and $Az_{MEAS1}$ of the directional components $Bx_{MEAS1}$, $By_{MEAS1}$, and $Bz_{MEAS1}$ of the first magnetic field measurement $\vec{B_{MEAS1}}$, as well as the amplitudes $Ax_{MEAS2}$, $Ay_{MEAS2}$, and $Az_{MEAS2}$ of the directional components $Bx_{MEAS2}$, $By_{MEAS2}$, and $Bz_{MEAS2}$ of the second magnetic field measurement $\vec{B_{MEAS2}}$ can be assumed to satisfy the equations:

$$Ax_{MEAS1} = A_{REF1} \times G_{HELM} \times Gx; \qquad [4a]$$

$$Ay_{MEAS1} = A_{REF1} \times G_{HELM} \times Gy; \qquad [4b]$$

$$Az_{MEAS1} = A_{REF1} \times G_{HELM} \times Gz; \qquad [4c]$$

$$Ax_{MEAS2} = A_{REF2} \times G_{HELM} \times Gx \times Gx_{ROLL-OFF}; \qquad [5a]$$

$$Ay_{MEAS2} = A_{REF2} \times G_{HELM} \times Gy \times Gy_{ROLL-OFF}; \text{ and} \qquad [5b]$$

$$Az_{MEAS2} = A_{REF2} \times G_{HELM} \times Gz \times Gz_{ROLL-OFF}; \qquad [5c]$$

where $A_{REF1}$ and $A_{REF2}$ are the first and second known amplitudes of the currents applied to the pre-calibration coils 74x, 74y, and 74z; $G_{HELM}$ is the known gain of each of the pre-calibration coils 74x, 74y, and 74z (which can be assumed to be the same between the pre-calibration coils 74x, 74y, and 74z at both at the reference frequency and the calibration frequency $f_{CAL}$, although in alternative embodiments, the gains between the pre-calibration coils 74x, 74y, and 74z at any particular frequency may differ from each other); Gx, Gy, and Gy are the unknown gains of the respective scalar magnetometers 52x, 52y, and 52z of the coarse magnetometer 52 to be calibrated; and $Gx_{ROLL-OFF}$, $Gy_{ROLL-OFF}$, and $Gz_{ROLL-OFF}$ are the gain errors of the respective scalar magnetometers 52x, 52y, and 52z of the coarse magnetometer 52 due to the roll-off effects at the calibration frequency $f_{cm}$.

Assuming that the first and second known amplitudes $A_{REF1}$ and $A_{REF2}$ applied to the pre-calibration coils 74x, 74y, and 74z are equal, the roll-off gain errors $Gx_{ROLL-OFF}$, $Gy_{ROLL-OFF}$, and $Gz_{ROLL-OFF}$ of the respective scalar magnetometers 52x, 52y, and 52z of the coarse magnetometer 52 can be obtained by respectively dividing equations [4a]-[4c] by equations [5a]-[5c], which yields the following ratios:

$$Gx_{ROLL-OFF} = \frac{Ax_{MEAS2}}{Ax_{MEAS1}}; \quad [6a]$$

$$Gy_{ROLL-OFF} = \frac{Ay_{MEAS2}}{Ay_{MEAS1}}; \text{ and} \quad [6b]$$

$$Gz_{ROLL-OFF} = \frac{Az_{MEAS2}}{Az_{MEAS1}}. \quad [6c]$$

Thus, the computing device 78 may be configured for computing a ratio between the amplitude $Ax_{MEAS1}$ of the first magnetic field measurement $B_{MEAS1}$ reported by the coarse magnetometer 52 and the amplitude $Ax_{MEAS2}$ of the second magnetic field measurement $B_{MEAS2}$ reported by the coarse magnetometer 52, and in particular, the ratios between the amplitudes $Ax_{MEAS1}$, $Ay_{MEAS1}$, and $Az_{MEAS1}$ of the directional components $Bx_{MEAS1}$, $By_{MEAS1}$, and $Bz_{MEAS1}$ of the first magnetic field measurement $\overrightarrow{B_{MEAS1}}$ and the amplitudes $Ax_{MEAS2}$, $Ay_{MEAS2}$, and $Az_{MEAS2}$ of the directional components $Bx_{MEAS2}$, $By_{MEAS2}$, and $Bz_{MEAS2}$ of the second magnetic field measurement $\overrightarrow{B_{MEAS2}}$ in accordance with the equations [6a]-[6c]. The computing device 78 may be further configured for determining the roll-off gain error $G_{ROLL-OFF}$ of the coarse magnetometer 52 at least partially based on the computed ratio, and in particular, roll-off gain errors $Gx_{ROLL-OFF}$, $Gy_{ROLL-OFF}$, and $Gz_{ROLL-OFF}$ of the respective scalar magnetometers 52x, 52y, and 52z of the coarse magnetometer 52 based on the computed ratios in accordance with equations [6a]-[6c].

Referring to FIG. 11C, preferably without delay (so as to avoid intermediate gain drifts in the coarse magnetometer 52), the computing device 78 is configured for operating the driver(s) 76 to apply electrical current with a third known actuation strength $A_{REF3}$ (e.g., amperage, voltage, or some other variable) (which may be different from the actual currents output by the driver(s) 56 due to roll-off effects in the set of driver(s) 56) at the calibration frequency $f_{CAL}$ to the set of calibration coils 54 to generate a third magnetic field $B_3$ at the coarse magnetometer 52 of the calibration-enabled magnetometer assembly 60, and in particular, directional components $Bx_3$, $By_3$, and $Bz_3$ of a third magnetic field $\overrightarrow{B_1}$ at the scalar magnetometers 52x, 52y, and 52z of the calibration-enabled magnetometer assembly 60.

In response, the coarse magnetometer 52 imperfectly measures the third magnetic field $B_3$ and reports the third magnetic field measurement $B_{MEAS1}$ as a first electrical signal $S_{MEAS1}$. In particular, the scalar magnetometers 52x, 52y, and 52z imperfectly measure the directional components $Bx_3$, $By_3$, and $Bz_3$ of the third known magnetic field $\overrightarrow{B_1}$, and reports the directional components $Bx_{MEAS3}$, $By_{MEAS3}$, and $Bz_{MEAS3}$ of the third magnetic field measurement $\overrightarrow{B_{MEAS1}}$ as directional components $Sx_{MEAS3}$, $Sy_{MEAS3}$, and $Sz_{MEAS3}$ of a third electrical signal $\overrightarrow{S_{MEAS3}}$.

Using appropriate techniques, such as quadrature detection, Fourier transforms, or any equivalent signal processing method, the calibration unit 58 is further configured for determining the amplitude $A_{MEAS3}$ of the third magnetic field measurement $B_{MEAS3}$ at the calibration frequency $f_{CAL}$ by extracting the amplitude from the electrical signal $S_{MEAS3}$. In particular, the amplitudes $Ax_{MEAS3}$, $Ay_{MEAS3}$, and $Az_{MEAS3}$ of the directional components $Bx_{MEAS3}$, $By_{MEAS3}$, and $Bz_{MEAS3}$ of the third magnetic field measurement $\overrightarrow{B_{MEAS3}}$ are determined at the calibration frequency $f_{CAL}$ (see FIG. 11C) by extracting the amplitudes from the directional components $Sx_{MEAS3}$, $Sy_{MEAS3}$, and $Sz_{MEAS3}$ of the third electrical signal $\overrightarrow{S_{MEAS3}}$.

The amplitude directional components $Ax_{MEAS3}$, $Ay_{MEAS3}$, and $Az_{MEAS3}$ of the directional components $Bx_{MEAS3}$, $By_{MEAS3}$, and $Bz_{MEAS3}$ of the third magnetic field measurement $\overrightarrow{B_{MEAS3}}$ can be assumed to satisfy the equations:

$$Ax_{MEAS3} = A_{REF3} \times Gx_{COIL} \times Gx \times Gx_{ROLL-OFF}; \quad [7a]$$

$$Ay_{MEAS3} = A_{REF3} \times Gy_{COIL} \times Gy \times Gy_{ROLL-OFF}; \text{ and} \quad [7b]$$

$$Az_{MEAS3} = A_{REF3} \times Gz_{COIL} \times Gz \times Gz_{ROLL-OFF}; \quad [7c]$$

where $A_{REF3}$ is the known amplitude of the current applied to the set of calibration coils 54; $Gx_{COIL}$, $Gy_{COIL}$, and $Gz_{COIL}$, are the unknown gains of the set of calibration coils 54 (whether the triad of calibration coils 54x, 52y, 52z (FIG. 8A) or the single calibration coil 54 (FIG. 8B)) corresponding to the directional components $Bx_{CAL}$, $By_{CAL}$, and $Bz_{CAL}$ of the calibrating magnetic field $\overrightarrow{B_{CAL}}$; Gx, Gy, and Gy are the unknown gains of the respective scalar magnetometers 52x, 52y, and 52z of the coarse magnetometer 52 to be calibrated; and $Gx_{ROLL-OFF}$, $Gy_{ROLL-OFF}$, and $Gz_{ROLL-OFF}$ are the solved gain errors (see equations [6a]-[6c]) of the respective scalar magnetometers 52x, 52y, and 52z of the coarse magnetometer 52 due to the roll-off effects at the calibration frequency $f_{CAL}$.

Assuming that the second and third known amplitudes $A_{REF2}$ and $A_{REF3}$ applied to the pre-calibration coils 74x, 74y, and 74z and set of calibration coils 54 are equal, the gains $Gx_{COIL}$, $Gy_{COIL}$, and $Gz_{COIL}$, of the set of calibration coils 54 can be obtained by respectively dividing equations [5a]-[5c] by equations [7a]-[7c], which yields the following ratios:

$$Gx_{COIL} = \frac{Ax_{MESS2} \times G_{HELM}}{Ax_{MEAS3}}; \quad [8a]$$

$$Gy_{COIL} = \frac{Ay_{MESS2} \times G_{HELM}}{Ay_{MESS3}}; \text{ and} \quad [8b]$$

$$Gz_{COIL} = \frac{Az_{MEAS2} \times G_{HELM}}{Az_{MEAS3}}. \quad [8c]$$

Thus, the computing device 78 may be configured for computing a product of the amplitude $Ax_{MEAS2}$ of the second magnetic field measurement $B_{MEAS2}$ reported by the coarse magnetometer 52 and the known gain $G_{HELM}$ of the set of pre-calibration coils 74, and computing a ratio between the computed product and the amplitude $Ax_{MEAS3}$ of the third magnetic field measurement $B_{MEAS3}$ reported by the magnetometer 52, and in particular, computing products of the amplitudes $Ax_{MEAS2}$, $Ay_{MEAS2}$, and $Az_{MEAS2}$ of the directional components $Bx_{MEAS2}$, $By_{MEAS2}$, and $Bz_{MEAS2}$ of the second magnetic field measurement $\vec{B}_{MEAS2}$ and the known gains $G_{HELM}$ of the pre-calibration coils 74x, 74y, and 74z, and computing ratios between the computed products and the amplitudes $Ax_{MEAS3}$, $Ay_{MEAS3}$, and $Az_{MEAS3}$ of the directional components $Bx_{MEAS3}$, $By_{MEAS3}$, and $Bz_{MEAS3}$ of the third magnetic field measurement $\vec{B}_{MEAS3}$ in accordance with the equations [8a]-[8c]. The computing device 78 may be further configured for determining the gain $G_{COIL}$ of the set of calibration coils 54 at least partially based on the computed ratio, and in particular, gains $Gx_{COIL}$, $Gy_{COIL}$, and $Gz_{COIL}$, of the set of coils 54 (whether the triad of calibration coils 54x, 52y, 52z (FIG. 8A) or the single calibration coil 54 (FIG. 8B)) based on the computed ratios in accordance with equations [8a]-[8c].

Figure 12:
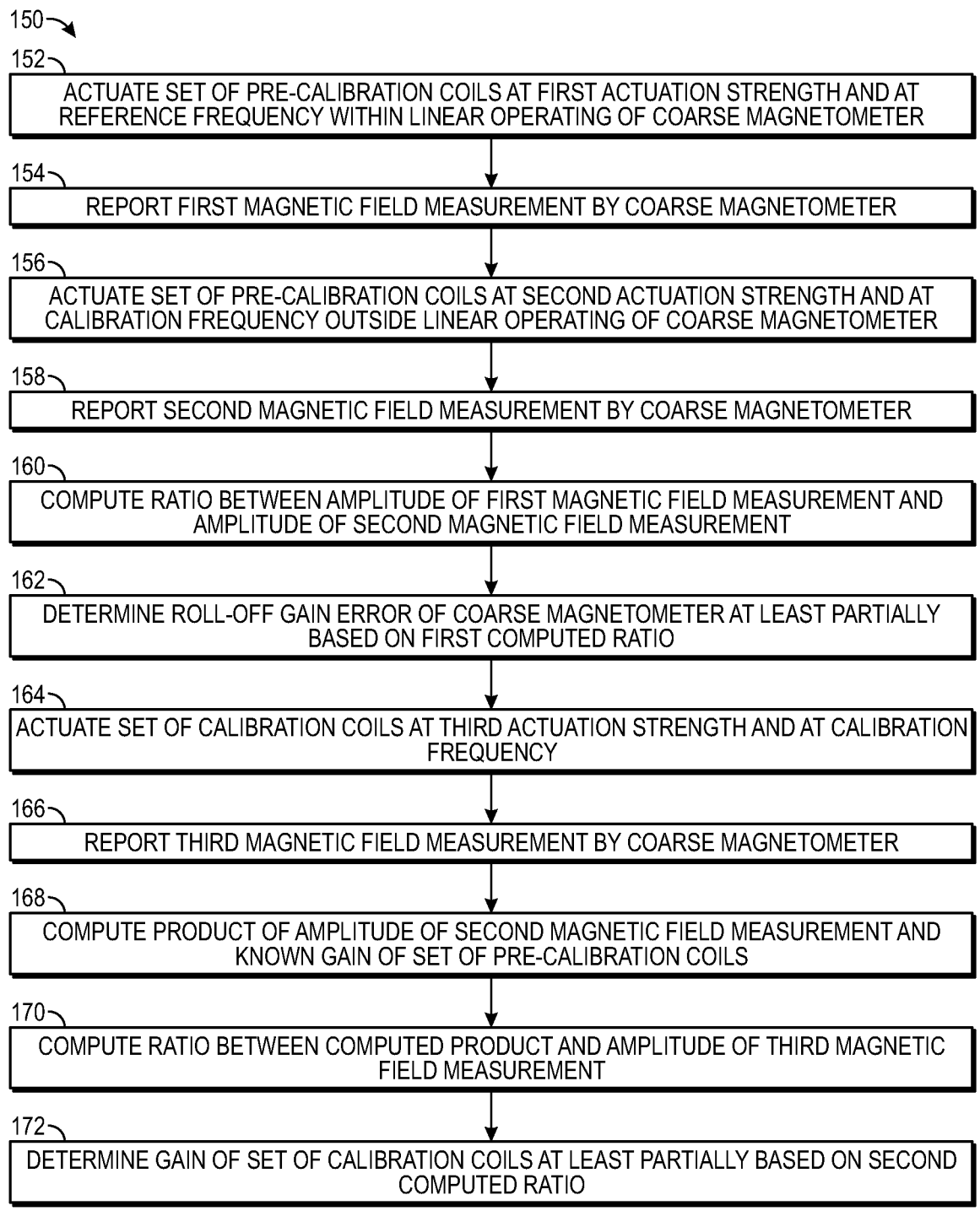
FIG. 12 is a flow diagram illustrating the pre-calibration system of FIG. 11A, particularly showing pre-calibration of a gain offset of a coarse magnetometer for use in the neural activity measurement system of FIG. 3.

Referring now to FIG. 12, one exemplary method 150 for pre-calibrating the gain roll-off gain error $G_{ROLL\text{-}OFF}$ and coil gain $G_{COIL}$ of a calibration-enabled magnetometer assembly 60 (see FIG. 8A or FIG. 8B) will be described.

The method 150 comprises actuating the set of pre-calibration coils 74 at a first actuation strength $A_{REF1}$ and at a reference frequency $f_{REF}$ within the linear operating range of the coarse magnetometer 52, such that the set of pre-calibration coils 74 generates a first magnetic field $B_1$ (step 152), and reporting a measurement of the first magnetic field $B_{MEAS1}$ by the magnetometer 52 (step 154). In the exemplary case, these steps are accomplished by actuating the pre-calibration coils 74x, 74y, and 74z at the first actuation strength $A_{REF1}$ and at the reference frequency $f_{REF}$, such that the calibration coils 74x, 74y, and 74z generate a first magnetic field $\vec{B}_1$ having directional components $Bx_1$, $By_1$, and $Bz_1$, and reporting measurements of the directional components $Bx_{MEAS1}$, $By_{MEAS1}$, and $Bz_{MEAS1}$ of the first magnetic field $\vec{B}_{MEAS1}$ by the scalar magnetometers 52x, 52y, and 52z.

The method 150 further comprises actuating the set of pre-calibration coils 74 at a second actuation strength $A_{REF2}$ (which may be the same as different from the first actuation strength $A_{REF1}$) and at a calibration frequency $f_{CAL}$ outside the linear operating range of the magnetometer 52, such that the set of pre-calibration coils 74 generates a second magnetic field $B_2$ (step 156), and reporting a measurement of the second magnetic field $B_{MEAS2}$ by the magnetometer 52 (step 158). In the exemplary case, these steps are accomplished by actuating the pre-calibration coils 74x, 74y, and 74z at the second actuation strength $A_{REF2}$ and at the calibration frequency $f_{CAL}$, such that the calibration coils 74x, 74y, and 74z generate a second magnetic field $\vec{B}_2$ having directional components $Bx_2$, $By_e$, and $Bz_2$, and reporting measurements of the directional components $Bx_{MEAS2}$, $By_{MEAS2}$, and $Bz_{MEAS2}$ of the second magnetic field $\vec{B}_{MEAS2}$ by the scalar magnetometers 52x, 52y, and 52z.

The method 150 further comprises computing a first ratio between an amplitude $A_{MEAS1}$ of the first magnetic field measurement $B_{MEAS1}$ reported by the magnetometer 52 and an amplitude $A_{MEAS2}$ of the second magnetic field measurement $B_{MEAS2}$ reported by the magnetometer 52 (step 160). In the exemplary case, this step is accomplished by computing ratios between amplitudes $Ax_{MEAS1}$, $Ay_{MEAS1}$, and $Az_{MEAS1}$ of the directional components $Bx_{MEAS1}$, $By_{MEAS1}$, and $Bz_{MEAS1}$ of the first magnetic field measurement $\vec{B}_{MEAS1}$ reported by the scalar magnetometers 52x, 52y, and 52z and amplitudes $Ax_{MEAS2}$, $Ay_{MEAS2}$, and $Az_{MEAS2}$ of the directional components $Bx_{MEAS2}$, $By_{MEAS2}$, and $Bz_{MEAS2}$ of the second magnetic field measurement $\vec{B}_{MEAS2}$ reported by the scalar magnetometers 52x, 52y, and 52z in accordance with equations [6a]-[6c].

The method 150 further comprises determining a roll-off gain error $G_{ROLL\text{-}OFF}$ of the coarse magnetometer 52 at least partially based on the first computed ratio (step 162), and storing the roll-off gain error $G_{ROLL\text{-}OFF}$ of the coarse magnetometer 52 in memory (step 164). In the exemplary case, these steps accomplished by determining roll-off gain errors $Gx_{ROLL\text{-}OFF}$, $Gy_{ROLL\text{-}OFF}$, and $Gz_{ROLL\text{-}OFF}$ of the scalar magnetometers 52x, 52y, and 52z at least partially based on the computed ratios in accordance with equation [6a]-[6c], and storing the roll-off gain errors $Gx_{ROLL\text{-}OFF}$, $Gy_{ROLL\text{-}OFF}$, and $Gz_{ROLL\text{-}OFF}$ of the scalar magnetometers 52x, 52y, and 52z in memory.

The method 150 further comprises actuating the set of calibration coils 54 of the calibration-enabled magnetometer assembly 60 at a third actuation strength $A_{REF3}$ (which may be the same as or different from the second actuation strength $A_{REF2}$) and at the calibration frequency $f_{CAL}$, such that the set of calibration coils 54 generates a third magnetic field $B_3$ (step 166), and reporting a measurement of the third magnetic field $B_{MEAS3}$ by the magnetometer 52 (step 168). In the exemplary case, these steps are accomplished by actuating the calibration coils 74x, 74y, and 74z of the calibration-enabled magnetometer assembly 60 at the third actuation strength $A_{REF3}$ and at the calibration frequency $f_{CAL}$, such that the calibration coils 54x, 54y, and 54z generate a third magnetic field $\vec{B}_3$ having directional components $Bx_3$, $By_3$, and $Bz_3$, and reporting measurements of the directional components $Bx_{MEAS3}$, $By_{MEAS3}$, and $Bz_{MEAS3}$ of the third magnetic field $\vec{B}_{MEAS3}$ by the scalar magnetometers 52x, 52y, and 52z.

The method 150 further comprises computing a product of the amplitude $A_{MEAS2}$ of the second magnetic field measurement $B_{MEAS2}$ reported by the magnetometer 52 and the known gain $G_{HELM}$ of the set of pre-calibration coils 74 (step 170), and computing a second ratio between the computed product and an amplitude $A_{MEAS3}$ of the third magnetic field measurement $B_{MEAS3}$ reported by the magnetometer 52 (step 172). In the exemplary case, these steps are accomplished by computing the products of the amplitudes $Ax_{MEAS2}$, $Ay_{MEAS2}$, and $Az_{MEAS2}$ of the directional components $Bx_{MEAS2}$, $By_{MEAS2}$, and $Bz_{MEAS2}$ of the second magnetic field measurement $\vec{B}_{MEAS2}$ reported by the scalar magnetometers 52x, 52y, and 52z and the known gains $G_{HELM}$ (which may be the same or different between the each other) of the pre-calibration coils 74x, 74y, 74z, and computing ratios between the computed products and amplitudes $Ax_{MEAS3}$, $Ay_{MEAS3}$, and $Az_{MEAS3}$ of the directional components $Bx_{MEAS3}$, $By_{MEAS3}$, and $Bz_{MEAS3}$ of the third magnetic field measurement $\vec{B}_{MEAS3}$ reported by the scalar magnetometers 52x, 52y, and 52z in accordance with equations [8a]-[8c].

The method 150 further comprises determining a gain $G_{COIL}$ of the set of calibration coils 54 at least partially based on the second computed ratio (step 176), and storing the $G_{COIL}$ of the set of calibration coils 54 in memory (step 178). In the exemplary case, these steps are accomplished by determining gains $Gx_{COIL}$, $Gy_{COIL}$, and $Gz_{COIL}$ of the set of calibration coils 54 (whether the triad of calibration coils 54x, 52y, 52z (FIG. 8A) or the single calibration coil 54 (FIG. 8B)) at least partially based on the computed ratios in accordance with equation [8a]-[8c], and storing the gains $Gx_{COIL}$, $Gy_{COIL}$, and $Gz_{COIL}$ of the set of calibration coils 54 in memory.

This pre-calibration procedure can be repeated by the calibration system 50 for each calibration-enabled magnetometer assembly 60 to quantify the roll-off error $G_{ROLL-OFF}$ of the coarse magnetometer 52 and the gain $G_{COIL}$ of the set of calibration coils 54, and in particular to quantify the roll-off gain errors $Gx_{ROLL-OFF}$, $Gy_{ROLL-OFF}$, and $Gz_{ROLL-OFF}$ of the scalar magnetometers 52x, 52y, and 52z and the gains $Gx_{COIL}$, $Gy_{COIL}$, and $Gz_{COIL}$, of the set of calibration coils 54, which generally will not change over time, and thus, can be stored by the processor 58 to facilitate dynamic calibration of the gain G of the coarse magnetometer 52, and in particular, the gains Gx, Gy, and Gz of the scalar magnetometers 52x, 52y, and 52z, for each calibration-enabled magnetometer assembly 60.

In particular, the processor 58 of the calibration system 50 is configured for operating the driver(s) 56 to apply electrical current with a known actuation strength A (e.g., amperage, voltage, or some other variable) at a calibration frequency $f_{CAL}$ to the set of calibration coils 54 (whether the triad of calibration coils 54x, 52y, 52z (FIG. 8A) or the single calibration coil 54 (FIG. 8B)) to generate the calibrating magnetic field $B_{CAL}$ at the coarse magnetometer 52 of the calibration-enabled magnetometer assembly 60, and in particular, directional components $Bx_{CAL}$, $B_{CAL}$, and $Bz_{CAL}$ of a calibrating magnetic field $\vec{B}_{CAL}$ at the scalar magnetometers 52x, 52y, and 52z of the calibration-enabled magnetometer assembly 60.

In response, the coarse magnetometer 52 measures the calibrating magnetic field $B_{CAL}$ and reports the calibrating magnetic field measurement $B_{CAL-MEAS}$ as a calibrating electrical signal $S_{CAL}$. In particular, the scalar magnetometers 52x, 52y, and 52z measure the directional components $Bx_{CAL}$, $B_{CAL}$, and $Bz_{CAL}$ of the calibrating magnetic field $\vec{B}_{CAL}$, and reports the directional components $Bx_{CAL-MEAS}$ $By_{CAL-MEAS}$, and $Bz_{CAL-MEAS}$ of the calibrating magnetic field measurement $\vec{B}_{CAL-MEAS}$ as directional components $Sx_{CAL-MEAS}$ $Sy_{CAL-MEAS}$, and $Sz_{CAL-MEAS}$ of a calibrating electrical signal $\vec{S}_{CAL-MEAS}$.

Using appropriate techniques, such as quadrature detection, Fourier transforms, or any equivalent signal processing method, the processor 58 is further configured for determining the amplitude $A_{CAL\_MEAS}$ of the calibrating magnetic field measurement $B_{CAL\_MEAS}$ at the reference frequency $f_{REF}$ by extracting the amplitude from the calibrating electrical signal $S_{CAL-MEAS}$. In particular, the amplitudes $Ax_{CAL-MEAS}$, $Ay_{CAL-MEAS}$, and $Az_{CAL\_MEAS}$ of the directional components $Bx_{CAL-MEAS}$, $By_{CAL-MEAS}$, and $Bz_{CAL\_MEAS}$ of the calibrating magnetic field measurement $\vec{B}_{CAL\_MEAS}$ are determined at the calibration frequency $f_{CAL}$ (see FIG. 6) by extracting the amplitudes from the directional components $Sx_{CAL-MEAS}$, $Sy_{CAL-MEAS}$, and $Sz_{CAL-MEAS}$ of the calibrating electrical signal $\vec{S}_{CAL-MEAS}$.

The amplitudes $Ax_{KNOWN}$, $Ay_{KNOWN}$, and $Az_{KNOWN}$ of the directional components $Bx_{CAL}$, $B_{CAL}$, and $Bz_{CAL}$ of the calibrating magnetic field $\vec{B}_{CAL}$ at the respective scalar magnetometers 52x, 52y, and 52z of a given coarse magnetometer 52 can be respectively estimated as follows:

$$Ax_{KNOWN} = A_{ACT} \times Gz_{COIL}; \quad [9a]$$

$$Ay_{KNOWN} = A_{ACT} \times Gy_{COIL}; \text{ and} \quad [9b]$$

$$Az_{KNOWN} = A_{ACT} \times Gz_{COIL}, \quad [9c]$$

where $A_{ACT}$ is the actuation strength applied by the set of drivers 56 to the calibration coils 54 and $Gx_{COIL}$, $Gy_{COIL}$, and $Gz_{COIL}$, are the gains of the set of calibration coils 54 for each calibration-enabled magnetometer assembly 52.

The amplitudes $Ax_{CAL-MEAS}$, $Ay_{CAL-MEAS}$, and $Az_{CAL-MEAS}$ representing the directional components $Bx_{CAL-MEAS}$, $By_{CAL-MEAS}$, and $Bz_{CAL-MEAS}$ of the calibrating magnetic field measurement $\vec{B}_{CAL-MEAS}$ reported by the respective scalar magnetometers 52x, 52y, and 52z of the coarse magnetometer 52 can be expressed as:

$$Ax_{CAL-MEAS} = Ax_{KNOWN} \times Gx \times Gx_{ROLL-OFF}; \quad [10a]$$

$$Ay_{CAL-MEAS} = Ay_{KNOWN} \times Gy \times Gy_{ROLL-OFF}; \quad [10b]$$

$$Az_{CAL-MEAS} = Az_{KNOWN} \times Gz \times Gz_{ROLL-OFF}. \quad [10c]$$

Solving equations [10a]-[10c] for the gains Gx, Gy, and Gy, yields the following ratios:

$$Gx = \frac{Ax_{CAL-MEAS}}{Ax_{KNOWN} \times Gx_{ROLL-OFF}}; \quad [11a]$$

$$Gy = \frac{Ay_{CAL-MEAS}}{Ay_{KNOWN} \times Gy_{ROLL-OFF}}; \text{ and} \quad [11b]$$

$$Gz = \frac{Az_{CAL-MEAS}}{Az_{KNOWN} \times Gz_{ROLL-OFF}}. \quad [11c]$$

Substituting the $Ax_{KNOWN}$, $Ay_{KNOWN}$, and $Az_{KNOWN}$ of equations [9a]-[9c] into equations [11a]-[11c] yields the following ratios:

$$Gx = \frac{Ax_{CAL-MEAS}}{A_{ACT} \times Gx_{COIL} \times Gx_{ROLL-OFF}}; \quad [12a]$$

$$Gy = \frac{Ay_{CAL-MEAS}}{A_{ACT} \times Gy_{COIL} \times Gy_{ROLL-OFF}}; \text{ and} \quad [12b]$$

$$Gz = \frac{Az_{CAL-MEAS}}{A_{ACT} \times Gz_{COIL} \times Gz_{ROLL-OFF}}. \quad [12c]$$

Since the defined actuation strength $A_{ACT}$ applied by the set of drivers 56 to the calibration coils 54, and the amplitudes $Ax_{CAL-MEAS}$, $Ay_{CAL-MEAS}$, and $Az_{CAL-MEAS}$ representing the directional components $Bx_{CAL-MEAS}$, By$_{CAL\text{-}MEAS}$, and Bz$_{CAL\text{-}MEAS}$ reported by scalar magnetometers 52x, 52y, and 52z of the coarse magnetometer 52 are known, and the roll-off gain errors Gx$_{ROLL\text{-}OFF}$, Gy$_{ROLL\text{-}OFF}$, and Gz$_{ROLL\text{-}OFF}$ of the respective scalar magnetometers 52x, 52y, and 52z of the coarse magnetometer 52 and gains Gx$_{COIL}$, Gy$_{COIL}$, and Gz$_{COIL}$ of the set of calibration coils 54 have been solved from equations [6a]-[6c] and [8a]-[8c] obtained during the pre-calibration technique and subsequently stored, the gains Gx, Gy, and Gy of the scalar magnetometers 52x, 52y, and 52z for each coarse magnetometer 52 can be determined.

Thus, the processor 58 of the calibration circuit 50 may be configured for computing a product of the known amplitude A$_{KNOWN}$ of the calibrating magnetic field B$_{CAL}$ at the coarse magnetometer 52 (i.e., the product of the known actuation strength A$_{ACT}$ at which the set of calibration coils 54 is actuated and the G$_{COIL}$ of the set of calibration coils 52) and the roll-off gain error G$_{ROLL\_OFF}$ of the coarse magnetometer 52, and computing a ratio between the amplitude A$_{CAL\_MEAS}$ of the calibrating magnetic field measurement B$_{CAL\_MEAS}$ reported by the coarse magnetometer 52 and the computed product. In particular, the processor 58 is configured for computing products of the known amplitudes Ax$_{KNOWN}$, Ay$_{KNOWN}$, and Az$_{KNOWN}$ of the directional components Bx$_{CAL}$, By$_{CAL}$, and Bz$_{CAL}$ of the calibrating magnetic field $\overrightarrow{B}_{CAL}$ at the scalar magnetometers 52, 52y, and 52z of the coarse magnetometer 52 (i.e., the product of the known actuation strength A$_{ACT}$ at which the set of calibration coils 54 is actuated and the gains Gx$_{COIL}$, Gy$_{COIL}$, and Gz$_{COIL}$ of the set of calibration coils 54, as shown in equations [9a]-[9c]) and the roll-off gain errors GX$_{ROLL\text{-}OFF}$, GY$_{ROLL\text{-}OFF}$ and Gz$_{ROLL\text{-}OFF}$ of the respective scalar magnetometers 52x, 52y, and 52z of the coarse magnetometer 52, and computing ratios between the amplitudes Ax$_{CAL\text{-}MEAS}$, Ay$_{CAL\text{-}MEAS}$, and Az$_{CAL\_MEAS}$ of the directional components Bx$_{CAL\text{-}MEAS}$, By$_{CAL\text{-}MEAS}$, and Bz$_{CAL\_MEAS}$ of the calibrating magnetic field measurement $\overrightarrow{B}_{CAL\text{-}MEAS}$reported by the respective scalar magnetometers 52x, 52y, and 52z of the coarse magnetometer 52 in accordance with equations [12a]-[12c].

The processor 58 may be further configured for determining the gain G of the set of calibration coils 54 at least partially based on the computed ratio, and in particular, gains Gx, Gy, and Gz of the set of scalar magnetometers 52x, 52y, 52z of the coarse magnetometer 52 based on the computed ratios in accordance with equations [12a]-[12c].

Figure 13:
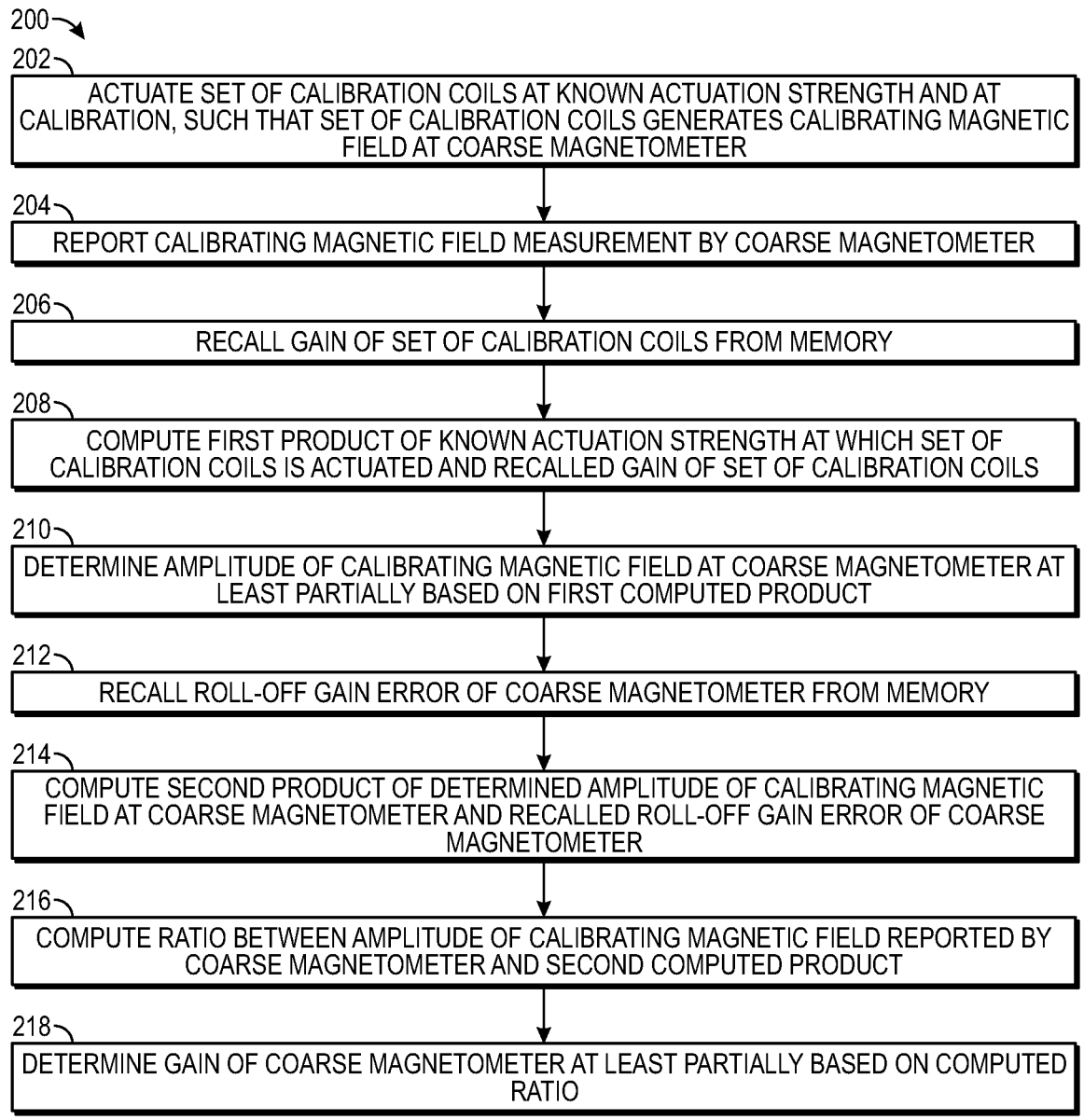
FIG. 13 is a flow diagram illustrating one exemplary method of operating the pre-calibration system of FIGS. 11A-11C to pre-calibrate roll-off gain errors in the coarse magnetometer of the calibration-enabled magnetometer assembly of FIG. 8A or FIG. 8B.

Referring now to FIG. 13, one exemplary method 200 for calibrating the gain G of a coarse magnetometer 52 of a calibration-enabled magnetometer assembly 60 will be described.

The method 200 comprises actuating the set of calibration coils 54 of the calibration-enabled magnetometer assembly 60 (whether the triad of calibration coils 54x, 52y, 52z (FIG. 8A) or the single calibration coil 54 (FIG. 8B)) at a known actuation strength A and at a calibration frequency f$_{CAL}$ (which is preferably outside of the linear operating range of the magnetometer 52), such that the set of calibration coils 54 generates a calibrating magnetic field B$_{CAL}$ at the magnetometer 52 (step 202), and reporting a measurement of the calibrating magnetic field B$_{CAL\text{-}MEAS}$ by the coarse magnetometer 52 (step 204). In the exemplary case, these steps are accomplished by actuating the set of calibration coils 54 at a known actuation strength A and at a calibration frequency f$_{CAL}$, such that the set of calibration coils 54 generates a calibrating magnetic field $\overrightarrow{B}_{CAL}$ having directional components Bx$_{CAL}$, B$_{CAL}$, and Bz$_{CAL}$ at the scalar magnetometers 52x, 52y, and 52z, and reporting measurements of the directional components Bx$_{CAL}$, B$_{CAL}$, and Bz$_{CAL}$ of the calibrating magnetic field $\overrightarrow{B}_{CAL}$ by the scalar magnetometers 52x, 52y, and 52z.

The method 200 further comprises recalling the gain G$_{COIL}$ of the set of calibration coils 54 from memory (step 206), computing a first product of the known actuation strength A at which the set of calibration coils 54 is actuated and the recalled gain G$_{COIL}$ of the set of calibration coils 54 (step 208), and determining the amplitude A$_{KNOWN}$ of the calibrating magnetic field B$_{CAL}$ at the magnetometer 52 at least partially based on the computed product (step 210). In the exemplary case, these steps are accomplished by recalling the gains Gx$_{COIL}$, Gy$_{COIL}$, and Gz$_{COIL}$ of the set of calibration coils 54 from memory, computing the product of the known actuation strength A at which the set of calibration coils 54 is actuated and the recalled gains Gx$_{COIL}$, Gy$_{COIL}$, and Gz$_{COIL}$ of the set of calibration coils 54, and determining the amplitudes Ax$_{KNOWN}$, Ay$_{KNOWN}$, and Az$_{KNOWN}$ of the directional components Bx$_{CAL}$, By$_{CAL}$, and Bz$_{CAL}$ of the calibrating magnetic field $\overrightarrow{B}_{CAL}$ at the scalar magnetometers 52, 52y, and 52z of the coarse magnetometer 52 at least partially based on the computed products in accordance with equations [9a]-[9c].

The method 200 further comprises recalling the roll-off gain error G$_{ROLL\text{-}OFF}$ of the coarse magnetometer 52 from memory (step 212), computing a second product of the determined amplitude A$_{KNOWN}$ of the calibrating magnetic field B$_{CAL}$ at the magnetometer 52 and the recalled roll-off gain error G$_{ROLL\text{-}OFF}$ of the coarse magnetometer 52 (step 214), computing a ratio between the amplitude A$_{CAL\text{-}MEAS}$ of calibrating magnetic field measurement B$_{CAL\text{-}MEAS}$ reported by the magnetometer 52 and the second computed product (step 216), and determining the gain G of a coarse magnetometer 52 at least partially based on the computed ratio (step 218). In the exemplary case, these steps are accomplished by recalling the roll-off gain errors Gx$_{ROLL\text{-}OFF}$, Gy$_{ROLL\text{-}OFF}$, and Gz$_{ROLL\text{-}OFF}$ of the scalar magnetometers 52, 52y, and 52z of the coarse magnetometer 52 from memory, computing ratios between amplitudes of Ax$_{CAL}$, Ay$_{CAL}$, and Az$_{CAL}$ of the directional components Bx$_{CAL\text{-}MEAS}$, By$_{CAL\text{-}MEAS}$, and Bz$_{MEAS}$ of the calibrating magnetic field measurement $\overrightarrow{B}_{CAL\text{-}MEAS}$ reported by the scalar magnetometers 52, 52y, and 52z of the coarse magnetometer 52 and the computed second products in accordance with equations [12a]-[12c].

Figure 14:
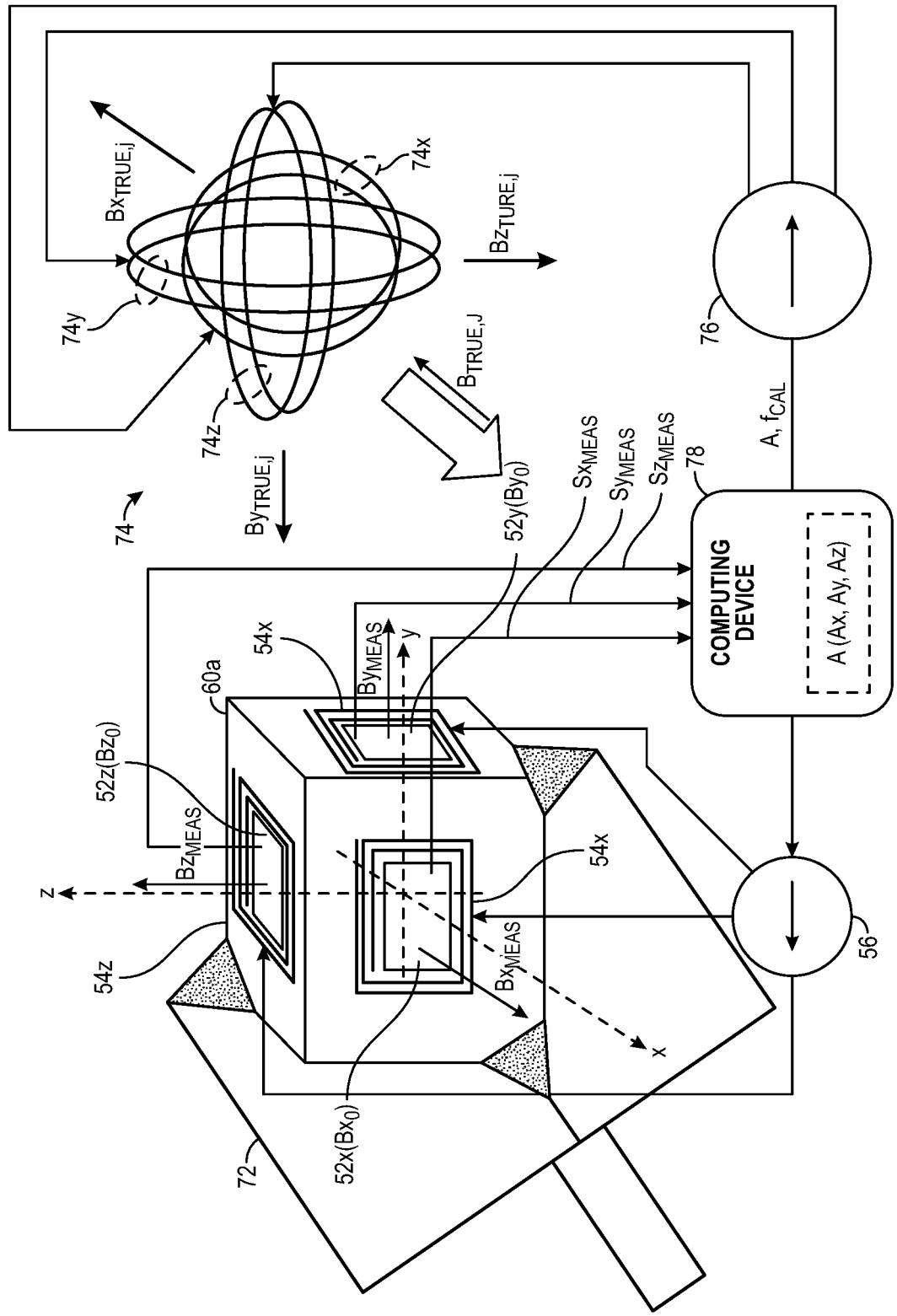
FIG. 14 is a block diagram illustrating the pre-calibration system of FIG. 11A, particularly showing pre-calibration of an inherent gain offset of a coarse magnetometer of magnetometer calibration system of FIG. 6.

Referring to FIG. 14, the pre-calibration system 70 is further configured for determining the inherent gain offsets (which may range in the tens of μT) of the scalar magnetometers 52x, 52y, and 52z in the coarse magnetometer 52 by rotating coarse magnetometer 52 around a point between the scalar magnetometers 52x, 52y, and 52z in the presence of a uniform magnetic field, in such a manner that the scalar magnetometers 52x, 52y, and 52z are essentially measuring the same magnetic field, and fitting the collected measurements to a sphere having a radius that represents the strength of the uniform magnetic field and a center that represents the estimate of an offset vector for the scalar magnetometers 52x, 52y, and 52z (i.e., an offset vector having an x-component corresponding to an intrinsic offset of the scalar magnetometers 52x, a y-component corresponding to an intrinsic offset of the scalar magnetometers 52y, and a z-component corresponding to an intrinsic offset of the scalar magnetometers 52z.

To this end, the pre-calibration test fixture 72 is configured for rotating (e.g., in response to control from the computing device 78 or another device) the calibration-enabled magnetometer assembly 60 (and thus, the coarse magnetometer 52) through an arbitrary number j of three-dimensional vector angles (to provide angular orientations $\theta_j$ and $\phi_j$) in three-dimensional space. Preferably, the calibration-enabled magnetometer assembly 60 are rotated about a point equi-distant between the scalar magnetometers 52x, 52y, and 52z, and the scalar magnetometers 52x, 52y, and 52z are spatially close enough in proximity to each other, such that the scalar magnetometers 52x, 52y, and 52z are virtually exposed to the same magnitude of a spatially uniform magnetic field.

Figure 15:
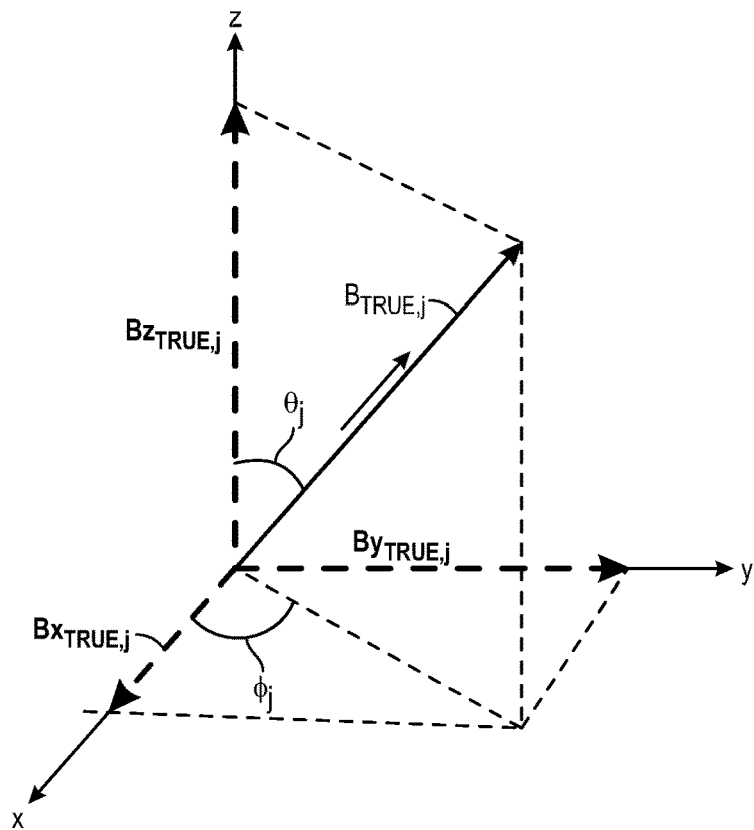
FIG. 15 is a diagram illustrating the generation of a true magnetic field by the pre-calibration system of FIG. 14 for pre-calibrating the inherent gain offset of the coarse magnetometer.

At each angle index j, the computing device 78 is configured for operating the triad of pre-calibration coils 74x, 74y, and 74z to apply a true magnetic field (in this case, a pre-calibrating magnetic field) having a vector $\vec{B}_{TRUE,j}$ with a constant amplitude A and at the calibration frequency $f_{CAL}$ or alternatively, another frequency) to the coarse magnetometer 52 of the calibration-enabled magnetometer assembly 60; that is, the directional components $Bx_{TRUE,j}$, $By_{TRUE,j}$, and $Bz_{TRUE,j}$ of the true magnetic field $\vec{B}_{TRUE,j}$ are applied to the scalar magnetometers 52x, 52y, and 52z. The pre-calibration coils 74x, 74y, and 74z can be actuated to continuously apply the exterior magnetic field to the coarse magnetometer 52 coincidentally with the rotation of the coarse magnetometer 52 through the number j of vector angles, or discretely in response to the rotation of the coarse magnetometer 52 to each vector angle. Thus, as illustrated in FIG. 15, at each angle index j, the true magnetic field $\vec{B}_{TRUE,j}$ has an angular orientation relative to the coarse magnetometer 52, which can be defined by the angular orientations $\theta_j$ and $\phi_j$, such that, in accordance with standard trigonometric functions, directional components $Bx_{TRUE,j}$, $By_{TRUE,j}$, and $Bz_{TRUE,j}$ of the magnetic field $\vec{B}_{TRUE,j}$ can be defined as:

$$Bx_{TRUE,j} = B_{TRUE} \sin \theta_j \cos \phi_j;\quad [13a]$$

$$By_{TRUE,j} = B_{TRUE} \sin \theta_j \sin \phi_j; \text{ and}\quad [13b]$$

$$Bz_{TRUE,j} = B_{TRUE} \cos \theta_j;\quad [13c]$$

In response to the application of the directional components $Bx_{TRUE,j}$, $By_{TRUE,j}$, and $Bz_{TRUE,j}$ of the magnetic field $\vec{B}_{TRUE}$ to the scalar magnetometers 52x, 52y, and 52z at each vector angle, scalar magnetometers 52x, 52y, and 52z of the coarse magnetometer 52 respectively detects the directional components $Bz_{TRUE,j}$, $By_{TRUE,j}$, and $Bz_{TRUE,j}$ of the magnetic field $\vec{B}_{TRUE}$, and outputs a signal having a vector $\vec{S}_{MEAS}$ (i.e., $Sx_{MEAS}$, $Sy_{MEAS}$, and $Sz_{MEAS}$) representative of directional components $Bx_{MEAS}$, $By_{MEAS}$, and $Bz_{MEAS}$ of a measured magnetic field $\vec{B}_{MEAS}$. The processor 58 may derive the directional components $Bx_{MEAS}$, $By_{MEAS}$, and $Bz_{MEAS}$ of the measured magnetic field $\vec{B}_{CAL-MEAS}$ at the scalar magnetometers 52x, 52y, and 52z from the signals $Sx_{MEAS}$, $Sy_{MEAS}$, and $Sz_{MEAS}$ output by the respective scalar magnetometers 52x, 52y, and 52z using linear mapping; that is, the amplitudes of the directional components $Bx_{MEAS}$, $By_{MEAS}$, and $Bz_{MEAS}$ of the measured magnetic field $\vec{B}_{MEAS}$ at the scalar magnetometers 52x, 52y, and 52z linearly scale with the currents of the signals $Sx_{MEAS}$, $Sy_{MEAS}$, and $Sz_{MEAS}$ output by the scalar magnetometers 52x, 52y, and 52z. Using appropriate techniques, such as quadrature detection, Fourier transforms, or any equivalent signal processing method, the computing device 78 is configured for determining the amplitude A of the measured signal $\vec{S}_{MEAS}$ (i.e., the amplitude components Ax, Ay, and Az of the directional components $Sx_{MEAS}$, $Sy_{MEAS}$, and $Sz_{MEAS}$) at the calibration frequency $f_{CAL}$.

The scalar magnetometers 52x, 52y, and 52z respectively have inherent offsets $Bx_0$, $By_0$, and $Bz_0$, such that, assuming that the gains Gx, Gy, and Gz of the scalar magnetometers 52x, 52y, and 52z have been properly calibrated by the computing device 78 (in the same manner described above with respect to the processor 58), the directional components $Bx_{MEAS}$, $By_{MEAS}$, and $Bz_{MEAS}$ of the measured magnetic field $\vec{B}_{MEAS}$ at the scalar magnetometers 52x, 52y, and 52z (as derived from the gain calibrated signals $Sx_{MEAS}$, $Sy_{MEAS}$, and $Sz_{MEAS}$ output by the scalar magnetometers 52x, 52y, and 52z) will be as follows for any particular index j of the rotational angle:

$$Bx_{MEAS,j} = Bx_{TRUE,j} + Bx_0 = B_{TRUE} \sin \theta_j \cos \phi_j + Bx_0;\quad [14a]$$

$$By_{MEAS,j} = By_{TRUE,j} + Bx_0 = B_{TRUE} \sin \theta_j \sin \phi_j Bx_0; \text{ and}\quad [14b]$$

$$Bz_{MEAS,j} = Bz_{TRUE,j} + Bx_0 = B_{TRUE} \cos \theta_j + Bx_0\quad [14c]$$

Assuming $\vec{B}_j$ and $\vec{B}_0$ denote the vectors holding the entries $(Bx_{MEAS,j}, By_{MEAS,j}, Bz_{MEAS,j})$ and $(Bx_0, By_0, Bz_0)$, respectively, these vectors then satisfy the following equation:

$$\|\vec{B}_j - \vec{B}_0\|^2 = B_{TRUE}^2,\quad [15]$$

where $\|\cdot\|^2$ denotes the squared norm of a vector. It should be appreciated that equation [15] is the equation for a sphere:

$$(\vec{p} - \vec{C})^2 = R^2,\quad [16]$$

where $\vec{p}$ represents the points on the sphere in the Cartesian coordinate system (x, y, and z), and corresponds to $\vec{B}_J$ in equation [15]; $\vec{C}$ is the center of the sphere in the Cartesian coordinate system, and corresponds to $\vec{B}_J$ in equation; and R is the radius of the sphere and corresponds to $B_{TRUE}$ in equation [15]. Expanding equation [15] yields:

$$Bx_{MEAS,j}^2 - 2Bx_{MEAS,j}Bx_0Bx_0 + Bx_0^2 + By_{MEAS,j}^2 - 2By_{MEAS,j}By_0 + By_0^2 + Bz_{MEAS,j}^2 - 2Bz_{MEAS,j}Bz_0 + Bz_0^2 - B_{TRUE}^2 = 0,\quad [17]$$

which can be regrouped as follows:

$$Bx_{MEAS,j}^2 + By_{MEAS,j}^2 + Bz_{MEAS,j}^2 = 2Bx_{MEAS,j}Bx_{MEAS,j}Bx_0 + 2By_{MEAS,j}By_0 + 2Bz_{MEAS,j}Bz_0 + (B_{TRUE}^2 - Bx_0^2 - By_0^2 - Bz_0^2).\quad [18]$$

If the calibration-enabled magnetometer assembly 60 (and thus, the coarse magnetometer 52) is rotated through at least four three-dimensional vector angles (i.e., angular orientations $\theta_{j-n}$ and $\phi_{j-n}$ in three-dimensional space, where n is at least four) relative to the true magnetic field $\vec{B}_{TRUE}$ then equation [17] can be used to estimate the unknown offsets $Bx_0$, $By_0$, and $Bz_0$ and the squared true magnetic field $B_{TRUE}^2$.

In an exemplary case, the unknown offsets $Bx_0$, $By_0$, and $Bz_0$ and the squared true magnetic field $B_{TRUE}^2$ can be estimated using a least squares or by weighted least squares technique, although other estimation techniques, such as, e.g., Wiener filters, and other optimization methods, such as gradient descent, matrix methods, linear programming, nonlinear programming, neural networks, fuzzy algorithms, or any other technique that one of ordinary skilled in the art of system identification, control, or optimization will recognize will have an essentially equivalent outcome, can be used.

For example, in a least squares approximation, let $A_j = (2Bx_{MEAS,j}, 2By_{MEAS,j}, 2Bz_{MEAS,j}, 1)$ denote the jth row of a matrix, and $b_j = Bx_{MEAS,j}^2 + By_{MEAS,j}^2 + Bz_{MEAS,j}^2$ denote the jth entry of a column vector, such that there is one row in the matrix for every measurement (or angular orientation) j. Then the least squares solution for a variable x in the linear matrix equation:

$$A x = b \quad [19]$$

will contain a least squares estimate for the four components $(b_j = Bx_{MEAS,j}^2 + By_{MEAS,j}^2 + Bz_{MEAS,j}^2)$ from which an estimate for the four unknowns $Bx_0$, $By_0$, $Bz_0$, and $B_{TRUE}^2$ can be obtained. It should be appreciated that grouping all of the square terms as the quantity $B_{TRUE}^2 - Bx_0^2 - By_0^2 - Bz_0^2$ as one of the unknown variables renders the estimation problem linear. This represents a significant reduction in complexity and allows well-known tools from linear algebra to be used to estimate the unknowns, despite the fact that the unknowns ($Bx_0$, $By_0$, $Bz_0$, $B_{TRUE}$) appear in nonlinear terms in the original formulation set forth in equation [17] above.

Although each of the coarse magnetometers 52 may have a gain offset $B_0$ in the tens of μT, such gain offsets $B_0$ can be estimated using the calibration technique described above with an accuracy of a few hundred nT, due mainly to the fact that the triad of scalar magnetometers 52x, 52y, and 52z are not exactly co-located at the same point, and thus, only approximately experience the same magnetic field. Thus, this calibration technique provides a benefit of approximately 100 times (from tens of pT to hundreds of nT).

It should be appreciated that, although the pre-calibration system 70 has been described as determining the inherent offsets $Bx_0$, $By_0$, and $Bz_0$ of the scalar magnetometers 52x, 52y, and 52z affixed within a calibration-enabled magnetometer assembly 60, the pre-calibration system 70 can be modified to determine the inherent offsets $Bx_0$, $By_0$, and $Bz_0$ of any triad of scalar magnetometers 52x, 52y, and 52z mutually orthogonally arranged relative to each other. For example, the calibration coils 54x, 54y, and 54z can be placed in proximity to the respective scalar magnetometers 52x, 52y, and 52z without the use of a fixture 62 that integrates the calibration coils 54x, 54y, and 54z and scalar magnetometers 52x, 52y, and 52z together, e.g., by affixing the calibration coils 54x, 54y, and 54z directly to the test fixture 72 in proximity to the respective scalar magnetometers 52x, 52y, and 52z.

Figure 16:
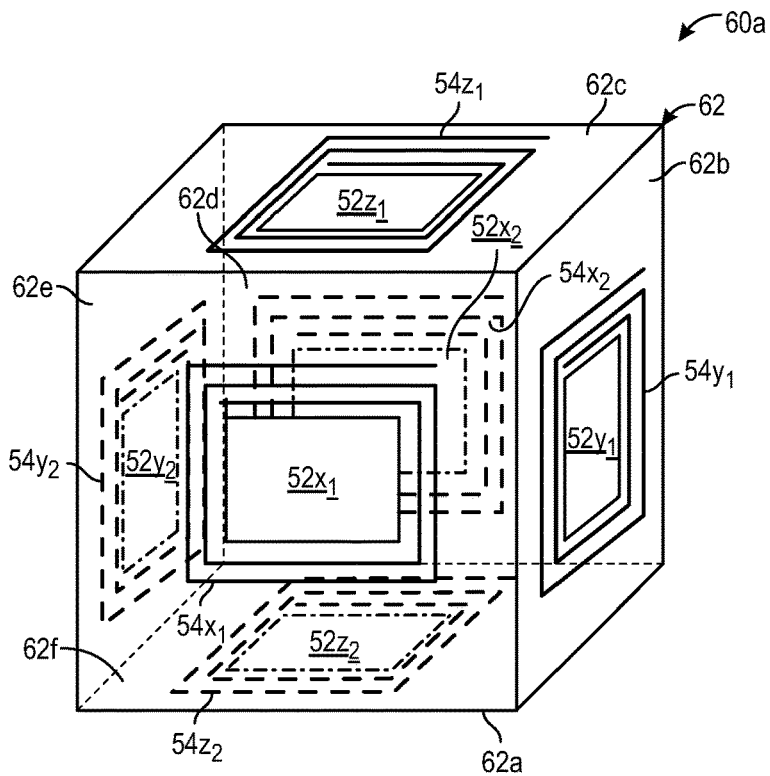
FIG. 16 is a perspective view of still another embodiment of a calibration-enabled magnetometer assembly constructed in accordance with the present inventions, and for use in the magnetometer calibration system of FIG. 5.

Furthermore, although the pre-calibration system 70 has been described as determining the inherent offsets $Bx_0$, $By_0$, and $Bz_0$ of only three scalar magnetometers 52x, 52y, and 52z, it should be appreciated that the pre-calibration system 70 may be modified to determining the inherent offsets $Bx_0$, $By_0$, and $Bz_0$ of multiple subsets of an arbitrary number of scalar magnetometers 52 as long each subset comprises a triad of three scalar magnetometers 52 mutually orthogonally arranged relative to each other. For example, two parallel scalar magnetometers $52x_1$, $52x_2$ with two parallel calibration coils $54x_1$, $52x_2$ may be affixed to opposite faces 62a, 62d of the fixture 62, two parallel scalar magnetometers $52y_1$, $52y_2$ with two parallel calibration coils $54y_1$, $52y_2$ may be affixed to opposite faces 62b, 62e of the fixture 62, and two parallel scalar magnetometers $52z_1$, $52z_2$ with two parallel calibration coils $54z_1$, $52z_2$ may be affixed to opposite faces 62c, 62f of the fixture 62, as illustrated in FIG. 16. Permutations of different triads of the scalar magnetometers 52 may be calibrated together. For example, first triad of scalar magnetometers $52x_1$, $52y_1$, $52z_1$ may be calibrated together; a second different triad of scalar magnetometers $52x_2$, $52y_2$, $52z_2$; a third different triad of scalar magnetometers $52x_1$, $52y_2$, $52z_1$ may be calibrated together; a four a third different triad of scalar magnetometers $52x_1$, $52y_2$, $52z_2$, and so forth.

It should also be appreciated that, while it is preferred for a triad of the scalar magnetometers 52 to be mutually orthogonally arranged relative to each other in order to minimize the complexity of steps in estimating the unknowns ($Bx_0$, $By_0$, $Bz_0$, $B_{TRUE}$), the triad of scalar magnetometers 52 may be mutually non-orthogonally arranged relative to each other as long as the scalar magnetometers 52 span three dimensions (i.e., linearly dependent). In this case, the matrix A acquired from the measured signal $\vec{S}_{MEAS}$ output by the non-orthogonally arranged scalar magnetometers 52 will not be Cartesian, and thus, must be transformed into a Cartesian matrix A' prior to estimating the variable x (i.e., $Bx_0$, $By_0$, $Bz_0$, $B_{TRUE}$) in equation [18]. The estimated variable x must then be transformed back into the non-orthogonal coordinate system defined by the mutually non-orthogonally arranged triad of scalar magnetometers 52.

Figure 17:
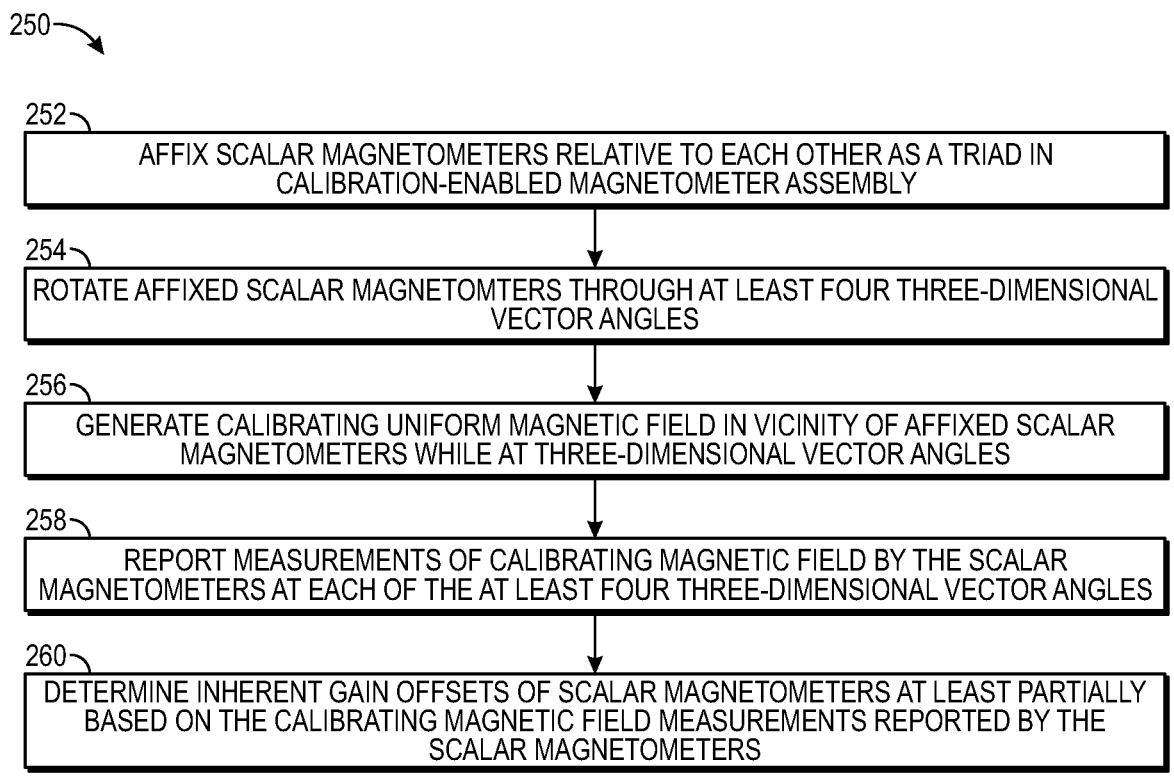
FIG. 17 is a flow diagram illustrating one exemplary method of operating the pre-calibration system of FIG. 14 to pre-calibrate an inherent gain offset of the coarse magnetometer of the calibration-enabled magnetometer assembly of FIG. 8A or FIG. 8B.

Referring now to FIG. 17, one exemplary method 250 of calibrating the inherent gain offsets $Bx_0$, $By_0$, $Bz_0$ of the scalar magnetometers 52x, 52y, and 52z will be described. It should be appreciated that, although the method 250 is described as calibrating inherent gain offsets $Bx_0$, $By_0$, $Bz_0$ of the scalar magnetometers 52x, 52y, and 52z, the method 250 can be applied to any type and number of magnetometers that number at least three.

The method 250 comprises affixing the scalar magnetometers 52x, 52y, and 52z relative to each other (preferably in a substantially co-located arrangement), such that the scalar magnetometers 52x, 52y, and 52z are oriented in at least three different directions (step 252). For example, the scalar magnetometers 52x, 52y, and 52z may be affixed as a triad in one of the calibration-enabled magnetometer assemblies 60a, 60b illustrated in FIGS. 8A and 8B.

The method further comprises rotating the affixed magnetometers 52x, 52y, and 52z (and in this exemplary case, the calibration-enabled magnetometer assembly 60) through at least four three-dimensional vector angles (step 254), generating a calibrating uniform magnetic field measurement $\vec{B}_{TRUE}$ in the vicinity of the affixed scalar magnetometers 52x, 52y, and 52z while at the three-dimensional vector angles (step 256), and reporting measurements of the orthogonal directional components $Bx_{TRUE\text{-}MEAS}$, $By_{TRUE\text{-}MEAS}$, and $Bz_{TRUE\text{-}MEAS}$ of the calibrating uniform magnetic field $\vec{B}_{TRUE\text{-}MEAS}$ by the affixed magnetometers 52x, 52y, and 52z at each of the three-dimensional vector angles (step 258). The amplitudes of the directional components $Bx_{TRUE\text{-}MEAS}$, $By_{TRUE\text{-}MEAS}$, and $Bz_{TRUE\text{-}MEAS}$ of the calibrating uniform magnetic field measurements $\vec{B}_{TRUE\text{-}MEAS}$ reported by the scalar magnetometers 52x, 52y, and 52z may be adjusted in accordance with the gains Gx, Gy, and Gz of the scalar magnetometers 52x, 52y, and 52z, which may be determined using the calibration method 200 of FIG. 13.

The method 250 lastly comprises determining the inherent gain offsets $Bx_0$, $By_0$, $Bz_0$ of the scalar magnetometers 52x, 52y, and 52z based on the directional components $Bx_{TRUE\text{-}MEAS}$, $By_{TRUE\text{-}MEAS}$, and $Bz_{TRUE\text{-}MEAS}$ of the calibrating uniform magnetic field measurement $\vec{B}_{TRUE\text{-}MEAS}$ reported by the affixed magnetometers 52x, 52y, and 52z at each of the three-dimensional vector angles (step 260). In the illustrated embodiment, the inherent gain offsets $Bx_0$, $By_0$, $Bz_0$ of the scalar magnetometers 52$x$, 52$y$, and 52$z$ are determined by fitting the inherent gain offsets $Bx_0$, $By_0$, $Bz_0$ to the directional components $Bx_{TRUE\text{-}MEAS}$, $By_{TRUE\text{-}MEAS}$, and $Bz_{TRUE\text{-}MEAS}$ of the calibrating uniform magnetic field measurement $\overline{B_{TRUE\text{-}MEAS}}$ reported by the affixed magnetometers 52$x$, 52$y$, and 52$z$ at each of the three-dimensional vector angles in accordance with equation [15]. In the one preferred embodiment, although the number j of three-dimensional vector angles through which the affixed magnetometers 52$x$, 52$y$, and 52$z$ are rotated and at which the measurements of the orthogonal directional components $Bx_{TRUE\text{-}MEAS}$, $By_{TRUE\text{-}MEAS}$, and $Bz_{TRUE\text{-}MEAS}$ of the calibrating uniform magnetic field $\overline{B_{TRUE\text{-}MEAS}}$ are reported by the affixed magnetometers 52$x$, 52$y$, and 52$z$ need only be four, it is preferred that the number j be much greater than four in order to maximize the accuracy of the determined inherent gain offsets $Bx_0$, $By_0$, $Bz_0$ of the scalar magnetometers 52$x$, 52$y$, and 52$z$.

Although the magnetometer calibration system 50, calibration-enabled magnetometer assemblies 60, and magnetometer pre-calibration system 70 have been described in the context of a signal acquisition unit 18 for more accurately measuring a total residual magnetic field $B_{TOT}$, it should be appreciated that the magnetometer calibration system 50, calibration-enabled magnetometer assemblies 60, and magnetometer pre-calibration system 70 can be used to make measurements of any arbitrary field more accurate.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A calibration system for a magnetometer having an unknown gain, comprising:
   at least one calibration coil affixed relative to the magnetometer;
   at least one driver configured for actuating the at least one calibration coil at a known actuation strength and at a calibration frequency outside of a linear operating range of the magnetometer, such that the at least one calibration coil generates a calibrating magnetic field of a known amplitude at the magnetometer;
   memory storing a roll-off gain error of the magnetometer characterizing roll-off effects of a gain of the magnetometer at a reference frequency within the linear operating range of the magnetometer and a gain of the magnetometer at the calibration frequency;
   at least one processor configured for:
      acquiring a measurement of the calibrating magnetic field reported by the magnetometer;
      recalling the roll-off gain error of the magnetometer from the memory;
      computing a product of the known amplitude of the calibrating magnetic field at the magnetometer and the recalled roll-off gain error of the magnetometer;
      computing a ratio of an amplitude of the acquired calibrating magnetic field measurement reported by the magnetometer and the computed product; and
      determining the unknown gain of the magnetometer at the reference frequency at least partially based on computed ratio.

2. The calibration system of claim 1,
   wherein the magnetometer is a vector magnetometer comprising a plurality of scalar magnetometers having a plurality of unknown gains, and the at least one calibration coil is oriented relative to the plurality of scalar magnetometers of the vector magnetometer, such that the calibrating magnetic field generated by the at least one calibration coil has a plurality of directional components of known amplitudes at the plurality of scalar magnetometers of the vector magnetometer, and the acquired calibrating magnetic field measurement reported by the magnetometer comprises an acquired plurality of directional components of the calibrating magnetic field measurement reported by the plurality of scalar magnetometers of the vector magnetometer;
   wherein the calibration frequency is outside of linear operating ranges of the plurality of scalar magnetometers;
   wherein the memory is configured for storing a plurality of roll-off gain errors of the plurality of scalar magnetometers characterizing roll-off effects of gains of the scalar magnetometers at the reference frequency within the linear operating ranges of the plurality of scalar magnetometers and gains of the plurality of scalar magnetometers at the calibration frequency; and
   wherein the at least one processor is configured for:
      recalling the roll-off gain error of the magnetometer from the memory by recalling the plurality of roll-off gain errors of the plurality of scalar magnetometers from the memory;
      computing the product of the known amplitude of the calibrating magnetic field at the magnetometer and the roll-off gain error of the magnetometer by computing a plurality of products of the known amplitudes of the plurality of directional components of the calibrating magnetic field generated by the at least one calibration coil at the plurality of scalar magnetometers and the plurality of recalled roll-off gain errors of the plurality of scalar magnetometers;
      computing the ratio of the amplitude of the acquired calibrating magnetic field measurement reported by the magnetometer and the known amplitude of the calibrating magnetic field at the magnetometer by computing a plurality of ratios between the acquired plurality of directional component measurements of the calibrating magnetic field reported by the plurality of scalar magnetometers of the vector magnetometer and the plurality of computed products; and
      determining the unknown gain of the magnetometer by determining the plurality of unknown gains of the plurality of scalar magnetometers of the vector magnetometer at least partially based on computed plurality of ratios.

3. The calibration system of claim 2, wherein the plurality of scalar magnetometers of the vector magnetometer are oriented mutually orthogonal to each other, such that the plurality of directional components of the calibrating magnetic field at the plurality of scalar magnetometers of the vector magnetometer are mutually orthogonal to each other, and the acquired plurality of directional component measurements of the calibrating magnetic field reported by the plurality of scalar magnetometers of the vector magnetometer are mutually orthogonal to each other.

4. The calibration system of claim 1, wherein the at least one driver is configured for actuating the at least one calibration coil at the known actuation strength by supplying electrical current at a known amplitude to the at least one calibration coil.

5. The calibration system of claim 1, wherein the at least one processor is configured for outputting at least one control signal respectively to the at least one driver defining the known actuation strength.

6. The calibration system of claim 1, wherein the memory further stores a gain of the at least one calibration coil at the calibration frequency, and the at least one processor is configured for recalling the gain of the at least one calibration coil from the memory, computing a product of the known actuation strength at which the at least one calibration coil is actuated and the recalled gain of the at least one calibration coil, and determining the known amplitude of the calibrating magnetic field at the magnetometer at least partially based on the computed product.

7. A signal acquisition unit, comprising:
  a magnetometer having an unknown gain;
  a calibration system configured for:
    generating a calibrating magnetic field at a known amplitude at the magnetometer and at a calibration frequency outside of a linear operating range of the magnetometer;
    acquiring a measurement of the calibrating magnetic field reported by the magnetometer;
    computing a product of the known amplitude of the calibrating magnetic field at the magnetometer and a roll-off gain error of the magnetometer characterizing roll-off effects of a gain of the magnetometer at a reference frequency within the linear operating range of the magnetometer and a gain of the magnetometer at the calibration frequency;
    computing a first ratio of an amplitude of the calibrating magnetic field measurement reported by the magnetometer and the computed product; and
    determining the unknown gain of the magnetometer at least partially based on computed first ratio; and
  at least one processor is configured for computing a second ratio between an arbitrary magnetic field measurement reported by the magnetometer and the determined gain of the magnetometer, and determining an amplitude of the arbitrary magnetic field at the magnetometer at least partially based on the computed second ratio.

8. The signal acquisition unit of claim 7, wherein the calibration system is configured for storing an inherent gain offset of the magnetometer, and wherein the calibration system is further configured for computing the difference between the computed second ratio and the inherent gain offset of the magnetometer, and determining the amplitude of the arbitrary magnetic field at the magnetometer at least partially based on the computed difference.

9. The signal acquisition unit of claim 7, further comprising:
  at least one magnetic field actuator configured for generating an actuated magnetic field that at least partially cancels an outside magnetic field, thereby yielding a total residual magnetic field at the magnetometer as the arbitrary magnetic field, such that the arbitrary magnetic field measurement reported by the magnetometer is a total residual magnetic field measurement reported by the magnetometer, and the determined amplitude of the arbitrary magnetic field at the magnetometer is a determined amplitude of the total residual magnetic field at the magnetometer;
  wherein the at least one processor is configured for controlling the actuated magnetic field at least partially based on the total residual magnetic field determined at the magnetometer in a manner that suppresses the total residual magnetic field.

10. The signal acquisition unit of claim 9, wherein the magnetometer is a coarse magnetometer, such that the total residual magnetic field measurement reported by the coarse magnetometer is a coarse total residual magnetic field measurement, the signal acquisition unit further comprising a fine magnetometer configured for reporting a fine measurement of the suppressed total residual magnetic field.

11. The signal acquisition unit of claim 10, wherein the coarse magnetometer is a flux gate magnetometer, and the fine magnetometer is an optically pumped magnetometer (OPM).

12. The signal acquisition unit of claim 10,
  wherein the signal acquisition unit is configured for being worn on a head of a user, the signal acquisition unit comprises a support structure to which the coarse magnetometer and the fine magnetometer, are affixed, wherein the total residual magnetic field comprises a magnetoencephalography (MEG) magnetic field; and
  wherein the at least one processor further configured for deriving a MEG signal from the fine measurement of the suppressed total residual magnetic field reported by the fine magnetometer.

13. A neural activity measurement system, comprising:
  the signal acquisition unit of claim 12; and
  a signal processing unit configured for determining an existence of neural activity in a brain of the user based on the derived MEG signal.

14. A calibration method for a magnetometer having an unknown gain, comprising:
  generating a calibrating magnetic field at a known amplitude at the magnetometer and at a calibration frequency outside of a linear operating range of the magnetometer;
  reporting a measurement of the calibrating magnetic field by the magnetometer;
  computing a product of the known amplitude of the calibrating magnetic field at the magnetometer and a roll-off gain error of the magnetometer characterizing roll-off effects of a gain of the magnetometer at a reference frequency within the linear operating range of the magnetometer and a gain of the magnetometer at the calibration frequency;
  computing a first ratio of an amplitude of the calibrating magnetic field measurement reported by the magnetometer and the computed product; and
  determining the unknown gain of the magnetometer at least partially based on computed first ratio.

15. The calibration method of claim 14,
  wherein the magnetometer is a vector magnetometer comprising a plurality of scalar magnetometers having a plurality of unknown gains, such that the calibrating magnetic field has a plurality of directional components of known amplitudes at the plurality of scalar magnetometers of the vector magnetometer, and the calibrating magnetic field measurement reported by the magnetometer comprises a plurality of directional components of the calibrating magnetic field measurement reported by the plurality of scalar magnetometers of the vector magnetometer;

wherein the calibration frequency is outside of linear operating ranges of the plurality of scalar magnetometers;

wherein computing the product of the known amplitude of the calibrating magnetic field at the magnetometer and the roll-off gain error of the magnetometer comprises computing a plurality of products of the known amplitudes of the plurality of directional components of the calibrating magnetic field at the plurality of scalar magnetometers and a plurality of roll-off gain errors of the plurality of scalar magnetometers;

wherein computing the ratio of the amplitude of the calibrating magnetic field measurement reported by the magnetometer and the computed product comprises computing a plurality of ratios between the plurality of directional component measurements of the calibrating magnetic field reported by the plurality of scalar magnetometers of the vector magnetometer and the plurality of computed products; and wherein determining the unknown gain of the magnetometer comprises determining the plurality of unknown gains of the plurality of scalar magnetometers of the vector magnetometer at least partially based on the computed plurality of ratios.

16. The calibration method of claim 15, wherein the plurality of scalar magnetometers of the vector magnetometer are oriented mutually orthogonal to each other, such that the plurality of directional components of the calibrating magnetic field at the plurality of scalar magnetometers of the vector magnetometer are mutually orthogonal to each other, and the plurality of directional component measurements of the calibrating magnetic field reported by the plurality of scalar magnetometers of the vector magnetometer are mutually orthogonal to each other.

17. The calibration method of claim 14, wherein the calibrating magnetic field of the known amplitude at the magnetometer is generated by actuating at least one calibration coil at a known actuation strength, the method further comprising:

computing a product of the known actuation strength at which the at least one calibration coil is actuated and a gain of the at least one calibration coil at the calibration frequency; and determining the known amplitude of the calibrating magnetic field at the magnetometer at least partially based on the computed product.

18. A signal acquisition method, comprising:
performing the calibration method of claim 14;
reporting a measurement of an arbitrary magnetic field by the magnetometer;

computing a second ratio between the arbitrary magnetic field measurement reported by the magnetometer and the determined gain of the magnetometer; and determining an amplitude of the arbitrary magnetic field at the magnetometer at least partially based on the computed second ratio.

19. The signal acquisition method of claim 18, further comprising:

computing the difference between the computed second ratio and an inherent gain offset of the magnetometer; and determining the amplitude of the arbitrary magnetic field at the magnetometer at least partially based on the computed difference.

20. The signal acquisition method of claim 19, further comprising:

generating an actuated magnetic field that at least partially cancels an outside magnetic field, thereby yielding a total residual magnetic field at the magnetometer as the arbitrary magnetic field, such that the arbitrary magnetic field measurement reported by the magnetometer is a total residual magnetic field measurement reported by the magnetometer, and the determined amplitude of the arbitrary magnetic field at the magnetometer is a determined amplitude of the total residual magnetic field at the magnetometer; and controlling the actuated magnetic field at least partially based on the total residual magnetic field determined at the magnetometer in a manner that suppresses the total residual magnetic field.

21. The signal acquisition method of claim 20, wherein the magnetometer is a coarse magnetometer, such that the total residual magnetic field measurement reported by the coarse magnetometer is a coarse total residual magnetic field measurement, the method further comprising reporting a fine measurement of the suppressed total residual magnetic field by a fine magnetometer.

22. The signal acquisition method of claim 21, wherein the coarse magnetometer is a flux gate magnetometer.

23. The signal acquisition method of claim 21, wherein the total residual magnetic field comprises a magnetoencephalography (MEG) magnetic field emanating from a person, the method further comprising deriving a MEG signal from the fine total residual magnetic field measurement reported by the fine magnetometer.

24. A neural activity measurement method, comprising:
performing the signal acquisition method of claim 23; and
determining an existence of neural activity in the a brain of the person based on the derived MEG signal.

* * * * *